US009637481B2

(12) United States Patent
Mohan

(10) Patent No.: US 9,637,481 B2
(45) Date of Patent: May 2, 2017

(54) LIVER X RECEPTOR (LXR) MODULATORS FOR THE TREATMENT OF DERMAL DISEASES, DISORDERS AND CONDITIONS

(71) Applicant: RALEXAR THERAPEUTICS, INC., Malvern, PA (US)

(72) Inventor: Raju Mohan, Malvern, PA (US)

(73) Assignee: Ralexar Therapeutics, Inc., Malvern, PA (US)

( * ) Notice: Subject to any disclaimer, the term of this patent is extended or adjusted under 35 U.S.C. 154(b) by 0 days.

(21) Appl. No.: 14/621,255

(22) Filed: Feb. 12, 2015

(65) Prior Publication Data

US 2015/0152094 A1 Jun. 4, 2015

Related U.S. Application Data

(63) Continuation of application No. 14/474,490, filed on Sep. 2, 2014, now Pat. No. 8,987,318, which is a continuation of application No. PCT/US2013/028438, filed on Feb. 28, 2013.

(60) Provisional application No. 61/606,160, filed on Mar. 2, 2012.

(51) Int. Cl.
| | | |
|---|---|---|
| C07D 417/04 | (2006.01) | |
| C07D 413/04 | (2006.01) | |
| C07D 231/12 | (2006.01) | |
| C07D 231/16 | (2006.01) | |
| C07D 403/04 | (2006.01) | |
| C07D 405/04 | (2006.01) | |
| C07D 409/04 | (2006.01) | |
| A61K 31/4155 | (2006.01) | |

(52) U.S. Cl.
CPC ......... *C07D 417/04* (2013.01); *C07D 231/12* (2013.01); *C07D 231/16* (2013.01); *C07D 403/04* (2013.01); *C07D 405/04* (2013.01); *C07D 409/04* (2013.01); *C07D 413/04* (2013.01)

(58) Field of Classification Search
None
See application file for complete search history.

(56) References Cited

U.S. PATENT DOCUMENTS

| | | | |
|---|---|---|---|
| 8,008,303 | B2 | 8/2011 | Wheelhouse et al. |
| 8,987,318 | B2 | 3/2015 | Mohan |
| 2005/0038248 | A1 | 2/2005 | Henderson et al. |
| 2005/0080111 | A1 | 4/2005 | Bayne et al. |
| 2006/0030612 | A1 | 2/2006 | Steffan et al. |
| 2006/0261319 | A1 | 11/2006 | Gaskins |
| 2010/0069367 | A1 | 3/2010 | Boren |
| 2010/0075964 | A1 | 3/2010 | Busch |
| 2010/0168093 | A1 | 7/2010 | Pericas-Brondo et al. |
| 2010/0331295 | A1 | 12/2010 | Busch |
| 2011/0294784 | A1 | 12/2011 | Asberom |

| | | | |
|---|---|---|---|
| 2012/0040977 | A1 | 2/2012 | Li et al. |
| 2016/0214943 | A1 | 7/2016 | Mohan |
| 2016/0221956 | A1 | 8/2016 | Mohan |

FOREIGN PATENT DOCUMENTS

| | | |
|---|---|---|
| CN | 101248048 | 8/2008 |
| JP | 2011-520884 | 7/2011 |
| WO | WO 02/24632 | 3/2002 |
| WO | WO 03/099769 | 12/2003 |
| WO | WO 03/099775 | 12/2003 |
| WO | WO 2004/058717 | 7/2004 |
| WO | WO 2005/023782 | 3/2005 |
| WO | WO 2005/113499 | 12/2005 |
| WO | WO 2006/003923 | 1/2006 |
| WO | WO 2006/069155 | 6/2006 |
| WO | WO 2006/109633 | 10/2006 |
| WO | WO 2007/002559 | 1/2007 |
| WO | WO 2007/002563 | 1/2007 |
| WO | WO 2007/034279 | 3/2007 |
| WO | WO 2007/092065 | 8/2007 |
| WO | WO 2008/049047 | 4/2008 |
| WO | WO 2008/104077 | 9/2008 |
| WO | WO 2009/011850 | 1/2009 |
| WO | WO 2009/020683 | 2/2009 |
| WO | WO 2009/021868 | 2/2009 |
| WO | WO 2009/086123 | 7/2009 |
| WO | WO 2009/086138 | 7/2009 |
| WO | WO 2009/140089 | 11/2009 |
| WO | WO 2009/150109 | 12/2009 |
| WO | WO 2010/054229 | 5/2010 |
| WO | WO 2010/059627 | 5/2010 |
| WO | WO 2010/096170 | 8/2010 |
| WO | WO 2010/138598 | 12/2010 |
| WO | WO 2011/045415 | 4/2011 |
| WO | WO 2011/46733 | 8/2011 |
| WO | WO 2012/019093 | 2/2012 |
| WO | WO 2012/020820 | 2/2012 |
| WO | WO 2012/027710 | 3/2012 |

(Continued)

OTHER PUBLICATIONS

Carey and Sundbeg, Advanced Organic Chemistry 4th Ed., vols. A and B, 2000 and 2001, Plemum *Too Voluminous*.
Chang et al., Liver X receptor is a therapeutic target for photoaging and chronological skin aging, Mol Endocrinol, Nov. 2008, 22(11):2407-2419.
Extended European Search Report in European Application No. 13754329.4, dated Oct. 12, 2015, 6 pages.
Fieser and Fieser's Reagents for Organic Synthesis, vols. 1-17, 1991, John Wiley and Sons *Too Voluminous*.
Finn et al., "Discovery of a Potent and Selective Series of Pyrazole Bacterial Methionyl-Trna Synthetase Inhibitors," Bioorganic & Medicinal Chemistry Letters, Jan. 2003, 13(13):2231-2234.
Fluhr et al., "Topical Liver X Receptor Activators Accelerate Postnatal Acidification of Stratum Corneum and Improve Function in the Neonate," J. Investigative Dermatology, Dec. 2005, 125:1206-1214.

(Continued)

*Primary Examiner* — Samantha Shterengarts
(74) *Attorney, Agent, or Firm* — Fish & Richardson P.C.

(57) ABSTRACT

Described herein are liver X receptor (LXR) modulators and methods of utilizing LXR modulators in the treatment of dermal diseases, disorders or conditions. Also described herein are pharmaceutical compositions containing such compounds.

28 Claims, 2 Drawing Sheets

(56) References Cited

FOREIGN PATENT DOCUMENTS

| WO | WO 2012/135082 | 10/2012 | |
|---|---|---|---|
| WO | WO 2014/028461 | 2/2014 | |
| WO | WO 2015/035015 | 3/2015 | ........... C07D 401/04 |
| WO | WO 2015/035027 | 3/2015 | ........... C07D 401/04 |

OTHER PUBLICATIONS

Fowler et al., "Liver X receptor activators display anti-inflammatory activity in irritant and allergic contact dermatitis models: liver-X-receptor-specific inhibition of inflammation and primary cytokine production," J. Invest. Dermatol., Feb. 2003, 120:246-255.
GenBank AAM90897, Aug. 2, 2002, 1 page.
GenBank AAY43056, May 22, 2005, 2 pages.
GenBank P55055, Oct. 1, 1996, 2 pages.
GenBank Q13133, Jan. 31, 2000, 2 pages.
GenBank Q5BIS6, Sep. 13, 2005, 2 pages.
GenBank Q5E9B6, May 10, 2005, 1 page.
GenBank Q60644, Oct. 1, 2000, 2 pages.
GenBank Q62685, Oct. 1, 2000, 2 pages.
GenBank Q62755, Oct. 1, 2000, 2 pages.
GenBank Q9Z0Y9, Oct. 1, 2000, 2 pages.
Green and Wuts, Protective Groups in Organic Synthesis $3^{rd}$ Ed., 1999, Wiley *Too Voluminous*.
Hatano et al., "Murine atopic dermatitis responds to peroxisome proliferator-activated receptors alpha and beta/delta (but not gamma) and liver X receptor activators," The Journal of Allergy and Clinical Immunology, Jan. 2010, 125910:160-169.
International Preliminary Report on Patentability in International Application No. PCT/US2013/028438, dated Sep. 2, 2014, 8 pages.
International Search Report in International Application No. PCT/US2013/028438, dated Jun. 18, 2013, 4 pages.
Kocienski, Protective Groups, 1994, Thieme Verlag *Too Voluminous*.
Kumar et al., "Liver X receptor expression in human melanocytes, does it have a role in the pathogenesis of vitiligo?," Experimental Dermatology, 2009, 19:61-64.
Lee et al., "Liver X Receptor Activation Inhibits Melanogenesis through the Acceleration of ERK-Mediated MITF Degradation," J. Invest Dermatol., Dec. 6, 2012, 133:1063-1071.
Madison, "Barrier Function of the Skin: "La Raison d'Etre" of the Epidermis," J. Investigative Dermatology, Aug. 2003, 121(2):231-241.
Man et al., "Basis for Improved Permeability Barrier Homeostasis Induced by PPAR and LXR Activators: Liposensors Stimulate Lipid Synthesis, Lamellar Body Secretion, and Post-Secretory Lipid Processing," J. Investigative Dermatology, 2006, 126:386-392.
March, Advanced Organic Chemistry $4^{th}$ Ed. 1992, Wiley, *Too Voluminous*.
Organic Reactions, vols. 1-40, 1991, John Wiley and Sons *Too Voluiviinous*.
Pencheva et al., "Convergent multi-miRNA targeting of ApoE drives LRP1/LRP8-dependent melanoma metastasis and angiogenesis," Cell, Nov. 21, 2012, 151(5):1068-1082.
Pietrzak et al., "Lipid Disturbances in Psoriasis: An Update," Mediators of Inflammation, 2010, 13 pages.
Remington's Pharmaceutical Sciences 15 Ed., 1975, Mack Publishing Co. *Too Voluminous*.
Rodd'S Chemistry of Carbon Compounds, vols. 1-5 and Supplementals, 1989, Elsevier Scienc Publishers *Too Voluminous*.
Russell et al., "Characterization of liver X receptor expression and function in human skin and the pilosebaceous unit," Experimental Dermatology, 2007, 16:844-852.
Schmuth et al., "Thematic review series: skin lipids. Peroxisome proliferator-activated receptors and liver X receptors in epidermal biology," Journal of Lipid Research, Mar. 2008, 49:499-509.
The Theory and Practice of Industrial Pharmacy, 1970, Lea and Febiger *Too Voluminous*.

Tice et al., "The Medical Chemistry of Liver X Receptor (LXR) Modulators," J. Med Chem, May 15, 2014, retrieved from http://pubs.acs.org, 102 pages.
Viennois et al., "Targeting liver X receptors in human health: deadlock or promising trail?," Expert Opin. Ther. Targets, 2011, 15(2):219-232.
Willy et al., "LXR, a nuclear receptor that defines a distinct retinoid response pathway," Genes & Development, May 1995, 9:1033-1045.
Written Opinion of the International Searching Authority in International Application No. PCT/US2013/028438, dated Jun. 14, 2013, 7 pages.
Zelcer and Tontonz, "Liver X receptors as integrators of metabolic and inflammatory signaling," J. Clinical Investigation, Mar. 2006, 116(3):607-614.
Zhang-Gandhi and Drew, "Liver X receptor and retinoid X receptor agonists inhibit inflammatory responses of microglia and astrocytes," J. Neuroimmunology, 2007, 183:50-59.
Office Action in Chinese Application No. 201380018482.7, issued Aug. 18, 2015, 24 pages, with English translation.
Office Action in Chinese Application No. 201380018482.7, issued Apr. 11, 2016, 20 pages, with English translation.
Reply to European Search Report in European Application No. 13754329.4, dated Apr. 26, 2016, 17 pages.
Office Action in Japanese Application No. 2014-560060, issued Aug. 16, 2016, 13 pages, with English translation.
Dai et al, "Liver X receptor β protects dopaminergic neurons in a mouse model of Parkinson disease," PNAS, 2012, 109:13112-13117.
Geyeregger et al., "Liver X receptors in cardiovascular and metabolic disease," Cell. Mol. Life Sci., Mar. 2006, 63:524-539.
Huynh, T., et al, "Optimization of pyrazole inhibitors of Coactivator Associated Arginine Methyltransferase 1 (CARM1)", Bioorganic & Medicinal Chemistry Letters, 2009, 19(11), 2924-7.
International Preliminary Report on Patentability in International Application No. PCT/US2014/054065, dated Mar. 17, 2016, 15 pages.
International Preliminary Report on Patentability in International Application No. PCT/US2014/54043, dated Mar. 8, 2016, 9 pages.
International Search Report and the Written Opinion in International Application No. PCT/US2014/54043, dated Nov. 25, 2014, 16 pages.
International Search Report and Written Opinion in International Application No. PCT/US14/54065, dated Dec. 19, 2014, 23 pages.
Ishida, "Regulated expression of apolipoprotein E by human retinal pigment epithelial cells," Journal of Lipid Research, 2004, 45:263-271.
Koldamova et al., "The liver X receptor ligand T0901317 decreases amyloid beta production in vitro and in a mouse model of Alzheimer's disease," J. Biol. Chem., Feb. 2005, 280:4079-88.
Lefterov et al., "Expression profiling in APP23 mouse brain. inhibition of Aβ amyloidosis and inflammation in response to LXR agonist treatment," Mol. Neurodegeneration, 2007, 2:20.
Mauch et al., "CNS Synaptogenesis Promoted by Glia-Derived Cholesterol," Science, Nov. 2001, 294:1354-7.
Riddell et al., "The LXR agonist TO901317 selectively lowers hippocampal Abeta42 and improves memory in the Tg2576 mouse model of Alzheimer's disease," Mol. Cell Neurosci., Apr. 2007, 34:621-8.
Sene et al., "Impaired cholesterol efflux in senescent macrophages promotes age-related macular degeneration," Cell Metabolism, Apr. 2013, 17:549-561.
CAS RN 1005621-87-3, STN Entry Date Feb. 28, 2008, 1 page.
CAS RN 1005664-76-5, STN Entry Date Feb. 28, 2008, 1 page.
CAS RN 1005700-88-8, STN Entry Date Feb. 28, 2008, 1 page.
CAS RN 1199770-53-0, STN Entry Date Dec. 31, 2009, 1 page.
CAS RN 1199771-22-6, STN Entry Date Dec. 31, 2009, 1 page.
CAS RN 263160-65-2, STN Entry Date Apr. 26, 2000, 1 page.
CAS RN 292826-84-7, STN Entry Date Oct. 5, 2000, 1 page.
CAS RN 300589-02-0, STN Entry Date Oct. 31, 2000, 1 page.
CAS RN 957264-80-1, STN Entry Date Dec. 10, 2007, 1 page.
CAS RN 957493-13-9, STN Entry Date Dec. 11, 2007, 1 page.
CAS RN 957947-23-8, STN Entry Date Dec. 13, 2007, 1 page.

(56) References Cited

OTHER PUBLICATIONS

CAS RN 959009-61-1, STN Entry Date Dec. 20, 2007, 1 page.
CAS RN 959583-29-0, STN Entry Date Dec. 26, 2007, 1 page.
Chen, H. -S., et al, "Synthesis of 2-Pyrazolyl-5-substituted-1,3,4-oxadiazoles and Their Biological Activities", Chemical Journal of Chinese Universities, 2000, 21(10), 1520-1523 [English Abstract].
Therrien, E., et al, "1,2-Diamines as inhibitors of co-activator associated arginine methyltransferase 1 (CARM1)", Bioorganic & Medicinal Chemistry Letters, 2009, 19(23), 6725-6732.

LIVER X RECEPTOR (LXR) MODULATORS FOR THE TREATMENT OF DERMAL DISEASES, DISORDERS AND CONDITIONS

CROSS-REFERENCE

This application is a continuation of U.S. Ser. No. 14/474,490, filed Sep. 2, 2014, which is a continuation of PCT/US2013/028438, filed Feb. 28, 2013, which claims the benefit of priority of U.S. Provisional Application No. 61/606,160, filed Mar. 2, 2012, each of which is incorporated herein by reference in its entirety.

BACKGROUND OF THE INVENTION

Liver X receptor (LXR) activation is associated with inflammation, hyperproliferative and/or disordered skin barrier differentiation. LXR activation also modulates multiple pathways underlying the etiology and pathology of skin aging.

SUMMARY OF THE INVENTION

Described herein are compounds of Formula A, B, C, D, E, or F, pharmaceutical compositions that include such compounds, and methods of use thereof, for modulating LXR. Also described herein are compounds of Formula I, II, II, IV, V, or VI, pharmaceutical compositions that include such compounds, and methods of use thereof, for modulating LXR. In one aspect is the topical administration of at least one liver X receptor (LXR) modulator described herein to the skin of a mammal in the treatment of dermal diseases, disorders or conditions.

Provided herein are methods and compositions comprising topical administration of a liver X receptor (LXR) modulator for treatment of dermal diseases, disorders or conditions. Dermal diseases, disorders or conditions include, but are not limited to, skin aging, scarring, psoriasis, dermatitis, eczema, urticaria, rosacea, burns, acne, or any other condition described herein. Dermal diseases or disorders also refer to pigmentary disorders including but not limited to vitiligo. Dermal diseases also refer to skin malignancies and cancer, including melanoma and metastatic forms of these diseases.

Accordingly, provided herein are methods and compositions for maintenance of the dermal barrier and/or normalization of the dermal barrier and/or reducing injury to the dermal barrier and/or regeneration of the dermal barrier.

In one aspect provided herein is a method for treating the epidermis of a mammalian subject suffering from a perturbed epidermal barrier function, said method comprising topically administering to said epidermis a topical composition comprising an active ingredient that is an activator of the liver X receptor (LXR), said active ingredient being present in a concentration that is effective in enhancing barrier development.

In another aspect, provided herein is a method for treating the epidermis or mucous membrane of a terrestrial mammalian subject suffering from a condition of disturbed differentiation or excess proliferation, said method comprising topically administering to said epidermis or mucous membrane a topical composition comprising an active ingredient that is an activator of the liver X receptor (LXR), said active ingredient being present in a concentration that is effective in enhancing barrier development.

In some embodiments of the methods or compositions described above, the activator of LXR is a compound of Formula A, B, C, D, E, or F as described herein. In some embodiments of the methods or compositions described above, the activator of LXR is a compound of Formula I, II, III, IV, V, or VI as described herein. In some embodiments of the methods or compositions described above, the concentration of said active ingredient in the topical composition is from about 0.1 µM to 100 µM.

In one aspect is the use of a LXR modulator in the manufacture of a topical formulation for use in the treatment of a dermal disease, disorder or condition in a mammal. In one aspect is the use of a LXR modulator and a second therapeutic agent in the manufacture of a topical formulation for use in the treatment of a dermal disease, disorder or condition in a mammal.

In another aspect is a compound of Formula (A):

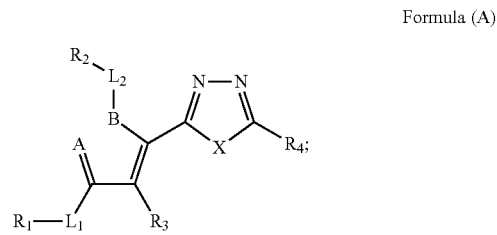

Formula (A)

wherein:
X is —O— or —S—;
A and B are each nitrogen, wherein A and B are bonded together to form a five-membered heteroaryl ring;
$L_1$ and $L_2$ are each independently a bond, $C_1$-$C_6$alkyl, or $C_1$-$C_6$heteroalkyl;
$R_1$ is hydrogen, halogen, —$CF_3$, —$OR_8$, —$N(R_8)_2$, —C(=O)$R_8$, —C(=O)O$R_8$, —C(=O)N($R_8$)$_2$, —C(=N—OH)$R_8$, —C(=S)N($R_8$)$_2$, or —C(=O)OCH$_2$SCH$_3$;
$R_2$ is —$OR_9$, —$N(R_9)_2$, —C(=O)$R_9$, —C(=O)O$R_9$, —C(=O)N($R_9$)$_2$, —$NR_{10}$C(=O)$R_9$, —C(=N—OH)$R_9$, —C(=S)N($R_9$)$_2$, —C(=O)OCH$_2$SCH$_3$, $C_1$-$C_6$alkyl, $C_3$-$C_8$cycloalkyl, $C_1$-$C_6$haloalkyl, $C_1$-$C_6$heteroalkyl, optionally substituted heterocyloalkyl, optionally substituted aryl, or optionally substituted heteroaryl;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —$OR_{10}$, —$N(R_{10})_2$, —CN, —C(=O)$R_{10}$, —C(=O)O$R_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
or a pharmaceutically acceptable salt, pharmaceutically acceptable solvate, or pharmaceutically acceptable prodrug thereof.

In one embodiment is a compound of Formula A wherein $R_4$ is aryl. In a further embodiment is a compound of Formula A wherein $R_1$ is —C(=O)O$R_8$, and $R_8$ is $C_1$-$C_6$alkyl. In a further embodiment is a compound of Formula A wherein $L_2$ is a bond. In a further embodiment is a compound of Formula A wherein $R_2$ is optionally substituted aryl. In a further embodiment is a compound of Formula A wherein $R_2$ is optionally substituted phenyl. In a further embodiment is a compound of Formula A wherein $R_3$ is hydrogen.

In another embodiment is a compound of Formula A wherein $R_4$ is aryl, $R_1$ is —C(=O)$OR_8$, $R_8$ is $C_1$-$C_6$alkyl, and $L_2$ is $C_1$-$C_6$alkyl. In a further embodiment is a compound of Formula A wherein $R_2$ is —$OR_9$, —N($R_9$)$_2$, optionally substituted heterocycloalkyl, optionally substituted aryl, or optionally substituted heteroaryl. In a further embodiment is a compound of Formula A wherein $R_3$ is hydrogen.

In another embodiment is a compound of Formula A wherein $R_4$ is aryl and $R_1$ is —$CF_3$. In a further embodiment is a compound of Formula A wherein $L_2$ is $C_1$-$C_6$alkyl. In a further embodiment is a compound of Formula A wherein $R_2$ is —C(=O)$OR_9$, and $R_9$ is $C_1$-$C_6$alkyl. In a further embodiment is a compound of Formula A wherein $R_3$ is hydrogen. In a further embodiment is a compound of Formula A wherein $R_4$ is phenyl wherein phenyl is substituted with one $R_{11}$. In a further embodiment is a compound of Formula A wherein $R_{11}$ is —$SO_2R_{10}$ and $R_{10}$ is $C_1$-$C_6$alkyl.

In another aspect is a compound of Formula (B):

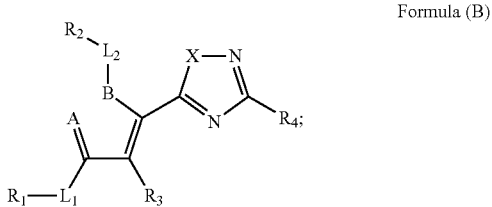

Formula (B)

wherein:
X is —O— or —S—;
A and B are each nitrogen, wherein A and B are bonded together to form a five-membered heteroaryl ring;
$L_1$ and $L_2$ are each independently a bond, $C_1$-$C_6$alkyl, or $C_1$-$C_6$heteroalkyl; $R_1$ is hydrogen, halogen, —$CF_3$, —$OR_8$, —N($R_8$)$_2$, —C(=O)$R_8$, —C(=O)$OR_8$, —C(=O)N($R_8$)$_2$, —C(=N—OH)$R_8$, —C(=S)N($R_8$)$_2$, or —C(=O)$OCH_2SCH_3$;
$R_2$ is —$OR_9$, —N($R_9$)$_2$, —C(=O)$R_9$, —C(=O)$OR_9$, —C(=O)N($R_9$)$_2$, —$NR_{10}$C(=O)$R_9$, —C(=N—OH)$R_9$, —C(=S)N($R_9$)$_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;
$R_3$ is hydrogen, halogen, $C_1$-$C_6$alkyl; or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —$OR_{10}$, —N($R_{10}$)$_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
or a pharmaceutically acceptable salt, pharmaceutically acceptable solvate, or pharmaceutically acceptable pro drug thereof.

In another aspect is a compound of Formula (C):

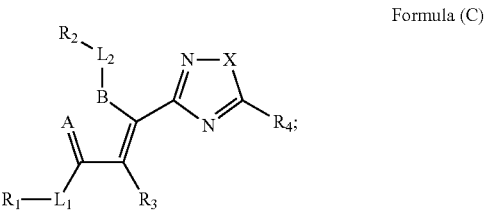

Formula (C)

wherein:
X is —O— or —S—;
A and B are each nitrogen, wherein A and B are bonded together to form a five-membered heteroaryl ring;
$L_1$ and $L_2$ are each independently a bond, $C_1$-$C_6$alkyl, or $C_1$-$C_6$heteroalkyl;
$R_1$ is hydrogen, halogen, —$CF_3$, —$OR_2$, —N($R_8$)$_2$, —C(=O)$R_8$, —C(=O)$OR_8$, —C(=O)N($R_8$)$_2$, —C(=N—OH)$R_8$, —C(=S)N($R_8$)$_2$, or —C(=O)$OCH_2SCH_3$;
$R_2$ is —$OR_9$, —N($R_9$)$_2$, —C(=O)$R_9$, —C(=O)$OR_9$, —C(=O)N($R_9$)$_2$, —$NR_{10}$C(=O)$R_9$, —C(=N—OH)$R_9$, —C(=S)N($R_9$)$_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —$OR_{10}$, —N($R_{10}$)$_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
or a pharmaceutically acceptable salt, pharmaceutically acceptable solvate, or pharmaceutically acceptable prodrug thereof.

In another aspect is a compound of Formula (D):

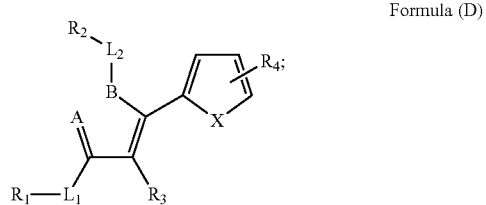

Formula (D)

wherein:
X is —N($R_{12}$)—, or —O—;
A and B are each nitrogen, wherein A and B are bonded together to form a five-membered heteroaryl ring;
$L_1$ is a bond, $C_1$-$C_6$alkyl, or $C_1$-$C_6$heteroalkyl;
$L_2$ is $C_1$-$C_6$alkyl or $C_1$-$C_6$heteroalkyl;
$R_1$ is hydrogen, halogen, —$CF_3$, —$OR_8$, —N($R_8$)$_2$, —C(=O)$R_8$, —C(=O)$OR_8$, —C(=O)N($R_8$)$_2$, —C(=N—OH)R$_8$, —C(=S)N(R$_8$)$_2$, —C(=CH$_2$)CH$_3$, or —C(=O)OCH$_2$SCH$_3$;

R$_2$ is —C(=O)OR$_9$, —C(=O)N(R$_9$)$_2$, —NR$_{10}$C(=O)R$_9$, —C(=N—OH)R$_9$, —C(=S)N(R$_9$)$_2$, or —C(=O)OCH$_2$SCH$_3$;

R$_3$ is hydrogen, halogen, C$_1$-C$_6$alkyl, or C$_1$-C$_6$haloalkyl;

R$_4$ is aryl or heteroaryl; wherein aryl or heteroaryl is substituted with at least one R$_{11}$;

each R$_8$, each R$_9$, and each R$_{10}$ are each independently hydrogen, C$_1$-C$_6$alkyl, C$_1$-C$_6$heteroalkyl, —C$_1$-C$_6$alkyl-aryl, aryl, or heteroaryl;

R$_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, NR$_{10}$SO$_2$R$_{10}$, —SOR$_{10}$, —SO$_2$R$_{10}$, —SO$_2$N(R$_{10}$)$_2$, —C(=O)OCH$_2$SCH$_3$, C$_1$-C$_6$alkyl, C$_3$-C$_8$cycloalkyl, C$_1$-C$_6$haloalkyl, C$_1$-C$_6$heteroalkyl, —C$_1$-C$_6$alkyl-aryl, optionally substituted aryl, or optionally substituted heteroaryl;

R$_{12}$ is hydrogen or C$_1$-C$_6$alkyl;

or a pharmaceutically acceptable salt, pharmaceutically acceptable solvate, or pharmaceutically acceptable prodrug thereof In another aspect is a compound of Formula (E):

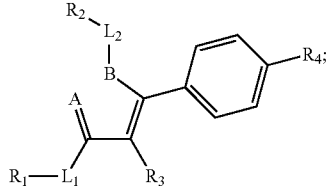

Formula (E)

wherein:

A and B are each nitrogen, wherein A and B are bonded together to form a five-membered heteroaryl ring;

L$_1$ is a bond, C$_1$-C$_6$alkyl, or C$_1$-C$_6$heteroalkyl;

L$_2$ is C$_1$-C$_6$alkyl or C$_1$-C$_6$heteroalkyl;

R$_1$ is hydrogen, halogen, —CF$_3$, —OR$_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$;

R$_2$ is —C(=O)OR$_9$, —C(=O)N(R$_9$)$_2$, —NR$_{10}$C(=O)R$_9$, —C(=N—OH)R$_9$, —C(=S)N(R$_9$)$_2$, or —C(=O)OCH$_2$SCH$_3$;

R$_3$ is hydrogen, halogen, C$_1$-C$_6$alkyl, or C$_1$-C$_6$haloalkyl;

R$_4$ is aryl or heteroaryl; wherein aryl or heteroaryl is substituted with at least one R$_{11}$; each R$_8$, each R$_9$, and each R$_{10}$ are each independently hydrogen, C$_1$-C$_6$alkyl, C$_1$-C$_6$heteroalkyl, —C$_1$-C$_6$alkyl-aryl, aryl, or heteroaryl;

R$_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, NR$_{10}$SO$_2$R$_{10}$, —SOR$_{10}$, —SO$_2$R$_{10}$, —SO$_2$N(R$_{10}$)$_2$, —C(=O)OCH$_2$SCH$_3$, C$_1$-C$_6$alkyl, C$_3$-C$_8$cycloalkyl, C$_1$-C$_6$haloalkyl, C$_1$-C$_6$heteroalkyl, —C$_1$-C$_6$alkyl-aryl, optionally substituted aryl, or optionally substituted heteroaryl;

or a pharmaceutically acceptable salt, pharmaceutically acceptable solvate, or pharmaceutically acceptable prodrug thereof In one embodiment is a compound of Formula E wherein R$_4$ is aryl. In a further embodiment is a compound of Formula E wherein R$_2$ is —C(=O)OR$_9$, and R$_9$ is C$_1$-C$_6$alkyl or C$_1$-C$_6$heteroalkyl. In a further embodiment is a compound of Formula E wherein L$_2$ is C$_1$-C$_6$alkyl. In a further embodiment is a compound of Formula E wherein L$_2$ is —CH$_2$—. In a further embodiment is a compound of Formula E wherein L$_1$ is a bond. In a further embodiment is a compound of Formula E wherein R$_1$ is —CF$_3$, —C(=O)R$_8$, —C(=O)OR$_8$, —C(=O)N(R$_8$)$_2$, or —C(=CH$_2$)CH$_3$. In a further embodiment is a compound of Formula E wherein R$_4$ is phenyl wherein phenyl is substituted with one R$_{11}$. In a further embodiment is a compound of Formula E wherein R$_{11}$ is —SO$_2$R$_{10}$ and R$_{10}$ is C$_1$-C$_6$alkyl.

In another aspect is a compound of Formula (F):

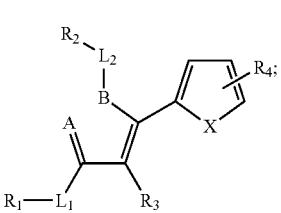

Formula (F)

wherein:

X is —S—;

A and B are each nitrogen, wherein A and B are bonded together to form a five-membered heteroaryl ring;

L$_1$ is a bond, C$_1$-C$_6$alkyl, or C$_1$-C$_6$heteroalkyl;

L$_2$ is C$_1$-C$_6$alkyl or C$_1$-C$_6$heteroalkyl;

R$_1$ is hydrogen, halogen, C$_1$-C$_6$alkyl, C$_2$-C$_6$alkenyl, C$_2$-C$_6$alkynyl, —CF$_3$, —OR$_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$;

R$_2$ is —C(=O)OR$_{13}$, —NR$_{10}$C(=O)R$_9$, —C(=N—OH)R$_9$, —C(=S)N(R$_9$)$_2$, or —C(=O)OCH$_2$SR$_{15}$;

R$_3$ is hydrogen, halogen, C$_1$-C$_6$alkyl, or C$_1$-C$_6$haloalkyl;

R$_4$ is aryl or heteroaryl; wherein aryl or heteroaryl is substituted with at least one R$_{11}$; each R$_8$, each R$_9$, and each R$_{10}$ are each independently hydrogen, C$_1$-C$_6$alkyl, C$_1$-C$_6$heteroalkyl, —C$_1$-C$_6$alkyl-aryl, aryl, or heteroaryl;

R$_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, —NR$_{10}$SO$_2$R$_{10}$, —SOR$_{10}$, —SO$_2$R$_{14}$, —SO$_2$N(R$_{10}$)$_2$, —C(=O)OCH$_2$SCH$_3$, optionally substituted C$_1$-C$_6$alkyl, optionally substituted C$_3$-C$_8$cycloalkyl, C$_1$-C$_6$haloalkyl, optionally substituted C$_1$-C$_6$heteroalkyl, optionally substituted —C$_1$-C$_6$alkyl-aryl, optionally substituted aryl, or optionally substituted heteroaryl;

R$_{13}$ is hydrogen, C$_1$-C$_6$alkyl, C$_1$-C$_6$heteroalkyl, —C$_1$-C$_6$alkyl-aryl, aryl, or heteroaryl;

R$_{14}$ is C$_1$-C$_6$alkyl, C$_1$-C$_6$heteroalkyl, —C$_1$-C$_6$alkyl-aryl, aryl, or heteroaryl;

R$_{15}$ is C$_1$-C$_6$alkyl;

or a pharmaceutically acceptable salt, pharmaceutically acceptable solvate, or pharmaceutically acceptable prodrug thereof.

In one embodiment is a compound of Formula F wherein R$_2$ is —C(=O)OR$_{13}$ and R$_{13}$ is C$_2$-C$_6$alkyl, C$_1$-C$_6$heteroalkyl, —C$_1$-C$_6$alkyl-aryl, aryl, or heteroaryl. In a further embodiment is a compound of Formula F wherein R$_{13}$ is C$_2$-C$_6$alkyl or C$_1$-C$_6$heteroalkyl. In a further embodiment is a compound of Formula F wherein R$_4$ is phenyl. In a further embodiment is a compound of Formula F wherein $R_4$ is substituted with at least two $R_{11}$. In a further embodiment is a compound of Formula F wherein $R_{11}$ is independently halogen, $-SO_2R_{14}$, $-NR_{10}SO_2R_{10}$, or $-SO_2N(R_{10})_2$.

In another embodiment is a compound of Formula F wherein $R_2$ is $-C(=O)OR_{13}$; $R_{13}$ is $C_2$-$C_6$alkyl or $C_1$-$C_6$heteroalkyl; $R_4$ is phenyl substituted with one $R_{11}$; and $R_{11}$ is $-SO_2R_{14}$. In a further embodiment is a compound of Formula F wherein $R_{14}$ is $C_1$-$C_6$alkyl.

In another embodiment is a compound of Formula F wherein $R_2$ is $-C(=O)OR_{13}$; $R_{13}$ is $C_2$-$C_6$alkyl or $C_1$-$C_6$heteroalkyl; $R_4$ is phenyl substituted with one $R_{11}$, $R_{11}$ is $-SO_2R_{14}$, and $R_{14}$ is $C_2$-$C_6$alkyl, $C_1$-$C_6$heteroalkyl, $-C_1$-$C_6$alkyl-aryl, aryl, or heteroaryl. In a further embodiment is a compound of Formula F wherein $R_{14}$ is $C_2$-$C_6$alkyl. In a further embodiment is a compound of Formula F wherein $L_2$ is $C_1$-$C_6$alkyl. In a further embodiment is a compound of Formula F wherein $L_2$ is $-CH_2-$. In a further embodiment is a compound of Formula F wherein $L_1$ is a bond. In a further embodiment is a compound of Formula F wherein $R_1$ is hydrogen, halogen, $C_1$-$C_6$alkyl, $C_2$-$C_6$alkenyl, $C_2$-$C_6$alkynyl, $-OR_8$, $-N(R_8)_2$, $-C(=O)R_8$, $-C(=O)OR_8$, $-C(=O)N(R_8)_2$, $-C(=N-OH)R_8$, $-C(=S)N(R_8)_2$, $-C(=CH_2)CH_3$, or $-C(=O)OCH_2SCH_3$. In a further embodiment is a compound of Formula F wherein $R_1$ is $C_1$-$C_6$alkyl, or $-C(=CH_2)CH_3$.

In another aspect is a pharmaceutical composition comprising a compound of Formula A, B, C, D, E, or F, and a pharmaceutically acceptable diluent, excipient, carrier or binder thereof. In another aspect is a pharmaceutical composition comprising a compound of Formula I, II, III, IV, V, or VI, and a pharmaceutically acceptable diluent, excipient, carrier or binder thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
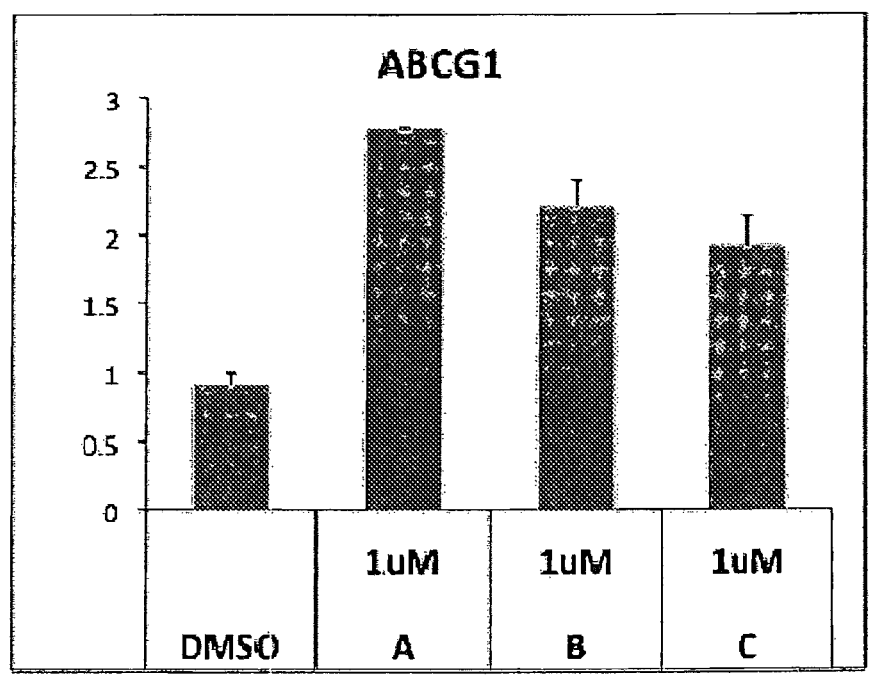
FIG. 1 shows ABCG1 gene expression analyzed by real-time PCR for three compounds of Formula I-VI: Compound A, Compound B, and Compound C as outlined in Example 29.

LXR was first described by Willy, P. J., et al., "LXR, a nuclear receptor that defines a distinct retinoid response pathway," Genes & Development 9:1033-1045 (Cold Spring Harbor Laboratory Press).

The liver X receptors (LXR alpha and LXR beta) are highly expressed in the epidermis and LXR activators stimulate keratinocyte proliferation and differentiation. Activation of LXRs also improves permeability barrier homeostasis by a number of mechanisms, including stimulating epidermal lipid synthesis, increasing lamellar body formation and secretion, and increasing the activity of enzymes required for the extracellular processing of lipids in the stratum corneum, leading to the formation of lamellar membranes that mediate permeability barrier function. LXR activation is also anti-inflammatory, reducing inflammation in animal models of allergic and irritant contact dermatitis. (Schmuth et al. 2008, Journal of Lipid Research, 49, 499-509).

The epidermis serves to form a barrier against excessive transcutaneous water loss to the environment. This barrier is formed by the anucleate, cornified, outermost layers of the epidermis, collectively known as the stratum corneum. The stratum corneum regulates a natural rate of water loss in the skin, a process called Transepidermal Water Loss (or TEWL). Normal, healthy moisturized skin loses about 80-100 grams of water into the atmosphere each day. The TEWL process is affected by the integrity of the epidermal barrier and lipid structure and for healthy skin, these elements regulate the rate of TEWL and help maintain the proper moisture levels in the stratum corneum.

Thus, maintenance of a normal epidermal barrier is a physiological means of inhibiting epidermal hyperproliferation.

Examples of conditions that involve or give rise to a disrupted or dysfunctional epidermal barrier are: inflammation to mucous membranes, such as cheilitis, chapped lips, nasal irritation and vulvovaginitis; eczematous dermnatitides, such as atopic and seborrheic dermatitis, allergic or irritant contact dermatitis, eczema craquelee, photoallergic dermatitis, phototoxic dermatitis, phytophotodermatitis, radiation dermatitis, and stasis dermatitis; ulcers and erosions resulting from trauma, burns, bullous disorders, or ischemia of the skin or mucous membranes; several forms of ichthyoses; epidermolysis bullosae; psoriasis; hypertrophic scars and keloids and cutaneous changes of intrinsic aging and photoaging; and the like.

The constituents of the epidermis that play a role in maintenance of a functional barrier are the intercellular, lamellar bilayer sheets of stratum corneum lipids. The synthesis of stratum corneum lipids is relatively autonomous from circulating or dietary influences. The synthetic response is regulated instead by alterations in permeability barrier functions. The regulation occurs through changes in the activities, phosphorylation (activation) state, mass, and mRNA for the rate-limiting enzymes of each of the three key lipids: serine palmitoyl transferase (for ceramides), HMG-CoA reductase (for cholesterol), and both acetyl CoA carboxylase and fatty acid synthase (for fatty acids). Other results of alterations in barrier function are the regulation of key enzymes of extracellular lipid processing. One such enzyme is beta-glucocerebrosidase, which catalyzes the conversion of precursor glycosylceramides into ceramides.

It has now been discovered that the formation of a mature, fully differentiated stratum corneum and a functional epidermal permeability barrier are accelerated by the topical administration of certain activators of liver X receptor (LXR) with its two isoforms, LXR alpha and LXR beta.

LXR activators improve barrier function by at least two parallel mechanisms—stimulation of epidermal differentiation and lipid production. Since increased epidermal lipid production likely generates additional endogenous activators of these nuclear hormone receptors, this process can be viewed as a type of feed-forward mechanism that coordinately regulates generation of both the corneocytes and the extracellular matrix of the stratum corneum.

Hatano et al. have shown that topical application of LXR activators improves multiple parameters of the AD-like dermatosis in a hapten-induced mouse model (Hatano et al (2010) The Journal of Allergy and Clinical Immunology 125 (1) 160-169. This model recapitulates virtually all of the known clinical, structural, functional, lipid biochemical, and immunologic abnormalities of human AD.

Inherited abnormalities in proteins important for the barrier predispose to the development of atopic dermatitis (AD). Conversely, normalization of barrier function would, in turn, reduce the two major drivers of inflammation in AD. Provided herein are methods for reducing cytokine generation, originating from, for example, perturbed corneocytes. In one embodiment, treatment with topical LXR activators reduces IL-1α and TNFα levels. In addition, improved permeability barrier function simultaneously reduces the transdermal penetration of pro-inflammatory xenobiotes, including haptens and microbial pathogens.

Chang et al (Mol Endocrinol 2008, 22, 2407-2419) have shown the efficacy of the LXR ligands in normal human epidermal keratinocytes and in a mouse model of photoaging. A comprehensive molecular basis for the efficacy in the mouse model was established by in vitro studies in normal human epidermal keratinocytes and in skin cell preparations from LXR wild-type and LXR knock-out mice. In these studies, LXR activators:

(a) reduced the expression of cytokines and metalloproteinases in UV-activated epidermal keratinocytes and TNFα-activated dermal fibroblasts
(b) increased the expression of keratinocyte differentiation markers
(c) increased the expression of genes required for fatty acid synthesis in keratinocytes
(d) increased the expression of cholesterol binding proteins and lipid transporters in skin cells
(e) increased the expression of enzymes involved in ceramide synthesis in keratinocytes.

Lee et al (J Invest Dermatol. 2012 Dec. 6. doi: 10.1038/jid.2012.409. [Epub ahead of print]) have shown that in human primary melanocytes, MNT-1, and B16 melanoma cells, LXR activation and LXR agonists have been shown to inhibit melanogenesis by downregulating melanogenic enzymes through Ras- and ERK-induced MITF degradation. This supports the rationale that LXRs may be key target proteins for in pigmentary disorders and that LXR agonists may be beneficial in the treatment of dermal pigmantary disorders including vitiligo.

Pencheva et al (*Cell.* 2012 Nov. 21; 151(5):1068-82) have shown that targeting apolipoproteins in the skin such as ApoE convergently effects molecular targets such as LRP1/LRP8 which are implicated in melanoma metastasis and angiogenesis. As ApoE is a target gene for LXR, LXR activation may be beneficial in the treatment of dermal malignancies including metastatic melanoma.

Accordingly provided herein are methods and compositions comprising LXR activators as active ingredients in a formulation that is pharmaceutically acceptable for topical administration.

Topical formulations containing LXR activators or activators described herein are applied to beneficial effect to skin and/or mucus membranes. The activators are formulated as lotions, solutions, gels, creams, emollient creams, unguents, sprays, or any other form that will permit topical application. The formulation may also contain one or more agents that promote the spreading of the formulation over the affected area, but are otherwise biologically inactive. Examples of these agents are surfactants, humectants, wetting agents, emulsifiers, or propellants.

Amounts that are referred to herein as effective in enhancing barrier development are any amount that will cause a substantial relief of the symptoms of a disrupted or dysfunctional epidermal permeability barrier when applied repeatedly over time. The optimum amounts in any given instance will be readily apparent to those skilled in the art or are capable of determination by routine experimentation.

Examples of skin conditions that are susceptible to topical treatment with LXR activators are: atopic and seborrheic dermatitis; inflammation to mucous membranes, such as cheilitis, chapped lips, nasal irritation and vulvovaginitis; eczematous dermatitis resulting from allergic and irritant contact, eczema craquelee, radiation and stasis dermatitis; ulcers and erosions due to chemical or thermal burns, bullous disorders, or vascular compromise or ischemia including venous, arterial, embolic or diabetic ulcers; ichthyoses, with or without an associated barrier abnormality; epidermolysis bullosa; psoriasis; hypertrophic scars and keloids; intrinsic aging, photo aging and/or dermatoheliosus; melanoma and non-melanoma skin cancer, including lignin melanoma, basal cell carcinoma, squamous cell carcinoma, actinic keratoses, and virally induced neoplasia (warts and condylomata accuminata).

Optimal methods and frequency of administration will be readily apparent to those skilled in the art or are capable of determination by routine experimentation. Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The methods and compositions described herein are generally applicable to the treatment of mammalian skin including for example humans, domestic pets, and livestock and other farm animals.

DEFINITIONS

In the context of this disclosure, a number of terms shall be utilized.

As used herein, the term "about" or "approximately" means within 20%, preferably within 10%, and more preferably within 5% of a given value or range.

The term a "therapeutically effective amount" as used herein refers to the amount of an LXR modulator that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule. For example, a TIMP1 modulator is considered to modulate the expression of TIMP1 if the presence of such TIMP1 modulator results in an increase or decrease in TIMP1 expression.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The terms "induce" or "induction" of TIMP1, ASAH1, SPTLC1, SMPD1, LASS2, TXNRD1, GPX3, GSR, CAT, ApoE, ABCA1, ABCA2, ABCA12, ABCA13, ABCG1, or decorin expression refer to an increase, induction, or otherwise augmentation of TIMP1, ASAH1, SPTLC1, SMPD1, LASS2, TXNRD1, GPX3, GSR, CAT, ApoE, ABCA1, ABCA2, ABCA12, ABCA13, ABCG1, or decorin mRNA and/or protein expression. The increase, induction, or augmentation can be measured by one of the assays provided herein. Induction of TIMP1, ASAH1, SPTLC1, SMPD1, LASS2, TXNRD1, GPX3, GSR, CAT, ApoE, ABCA1, ABCA2, ABCA12, ABCA13, ABCG1, or decorin expression does not necessarily indicate maximal expression of TIMP1, ASAH1, SPTLC1, SMPD1, LASS2, TXNRD1, GPX3, GSR, CAT, ApoE, ABCA1, ABCA2, ABCA12, ABCA13, ABCG1, or decorin. An increase in TIMP1, ABCA12, or decorin expression can be, for example, at least about 10%, 20%, 30%, 40%, 50%, 60%, 70%, 80%, 90% or more. In one embodiment, induction is measured by comparing TIMP1, ASAH1, SPTLC1, SMPD1, LASS2, TXNRD1, GPX3, GSR, CAT, ApoE, ABCA1, ABCA2, ABCA12, ABCA13, ABCG1, or decorin mRNA expression levels from untreated keratinocytes to that of TIMP1, ASAH1, SPTLC1, SMPD1, LASS2, TXNRD1, GPX3, GSR, CAT, ApoE, ABCA1, ABCA2, ABCA12, ABCA13, ABCG1, or decorin mRNA expression levels from LXR modulator-treated keratinocytes.

The terms "inhibit" or "inhibition" of TNFα, MMP1, MMP3, or IL-8 expression refer to a reduction, inhibition, or otherwise diminution of TNFα, MMP1, MMP3, or IL-8 mRNA and/or protein expression. The reduction, inhibition, or diminution of binding can be measured by one of the assays provided herein. Inhibition of TNFα, MMP1, MMP3, or IL-8 expression does not necessarily indicate a complete negation of TNFα, MMP1, MMP3, or IL-8 expression. A reduction in expression can be, for example, at least about 10%, 20%, 30%, 40%, 50%, 60%, 70%, 80%, 90% or more. In one embodiment, inhibition is measured by comparing TNFα, MMP1, MMP3, or IL-8 mRNA expression levels from untreated keratinocytes to that of TNFα, MMP1, MMP3, or IL-8 mRNA expression levels from LXR modulator-treated keratinocytes.

"Liver X receptor" or "LXR" refers to both LXRα and LXRβ, and variants, isoforms, and active fragments thereof. LXRβ is ubiquitously expressed, while LXRα expression is limited to liver, kidney, intestine, spleen, adipose tissue, macrophages, skeletal muscle, and, as demonstrated herein, skin. Representative GenBank® accession numbers for LXRα sequences include the following: human (*Homo sapiens*, Q 13133), mouse (*Mus musculus*, Q9Z0Y9), rat (*Rattus norvegicus*, Q62685), cow (*Bos taurus*, Q5E9B6), pig (*Sus scrofa*, AAY43056), chicken (*Gallus gallus*, AAM90897). Representative GenBank® accession numbers for LXRβ include the following: human (*Homo sapiens*, P55055), mouse (*Mus musculus*, Q60644), rat (*Rattus norvegicus*, Q62755), cow (*Bos taurus*, Q5BIS6).

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Proinflammatory cytokine" as used herein refers to any cytokine that can activate cytotoxic, inflammatory, or delayed hypersensitivity reactions. Exemplary proinflammatory cytokines include colony stimulating factors (CSFs), for example granulocyte-macrophage CSF, granulocyte CSF, erythropoietin; transforming growth factors (TGFs), for example TGFβ; interferons (IFNs), for example IFNα, IFNβ, IFNγ; interleukins (ILs), for example IL-1α, IL-1β, IL-3, IL-6, IL-7, IL-8, IL-9, IL-11, IL-12, IL-15; tumor necrosis factors (TNFs), for example TNFα, TNFβ; adherence proteins, for example intracellular adhesion molecule (ICAM), vascular cell adhesion molecule (VCAM); growth factors, for example leukemia inhibitory factor (LIF), macrophage migration-inhibiting factor (MIF), epidermal growth factor (EGF), platelet-derived growth factor (PDGF), fibroblast growth factor (FGF), insulin-like growth factor (IGF), nerve growth factor (NGF), B-cell growth factor (BCGF); chemokines, for example monocyte chemoattractant proteins (MCP-1, MCP-2, MCP-3), macrophage inflammatory protein (MIP), growth-related oncogene, gamma interferon-inducible protein; leukotrienes, for example leukotriene B4, leukotrine $D_4$; vasoactive factors, for example histamine, bradykinin, platelet activating factor (PAF); prostaglandins, for example prostaglandin $E_2$.

The term "skin aging" includes conditions derived from intrinsic chronological aging (for example, deepened expression lines, reduction of skin thickness, inelasticity, and/or unblemished smooth surface), those derived from photoaging (for example, deep wrinkles, yellow and leathery surface, hardening of the skin, elastosis, roughness, dyspigmentations (age spots) and/or blotchy skin), and those derived from steroid-induced skin thinning.

LXR Modulators

LXR modulators contemplated for use in the compositions and methods described herein are compounds with LXRα and/or LXRβ modulator activities. The term "LXR modulator" includes LXRα and/or LXRβ agonists, antagonists and tissue selective LXR modulators, as well as other agents that induce the expression and/or protein levels of LXRs in the skin cells.

Preferred compounds will be LXR modulators with LXRα and/or LXRβ modulator activities. Preferred LXR modulators are LXR activators. The term "LXR activator" or "activator of the LXR" includes LXRα and/or LXRβ agonists, partial agonists and tissue selective LXR modulators, as well as other agents that induce the expression and/or protein levels of LXRs in the skin cells.

In one aspect is a compound of Formula (A):

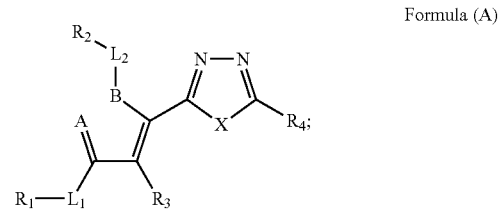

Formula (A)

wherein:

X is —O— or —S—;

A and B are each nitrogen, wherein A and B are bonded together to form a five-membered heteroaryl ring;

$L_1$ and $L_2$ are each independently a bond, $C_1$-$C_6$alkyl, or $C_1$-$C_6$heteroalkyl;

$R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, or —C(=O)$OCH_2SCH_3$;

$R_2$ is —$OR_9$, —$N(R_9)_2$, —C(=O)$R_9$, —C(=O)$OR_9$, —C(=O)$N(R_9)_2$, —$NR_{10}$C(=O)$R_9$, —C(=N—OH)$R_9$, —C(=S)$N(R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

or a pharmaceutically acceptable salt, pharmaceutically acceptable solvate, or pharmaceutically acceptable prodrug thereof.

In another aspect is a compound of Formula (I):

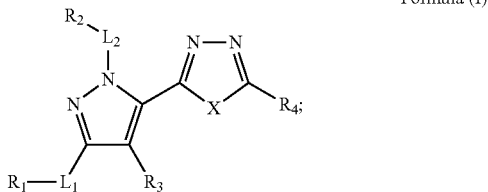

Formula (I)

wherein:

X is —O— or —S—;

$L_1$ and $L_2$ are each independently a bond, $C_1$-$C_6$alkyl, or $C_1$-$C_6$heteroalkyl;

$R_1$ is hydrogen, halogen, —$CF_3$, —$OR_8$, —$N(R_8)_2$, —C(=O)$R_8$, —C(=O)$OR_8$, —C(=O)N($R_8$)$_2$, —C(=N—OH)$R_8$, —C(=S)N($R_8$)$_2$, or —C(=O)$OCH_2SCH_3$;

$R_2$ is —$OR_9$, —$N(R_9)_2$, —C(=O)$R_9$, —C(=O)$OR_9$, —C(=O)N($R_9$)$_2$, —$NR_{10}$C(=O)$R_9$, —C(=N—OH)$R_9$, —C(=S)N($R_9$)$_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

or a pharmaceutically acceptable salt, pharmaceutically acceptable solvate, or pharmaceutically acceptable prodrug thereof.

In some embodiments is a compound of Formula I wherein X is —O—. In further embodiments, $R_1$ is hydrogen, halogen, —$CF_3$, —$OR_8$, —$N(R_8)_2$, —C(=O)$R_8$, —C(=O)$OR_8$, —C(=O)N($R_8$)$_2$, —C(=N—OH)$R_8$, —C(=S)N($R_8$)$_2$, or —C(=O)$OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —C(=O)$R_8$. In some embodiments, $R_1$ is —C(=O)$OR_8$. In some embodiments, $R_1$ is —C(=O)N($R_8$)$_2$. In some embodiments, $R_1$ is —C(=N—OH)$R_8$. In some embodiments, $R_1$ is —C(=S)N($R_8$)$_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —C(=O)$OCH_2SCH_3$.

In some embodiments is a compound of Formula I wherein X is —O— and $R_2$ is —$OR_9$, —$N(R_9)_2$, —C(=O)$R_9$, —C(=O)$OR_9$, —C(=O)N($R_9$)$_2$, —$NR_{10}$C(=O)$R_9$, —C(=N—OH)$R_9$, —C(=S)N($R_9$)$_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl. In some embodiments, $R_2$ is —$OR_9$. In some embodiments, $R_2$ is —$N(R_9)_2$. In some embodiments, $R_2$ is —C(=O)$R_9$. In some embodiments, $R_2$ is —C(=O)$OR_9$. In some embodiments, $R_2$ is —C(=O)N($R_9$)$_2$. In some embodiments, $R_2$ is —$NR_{10}$C(=O)$R_9$. In some embodiments, $R_2$ is —C(=N—OH)$R_9$. In some embodiments, $R_2$ is —C(=S)N($R_9$)$_2$. In some embodiments, $R_2$ is —C(=O)$OCH_2SCH_3$. In some embodiments, $R_2$ is $C_1$-$C_6$alkyl. In some embodiments, $R_2$ is $C_3$-$C_8$cycloalkyl. In some embodiments, $R_2$ is $C_1$-$C_6$haloalkyl. In some embodiments, $R_2$ is $C_1$-$C_6$heteroalkyl. In some embodiments, $R_2$ is optionally substituted heterocycloalkyl. In some embodiments, $R_2$ is optionally substituted aryl. In some embodiments, $R_2$ is optionally substituted heteroaryl. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula I wherein X is —O— and $L_1$ and $L_2$ are each independently a bond, $C_1$-$C_6$alkyl, or $C_1$-$C_6$heteroalkyl. In further embodiments, $L_1$ and $L_2$ are each a bond. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is a bond. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is a bond. In further embodiments, $L_1$ is $C_1$-$C_6$heteroalkyl and $L_2$ is $C_1$-$C_6$alkyl.

In some embodiments is a compound of Formula I wherein X is —O— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula I wherein X is —O—, $R_4$ is phenyl substituted with at least one $R_{11}$, and each $R_{11}$ is independently —$OR_{10}$, —$N(R_{10})_2$, —CN, —$C(=O)R_{10}$, —$C(=O)OR_{10}$, —$C(=O)N(R_{10})_2$, —$NR_{10}C(=O)R_{10}$, $NR_{10}SO_2R_{10}$, —$SOR_{10}$, —$SO_2R_{10}$, —$SO_2N(R_{10})_2$, —$C(=O)OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula I wherein X is —O—, $R_4$ is heteroaryl substituted with at least one $R_{11}$, and each $R_{11}$ is independently —$OR_{10}$, —$N(R_{10})_2$, —CN, —$C(=O)R_{10}$, —$C(=O)OR_{10}$, —$C(=O)N(R_{10})_2$, —$NR_{10}C(=O)R_{10}$, $NR_{10}SO_2R_{10}$, —$SOR_{10}$, —$SO_2R_{10}$, —$SO_2N(R_{10})_2$, —$C(=O)OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —$C(=O)R_{10}$. In further embodiments, $R_{11}$ is —$C(=O)OR_{10}$. In further embodiments, $R_{11}$ is —$C(=O)N(R_{10})_2$. In further embodiments, $R_{11}$ is —$NR_{10}C(=O)R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —$C(=O)OCH_2SCH_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula I wherein X is —O—, $R_1$ is $C(=O)OR_8$, Re is $C_1$-$C_6$alkyl, and $L_2$ is a bond. In a further embodiment, $R_2$ is optionally substituted phenyl. In a further embodiment, $R_2$ is optionally substituted heteroaryl. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula I wherein X is —O—, $R_1$ is $C(=O)OR_8$, $R_8$ is $C_1$-$C_6$alkyl, and $L_2$ is $C_1$-$C_6$alkyl. In a further embodiment, $R_2$ is optionally substituted phenyl. In a further embodiment, $R_2$ is optionally substituted heterocycloalkyl. In a further embodiment, $R_2$ is —$OR_9$. In a further embodiment, $R_2$ is —$N(R_9)_2$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula I wherein X is —O—, $L_1$ is a bond, $R_1$ is —$CF_3$, $L_2$ is $C_1$-$C_6$alkyl, $R_2$ is $C(=O)OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In some embodiments is a compound of Formula I wherein X is —S—. In further embodiments, $R_1$ is hydrogen, halogen, —$CF_3$, —$OR_8$, —$N(R_8)_2$, —$C(=O)R_8$, —$C(=O)OR_8$, —$C(=O)N(R_8)_2$, —$C(=N-OH)R_8$, —$C(=S)N(R_8)_2$, or —$C(=O)OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —$C(=O)R_8$. In some embodiments, $R_1$ is —$C(=O)OR_8$. In some embodiments, $R_1$ is —$C(=O)N(R_8)_2$. In some embodiments, $R_1$ is —$C(=N-OH)R_8$. In some embodiments, $R_1$ is —$C(=S)N(R_8)_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —$C(=O)OCH_2SCH_3$.

In some embodiments is a compound of Formula I wherein X is —S— and $R_2$ is —$OR_9$, —$N(R_9)_2$, —$C(=O)R_9$, —$C(=O)OR_9$, —$C(=O)N(R_9)_2$, —$NR_{10}C(=O)R_9$, —$C(=N-OH)R_9$, —$C(=S)N(R_9)_2$, —$C(=O)OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl. In some embodiments, $R_2$ is —$OR_9$. In some embodiments, $R_2$ is —$N(R_9)_2$. In some embodiments, $R_2$ is —$C(=O)R_9$. In some embodiments, $R_2$ is —$C(=O)OR_9$. In some embodiments, $R_2$ is —$C(=O)N(R_9)_2$. In some embodiments, $R_2$ is —$NR_{10}C(=O)R_9$. In some embodiments, $R_2$ is —$C(=N-OH)R_9$. In some embodiments, $R_2$ is —$C(=S)N(R_9)_2$. In some embodiments, $R_2$ is —$C(=O)OCH_2SCH_3$. In some embodiments, $R_2$ is $C_1$-$C_6$alkyl. In some embodiments, $R_2$ is $C_3$-$C_8$cycloalkyl. In some embodiments, $R_2$ is $C_1$-$C_6$haloalkyl. In some embodiments, $R_2$ is $C_1$-$C_6$heteroalkyl. In some embodiments, $R_2$ is optionally substituted heterocycloalkyl. In some embodiments, $R_2$ is optionally substituted aryl. In some embodiments, $R_2$ is optionally substituted heteroaryl. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula I wherein X is —S— and $L_1$ and $L_2$ are each independently a bond, $C_1$-$C_6$alkyl, or $C_1$-$C_6$heteroalkyl. In further embodiments, $L_1$ and $L_2$ are each a bond. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is a bond. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is a bond. In further embodiments, $L_1$ is $C_1$-$C_6$heteroalkyl and $L_2$ is $C_1$-$C_6$alkyl.

In some embodiments is a compound of Formula I wherein X is —S— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula I wherein X is —S—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula I wherein X is —O—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)$N(R_{10})_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —C(=O)$OCH_2SCH_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula I wherein X is —S—, $R_1$ is C(=O)$OR_8$, $R_8$ is $C_1$-$C_6$alkyl, and $L_2$ is a bond. In a further embodiment, $R_2$ is optionally substituted phenyl. In a further embodiment, $R_2$ is optionally substituted heteroaryl. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula I wherein X is —S—, $R_1$ is C(=O)$OR_8$, $R_8$ is $C_1$-$C_6$alkyl, and $L_2$ is $C_1$-$C_6$alkyl. In a further embodiment, $R_2$ is optionally substituted phenyl. In a further embodiment, $R_2$ is optionally substituted heterocycloalkyl. In a further embodiment, $R_2$ is —$OR_9$. In a further embodiment, $R_2$ is —$N(R_9)_2$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula I wherein X is —S—, $L_1$ is a bond, $R_1$ is —$CF_3$, $L_2$ is $C_1$-$C_6$alkyl, $R_2$ is C(=O)$OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In another aspect is a compound of Formula (B):

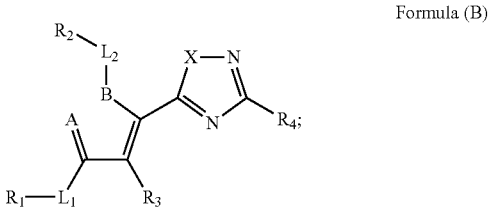

Formula (B)

wherein:
X is —O— or —S—;
A and B are each nitrogen, wherein A and B are bonded together to form a five-membered heteroaryl ring;
$L_1$ and $L_2$ are each independently a bond, $C_1$-$C_6$alkyl, or $C_1$-$C_6$heteroalkyl;
$R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, or —C(=O)$OCH_2SCH_3$;
$R_2$ is —$OR_9$, —$N(R_9)_2$, —C(=O)$R_9$, —C(=O)$OR_9$, —C(=O)$N(R_9)_2$, —$NR_{10}$C(=O)$R_9$, —C(=N—OH)$R_9$, —C(=S)$N(R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$; each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)N($R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

or a pharmaceutically acceptable salt, pharmaceutically acceptable solvate, or pharmaceutically acceptable prodrug thereof.

In another aspect is a compound of Formula (II):

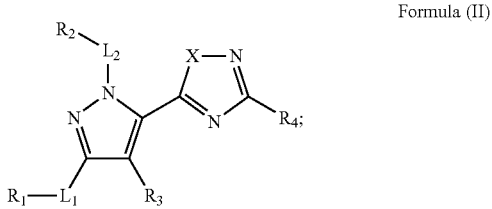

Formula (II)

wherein:

X is —O— or —S—;

$L_1$ and $L_2$ are each independently a bond, $C_1$-$C_6$alkyl, or $C_1$-$C_6$heteroalkyl;

$R_1$ is hydrogen, halogen, —$CF_3$, —$OR_8$, —$N(R_8)_2$, —C(=O)$R_8$, —C(=O)$OR_8$, —C(=O)N($R_8)_2$, —C(=N—OH)$R_8$, —C(=S)N($R_8)_2$, or —C(=O)$OCH_2SCH_3$;

$R_2$ is —$OR_9$, —$N(R_9)_2$, —C(=O)$R_9$, —C(=O)$OR_9$, —C(=O)N($R_9)_2$, —$NR_{10}$C(=O)$R_9$, —C(=N—OH)$R_9$, —C(=S)N($R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_5$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)N($R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

or a pharmaceutically acceptable salt, pharmaceutically acceptable solvate, or pharmaceutically acceptable prodrug thereof.

In some embodiments is a compound of Formula II wherein X is —O—. In further embodiments, $R_1$ is hydrogen, halogen, —$CF_3$, —$OR_8$, —$N(R_8)_2$, —C(=O)$R_8$, —C(=O)$OR_8$, —C(=O)N($R_8)_2$, —C(=N—OH)$R_8$, —C(=S)N($R_8)_2$, or —C(=O)$OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —C(=O)$R_8$. In some embodiments, $R_1$ is —C(=O)$OR_8$. In some embodiments, $R_1$ is —C(=O)N($R_8)_2$. In some embodiments, $R_1$ is —C(=N—OH)$R_8$. In some embodiments, $R_1$ is —C(=S)N($R_8)_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —C(=O)$OCH_2SCH_3$.

In some embodiments is a compound of Formula II wherein X is —O— and $R_2$ is —$OR_9$, —$N(R_9)_2$, —C(=O)$R_9$, —C(=O)$OR_9$, —C(=O)N($R_9)_2$, —$NR_{10}$C(=O)$R_9$, —C(=N—OH)$R_9$, —C(=S)N($R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl. In some embodiments, $R_2$ is —$OR_9$. In some embodiments, $R_2$ is —$N(R_9)_2$. In some embodiments, $R_2$ is —C(=O)$R_9$. In some embodiments, $R_2$ is —C(=O)$OR_9$. In some embodiments, $R_2$ is —C(=O)N($R_9)_2$. In some embodiments, $R_2$ is —$NR_{10}$C(=O)$R_9$. In some embodiments, $R_2$ is —C(=N—OH)$R_9$. In some embodiments, $R_2$ is —C(=S)N($R_9)_2$. In some embodiments, $R_2$ is —C(=O)$OCH_2SCH_3$. In some embodiments, $R_2$ is $C_1$-$C_6$alkyl. In some embodiments, $R_2$ is $C_3$-$C_8$cycloalkyl. In some embodiments, $R_2$ is $C_1$-$C_6$haloalkyl. In some embodiments, $R_2$ is $C_1$-$C_6$heteroalkyl. In some embodiments, $R_2$ is optionally substituted heterocycloalkyl. In some embodiments, $R_2$ is optionally substituted aryl. In some embodiments, $R_2$ is optionally substituted heteroaryl. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula II wherein X is —O— and $L_1$ and $L_2$ are each independently a bond, $C_1$-$C_6$alkyl, or $C_1$-$C_6$heteroalkyl. In further embodiments, $L_1$ and $L_2$ are each a bond. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is a bond. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is a bond. In further embodiments, $L_1$ is $C_1$-$C_6$heteroalkyl and $L_2$ is $C_1$-$C_6$alkyl.

In some embodiments is a compound of Formula II wherein X is —O— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula II wherein X is —O—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula II wherein X is —O—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)$N(R_{10})_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —C(=O)$OCH_2SCH_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula II wherein X is —O—, $R_1$ is C(=O)$OR_8$, $R_8$ is $C_1$-$C_6$alkyl, and $L_2$ is a bond. In a further embodiment, $R_2$ is optionally substituted phenyl. In a further embodiment, $R_2$ is optionally substituted heteroaryl. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula II wherein X is —O—, $R_1$ is C(=O)$OR_8$, $R_8$ is $C_1$-$C_6$alkyl, and $L_2$ is $C_1$-$C_6$alkyl. In a further embodiment, $R_2$ is optionally substituted phenyl. In a further embodiment, $R_2$ is optionally substituted heterocycloalkyl. In a further embodiment, $R_2$ is —$OR_9$. In a further embodiment, $R_2$ is —$N(R_9)_2$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula II wherein X is —O—, $L_1$ is a bond, $R_1$ is —$CF_3$, $L_2$ is $C_1$-$C_6$alkyl, $R_2$ is C(=O)$OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In some embodiments is a compound of Formula II wherein X is —S—. In further embodiments, $R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, or —C(=O)$OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —C(=O)$R_8$. In some embodiments, $R_1$ is —C(=O)$OR_8$. In some embodiments, $R_1$ is —C(=O)$N(R_8)_2$. In some embodiments, $R_1$ is —C(=N—OH)$R_8$. In some embodiments, $R_1$ is —C(=S)$N(R_8)_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —C(=O)$OCH_2SCH_3$.

In some embodiments is a compound of Formula II wherein X is —S— and $R_2$ is —$OR_9$, —$N(R_9)_2$, —C(=O)$R_9$, —C(=O)$OR_9$, —C(=O)$N(R_9)_2$, —$NR_{10}$C(=O)$R_9$, —C(=N—OH)$R_9$, —C(=S)$N(R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl. In some embodiments, $R_2$ is —$OR_9$. In some embodiments, $R_2$ is —$N(R_9)_2$. In some embodiments, $R_2$ is —C(=O)$R_9$. In some embodiments, $R_2$ is —C(=O)$OR_9$. In some embodiments, $R_2$ is —C(=O)$N(R_9)_2$. In some embodiments, $R_2$ is —$NR_{10}$C(=O)$R_9$. In some embodiments, $R_2$ is —C(=O)$OCH_2SCH_3$. In some embodiments, $R_2$ is —C(=S)$N(R_9)_2$. In some embodiments, $R_2$ is —C(=S)$N(R_9)_2$. In some embodiments, $R_2$ is $C_1$-$C_6$alkyl. In some embodiments, $R_2$ is $C_3$-$C_8$cycloalkyl. In some embodiments, $R_2$ is $C_1$-$C_6$haloalkyl. In some embodiments, $R_2$ is $C_1$-$C_6$heteroalkyl. In some embodiments, $R_2$ is optionally substituted heterocycloalkyl. In some embodiments, $R_2$ is optionally substituted aryl. In some embodiments, $R_2$ is optionally substituted heteroaryl. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula II wherein X is —S— and $L_1$ and $L_2$ are each independently a bond, $C_1$-$C_6$alkyl, or $C_1$-$C_6$heteroalkyl. In further embodiments, $L_1$ and $L_2$ are each a bond. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is a bond. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is a bond. In further embodiments, $L_1$ is $C_1$-$C_6$heteroalkyl and $L_2$ is $C_1$-$C_6$alkyl.

In some embodiments is a compound of Formula II wherein X is —S— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula II wherein X is —S—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula II wherein X is —O—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)$N(R_{10})_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —C(=O)$OCH_2SCH_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula II wherein X is —S—, $R_1$ is C(=O)$OR_8$, $R_8$ is $C_1$-$C_6$alkyl, and $L_2$ is a bond. In a further embodiment, $R_2$ is optionally substituted phenyl. In a further embodiment, $R_2$ is optionally substituted heterocycloalkyl. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_1$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula II wherein X is —S—, $R_1$ is C(=O)$OR_8$, $R_8$ is $C_1$-$C_6$alkyl, and $L_2$ is $C_1$-$C_6$alkyl. In a further embodiment, $R_2$ is optionally substituted phenyl. In a further embodiment, $R_2$ is optionally substituted heterocycloalkyl. In a further embodiment, $R_2$ is —$OR_9$. In a further embodiment, $R_2$ is —$N(R_9)_2$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula II wherein X is —S—, $L_1$ is a bond, $R_1$ is —$CF_3$, $L_2$ is $C_1$-$C_6$alkyl, $R_2$ is C(=O)$OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In another aspect is a compound of Formula (C):

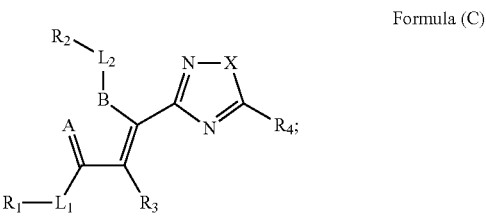

Formula (C)

wherein:
X is —O— or —S—;
A and B are each nitrogen, wherein A and B are bonded together to form a five-membered heteroaryl ring;
$L_1$ and $L_2$ are each independently a bond, $C_1$-$C_6$alkyl, or $C_1$-$C_6$heteroalkyl;
$R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, or —C(=O)$OCH_2SCH_3$;
$R_2$ is —$OR_9$, —$N(R_9)_2$, —C(=O)$R_9$, —C(=O)$OR_9$, —C(=O)$N(R_9)_2$, —$NR_{10}$C(=O)$R_9$, —C(=N—OH)$R_9$, —C(=S)$N(R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

or a pharmaceutically acceptable salt, pharmaceutically acceptable solvate, or pharmaceutically acceptable prodrug thereof.

In another aspect is a compound of Formula (III):

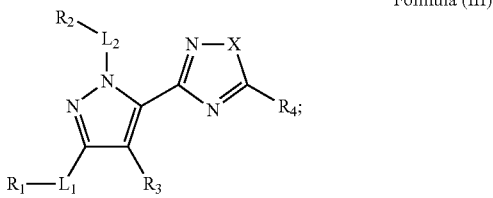

Formula (III)

wherein:

X is —O— or —S—;

$L_1$ and $L_2$ are each independently a bond, $C_1$-$C_6$alkyl, or $C_1$-$C_6$heteroalkyl;

$R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, or —C(=O)$OCH_2SCH_3$;

$R_2$ is —$OR_9$, —$N(R_9)_2$, —C(=O)$R_9$, —C(=O)$OR_9$, —C(=O)$N(R_9)_2$, —$NR_{10}$C(=O)$R_9$, —C(=N—OH)$R_9$, —C(=S)$N(R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

or a pharmaceutically acceptable salt, pharmaceutically acceptable solvate, or pharmaceutically acceptable prodrug thereof In some embodiments is a compound of Formula III wherein X is —O—. In further embodiments, $R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, or —C(=O)$OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —C(=O)$R_8$. In some embodiments, $R_1$ is —C(=O)$OR_8$. In some embodiments, $R_1$ is —C(=O)$N(R_8)_2$. In some embodiments, $R_1$ is —C(=N—OH)$R_8$. In some embodiments, $R_1$ is —C(=S)$N(R_8)_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —C(=O)$OCH_2SCH_3$.

In some embodiments is a compound of Formula III wherein X is —O— and $R_2$ is —$OR_9$, —$N(R_9)_2$, —C(=O)$R_9$, —C(=O)$OR_9$, —C(=O)$N(R_9)_2$, —$NR_{10}$C(=O)$R_9$, —C(=N—OH)$R_9$, —C(=S)$N(R_9)_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl. In some embodiments, $R_2$ is —$OR_9$. In some embodiments, $R_2$ is —$N(R_9)_2$. In some embodiments, $R_2$ is —C(=O)$R_9$. In some embodiments, $R_2$ is —C(=O)$OR_9$. In some embodiments, $R_2$ is —C(=O)$N(R_9)_2$. In some embodiments, $R_2$ is —$NR_{10}$C(=O)$R_9$. In some embodiments, $R_2$ is —C(=N—OH)$R_9$. In some embodiments, $R_2$ is —C(=S)$N(R_9)_2$. In some embodiments, $R_2$ is —C(=O)$OCH_2SCH_3$. In some embodiments, $R_2$ is $C_1$-$C_6$alkyl. In some embodiments, $R_2$ is $C_3$-$C_8$cycloalkyl. In some embodiments, $R_2$ is $C_1$-$C_6$haloalkyl. In some embodiments, $R_2$ is $C_1$-$C_6$heteroalkyl. In some embodiments, $R_2$ is optionally substituted heterocycloalkyl. In some embodiments, $R_2$ is optionally substituted aryl. In some embodiments, $R_2$ is optionally substituted heteroaryl. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula III wherein X is —O— and $L_1$ and $L_2$ are each independently a bond, $C_1$-$C_6$alkyl, or $C_1$-$C_6$heteroalkyl. In further embodiments, $L_1$ and $L_2$ are each a bond. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is a bond. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is a bond. In further embodiments, $L_1$ is $C_1$-$C_6$heteroalkyl and $L_2$ is $C_1$-$C_6$alkyl.

In some embodiments is a compound of Formula III wherein X is —O— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula III wherein X is —O—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula III wherein X is —O—, $R_4$ is heteroaryl substituted with at least one $R_{11}$, and each $R_{11}$ is independently —$OR_{10}$, —$N(R_{10})_2$, —CN, —$C(=O)R_{10}$, —$C(=O)OR_{10}$, —$C(=O)N(R_{10})_2$, —$NR_{10}C(=O)R_{10}$, $NR_{10}SO_2R_{10}$, —$SOR_{10}$, —$SO_2R_{10}$, —$SO_2N(R_{10})_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —$C(=O)R_{10}$. In further embodiments, $R_{11}$ is —$C(=O)OR_{10}$. In further embodiments, $R_{11}$ is —$C(=O)N(R_{10})_2$. In further embodiments, $R_{11}$ is —$NR_{10}C(=O)R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —$C(=O)OCH_2SCH_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula III wherein X is —O—, $R_1$ is $C(=O)OR_8$, $R_8$ is $C_1$-$C_6$alkyl, and $L_2$ is a bond. In a further embodiment, $R_2$ is optionally substituted phenyl. In a further embodiment, $R_2$ is optionally substituted heteroaryl. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula III wherein X is —O—, $R_1$ is $C(=O)OR_8$, $R_8$ is $C_1$-$C_6$alkyl, and $L_2$ is $C_1$-$C_6$alkyl. In a further embodiment, $R_2$ is optionally substituted phenyl. In a further embodiment, $R_2$ is optionally substituted heterocycloalkyl. In a further embodiment, $R_2$ is —$OR_9$. In a further embodiment, $R_2$ is —$N(R_9)_2$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula III wherein X is —O—, $L_1$ is a bond, $R_1$ is —$CF_3$, $L_2$ is $C_1$-$C_6$alkyl, $R_2$ is $C(=O)OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In some embodiments is a compound of Formula III wherein X is —S—. In further embodiments, $R_1$ is hydrogen, halogen, —$CF_3$, —$OR_8$, —$N(R_8)_2$, —$C(=O)R_8$, —$C(=O)OR_8$, —$C(=O)N(R_8)_2$, —$C(=N-OH)R_8$, —$C(=S)N(R_8)_2$, or —$C(=O)OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —$C(=O)R_8$. In some embodiments, $R_1$ is —$C(=O)OR_8$. In some embodiments, $R_1$ is —$C(=O)N(R_8)_2$. In some embodiments, $R_1$ is —$C(=N-OH)R_8$. In some embodiments, $R_1$ is —$C(=S)N(R_8)_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —$C(=O)OCH_2SCH_3$.

In some embodiments is a compound of Formula III wherein X is —S— and $R_2$ is —$OR_9$, —$N(R_9)_2$, —$C(=O)R_9$, —$C(=O)OR_9$, —$C(=O)N(R_9)_2$, —$NR_{10}C(=O)R_9$, —$C(=N-OH)R_9$, —$C(=S)N(R_9)_2$, —$C(=O)OCH_2SCH_3$, $C_1$-$C_6$alkyl, $C_3$-$C_8$cycloalkyl, $C_1$-$C_6$haloalkyl, $C_1$-$C_6$heteroalkyl, optionally substituted heterocycloalkyl, optionally substituted aryl, or optionally substituted heteroaryl. In some embodiments, $R_2$ is —$OR_9$. In some embodiments, $R_2$ is —$N(R_9)_2$. In some embodiments, $R_2$ is —$C(=O)R_9$. In some embodiments, $R_2$ is —$C(=O)OR_9$. In some embodiments, $R_2$ is —$C(=O)N(R_9)_2$. In some embodiments, $R_2$ is —$NR_{10}C(=O)R_9$. In some embodiments, $R_2$ is —$C(=N-OH)R_9$. In some embodiments, $R_2$ is —$C(=S)N(R_9)_2$. In some embodiments, $R_2$ is —$C(=O)OCH_2SCH_3$. In some embodiments, $R_2$ is $C_1$-$C_6$alkyl. In some embodiments, $R_2$ is $C_3$-$C_8$cycloalkyl. In some embodiments, $R_2$ is $C_1$-$C_6$haloalkyl. In some embodiments, $R_2$ is $C_1$-$C_6$heteroalkyl. In some embodiments, $R_2$ is optionally substituted heterocycloalkyl. In some embodiments, $R_2$ is optionally substituted aryl. In some embodiments, $R_2$ is optionally substituted heteroaryl. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula III wherein X is —S— and $L_1$ and $L_2$ are each independently a bond, $C_1$-$C_6$alkyl, or $C_1$-$C_6$heteroalkyl. In further embodiments, $L_1$ and $L_2$ are each a bond. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is a bond. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is a bond. In further embodiments, $L_1$ is $C_1$-$C_6$heteroalkyl and $L_2$ is $C_1$-$C_6$alkyl.

In some embodiments is a compound of Formula III wherein X is —S— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula III wherein X is —S—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula III wherein X is —O—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)N($R_{10}$)$_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —C(=O)OCH$_2$SCH$_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula III wherein X is —S—, $R_1$ is C(=O)$R_8$, $R_8$ is $C_1$-$C_6$alkyl, and $L_2$ is a bond. In a further embodiment, $R_2$ is optionally substituted phenyl. In a further embodiment, $R_2$ is optionally substituted heteroaryl. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is CH$_3$.

In another embodiment is a compound of Formula III wherein X is —S—, $R_1$ is C(=O)$R_3$, $R_8$ is $C_1$-$C_6$alkyl, and $L_2$ is $C_1$-$C_6$alkyl. In a further embodiment, $R_2$ is optionally substituted phenyl. In a further embodiment, $R_2$ is optionally substituted heterocycloalkyl. In a further embodiment, $R_2$ is —$OR_9$. In a further embodiment, $R_2$ is —$N(R_9)_2$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is CH$_3$.

In another embodiment is a compound of Formula III wherein X is —S—, $L_1$ is a bond, $R_1$ is —$CF_3$, $L_2$ is $C_1$-$C_6$alkyl, $R_2$ is C(=O)$OR_9$, and $R_9$ is $C_1$-$C_6$alkyl. In a further embodiment, $R_4$ is phenyl substituted with one $R_1$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is CH$_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In another aspect is a compound of Formula (D):

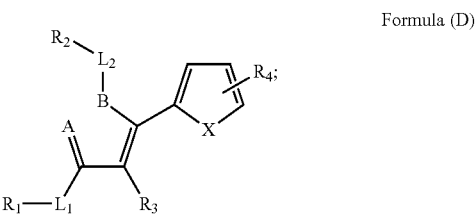

Formula (D)

wherein:

X is —N($R_{12}$)—, or —O—;

A and B are each nitrogen, wherein A and B are bonded together to form a five-membered heteroaryl ring;

$L_1$ is a bond, $C_1$-$C_6$alkyl, or $C_1$-$C_6$heteroalkyl;

$L_2$ is $C_1$-$C_6$alkyl or $C_1$-$C_6$heteroalkyl;

$R_1$ is hydrogen, halogen, —$CF_3$, —$OR_8$, —$N(R_8)_2$, —C(=O)$R_8$, —C(=O)$OR_8$, —C(=O)N($R_8$)$_2$, —C(=N—OH)$R_8$, —C(=S)N($R_8$)$_2$, —C(=CH$_2$)CH$_3$, or —C(=O)OCH$_2$SCH$_3$;

$R_2$ is —C(=O)$OR_9$, —C(=O)N($R_9$)$_2$, —$NR_{10}$C(=O)$R_9$, —C(=N—OH)$R_9$, —C(=S)N($R_9$)$_2$, or —C(=O)OCH$_2$SCH$_3$;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

$R_{12}$ is hydrogen or $C_1$-$C_6$alkyl;

or a pharmaceutically acceptable salt, pharmaceutically acceptable solvate, or pharmaceutically acceptable prodrug thereof.

In another aspect is a compound of Formula (IV):

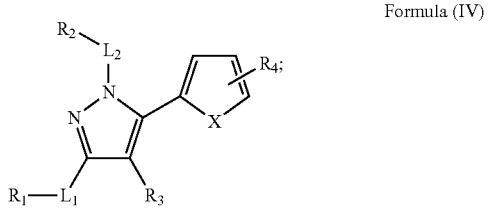

Formula (IV)

wherein:
X is —N($R_{12}$)—, or —O—;
$L_1$ is a bond, $C_1$-$C_6$alkyl, or $C_1$-$C_6$heteroalkyl;
$L_2$ is $C_1$-$C_6$alkyl or $C_1$-$C_6$heteroalkyl;
$R_1$ is hydrogen, halogen, —$CF_3$, —$OR_8$, —N($R_8$)$_2$, —C(=O)$R_8$, —C(=O)$OR_8$, —C(=O)N($R_8$)$_2$, —C(=N—OH)$R_8$, —C(=S)N($R_8$)$_2$, —C(=$CH_2$)$CH_3$, or —C(=O)$OCH_2SCH_3$;
$R_2$ is —C(=O)$OR_9$, —C(=O)N($R_9$)$_2$, —$NR_{10}$C(=O)$R_9$, —C(=N—OH)$R_9$, —C(=S)N($R_9$)$_2$, or —C(=O)$OCH_2SCH_3$;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —$OR_{10}$, —N($R_{10}$)$_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2$N($R_{10}$)$_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
$R_{12}$ is hydrogen or $C_1$-$C_6$alkyl;
or a pharmaceutically acceptable salt, pharmaceutically acceptable solvate, or pharmaceutically acceptable prodrug thereof.

In some embodiments is a compound of Formula IV wherein X is —N($R_{12}$)—. In further embodiments, $R_{12}$ is hydrogen or $C_1$-$C_6$alkyl. In some embodiments, $R_{12}$ is hydrogen. In some embodiments, $R_{12}$ is $C_1$-$C_6$alkyl. In some embodiments, $R_{12}$ is methyl. In further embodiments, $R_1$ is hydrogen, halogen, —$CF_3$, —$OR_8$, —N($R_8$)$_2$, —C(=O)$R_8$, —C(=O)$OR_8$, —C(=O)N($R_8$)$_2$, —C(=N—OH)$R_8$, —C(=S)N($R_8$)$_2$, —C(=$CH_2$)$CH_3$, or —C(=O)$OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —N($R_8$)$_2$. In some embodiments, $R_1$ is —C(=O)$R_8$. In some embodiments, $R_1$ is —C(=O)$OR_8$. In some embodiments, $R_1$ is —C(=O)N($R_8$)$_2$. In some embodiments, $R_1$ is —C(=N—OH)$R_8$. In some embodiments, $R_1$ is —C(=S)N($R_8$)$_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —C(=$CH_2$)$CH_3$. In some embodiments, $R_1$ is —C(=O)$OCH_2SCH_3$.

In some embodiments is a compound of Formula IV wherein X is —N($R_{12}$)— and $R_2$ is —C(=O)$OR_9$, —C(=O)N($R_9$)$_2$, —$NR_{10}$C(=O)$R_9$, —C(=N—OH)$R_9$, —C(=S)N($R_9$)$_2$, or —C(=O)$OCH_2SCH_3$. In some embodiments, $R_2$ is —C(=O)$OR_9$. In some embodiments, $R_2$ is —C(=O)N($R_9$)$_2$. In some embodiments, $R_2$ is —$NR_{10}$C(=O)$R_9$. In some embodiments, $R_2$ is —C(=N—OH)$R_9$. In some embodiments, $R_2$ is —C(=S)N($R_9$)$_2$. In some embodiments, $R_2$ is —C(=O)$OCH_2SCH_3$. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula IV wherein X is —N($R_{12}$)— and $L_1$ is a bond, $C_1$-$C_6$alkyl, or $C_1$-$C_6$heteroalkyl. In some embodiments is a compound of Formula IV wherein X is —N($R_{12}$)— and $L_2$ is $C_1$-$C_6$alkyl, or $C_1$-$C_6$heteroalkyl. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is $C_1$-$C_6$alkyl.

In some embodiments is a compound of Formula IV wherein X is —N($R_{12}$)— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula IV wherein X is —N($R_{12}$)—, $R_4$ is phenyl substituted with at least one $R_{11}$, and each $R_{11}$ is independently —$OR_{10}$, —N($R_{10}$)$_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2$N($R_{10}$)$_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula IV wherein X is —N($R_{12}$)—, $R_4$ is heteroaryl substituted with at least one $R_{11}$, and each $R_{11}$ is independently —$OR_{10}$, —N($R_{10}$)$_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2$N($R_{10}$)$_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —N($R_{10}$)$_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)N($R_{10}$)$_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2$N($R_{10}$)$_2$. In further embodiments, $R_{11}$ is —C(=O)OCH$_2$SCH$_3$. In further embodiments, $R_{11}$ is C$_1$-C$_6$alkyl. In further embodiments, $R_{11}$ is optionally substituted C$_3$-C$_8$cycloalkyl. In further embodiments, $R_{11}$ is C$_1$-C$_6$haloalkyl. In further embodiments, $R_{11}$ is C$_1$-C$_6$heteroalkyl. In further embodiments, $R_{11}$ is —C$_1$-C$_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, C$_1$-C$_6$alkyl, C$_1$-C$_6$heteroalkyl, —C$_1$-C$_6$alkyl-aryl, aryl, or heteroaryl. In some embodiments, $R_{10}$ is hydrogen. In some embodiments, $R_{10}$ is C$_1$-C$_6$alkyl. In some embodiments, $R_{10}$ is C$_1$-C$_6$heteroalkyl. In some embodiments, $R_{10}$ is —C$_1$-C$_6$alkyl-aryl. In some embodiments, $R_{10}$ is aryl. In some embodiments, $R_{10}$ is heteroaryl.

In another embodiment is a compound of Formula IV wherein X is —N($R_{12}$)—, $R_1$ is C(=O)OR$_8$, $R_8$ is C$_1$-C$_6$alkyl, and $L_2$ is C$_1$-C$_6$alkyl. In a further embodiment, $R_2$ is —C(=O)OCH$_2$SCH$_3$. In a further embodiment, $R_2$ is —C(=O)N(R$_9$)$_2$. In a further embodiment, $R_2$ is —C(=O)OR$_9$. In a further embodiment, $L_1$ is a bond. In a further embodiment, $L_1$ is C$_1$-C$_6$alkyl. In yet a further embodiment, $R_4$ is phenyl substituted with one $R_{11}$. In a further embodiment, $R_{11}$ is —SO$_2$R$_{10}$ and $R_{10}$ is C$_1$-C$_6$alkyl. In a further embodiment, $R_{11}$ is —SO$_2$R$_{10}$ and $R_{10}$ is CH$_3$.

In another embodiment is a compound of Formula IV wherein X is —N($R_{12}$)—, $L_1$ is a bond, $R_1$ is —CF$_3$, $L_2$ is C$_1$-C$_6$alkyl, $R_2$ is C(=O)OR$_9$, and $R_9$ is C$_1$-C$_6$alkyl. In a further embodiment, $R_4$ is phenyl substituted with one $R_{11}$. In yet a further embodiment, $R_{11}$ is —SO$_2$R$_{10}$ and $R_{10}$ is C$_1$-C$_6$alkyl. In a further embodiment, $R_{11}$ is —SO$_2$R$_{10}$ and $R_{10}$ is CH$_3$.

In another embodiment is a compound of Formula IV wherein X is —N($R_{12}$)—, $L_1$ is a bond, $R_1$ is —CF$_3$, $L_2$ is C$_1$-C$_6$alkyl, $R_2$ is C(=O)OR$_9$, and $R_9$ is C$_1$-C$_6$heteroalkyl. In a further embodiment, $R_4$ is phenyl substituted with one $R_{11}$. In yet a further embodiment, $R_{11}$ is —SO$_2$R$_{10}$ and $R_{10}$ is C$_1$-C$_6$alkyl. In a further embodiment, $R_{11}$ is —SO$_2$R$_{10}$ and $R_{10}$ is CH$_3$.

In another embodiment is a compound of Formula IV wherein X is —N($R_{12}$)—, $L_1$ is a bond, $R_1$ is —CF$_3$, $L_2$ is C$_1$-C$_6$alkyl, $R_2$ is —C(=O)OCH$_2$SCH$_3$. In a further embodiment, $R_4$ is phenyl substituted with one $R_{11}$. In yet a further embodiment, $R_{11}$ is —SO$_2$R$_{10}$ and $R_{10}$ is C$_1$-C$_6$alkyl. In a further embodiment, $R_{11}$ is —SO$_2$R$_{10}$ and $R_{10}$ is CH$_3$.

In another embodiment of the aforementioned embodiments, $R_3$ is hydrogen, halogen, C$_1$-C$_6$alkyl, or C$_1$-C$_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is C$_1$-C$_6$alkyl. In some embodiments of the aforementioned embodiments, $R_3$ is C$_1$-C$_6$haloalkyl.

In some embodiments is a compound of Formula IV wherein X is —O—. In further embodiments, $R_1$ is hydrogen, halogen, —CF$_3$, —OR$_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$. In some embodiments, $R_1$ is hydrogen. In some embodiments, $R_1$ is halogen. In some embodiments, $R_1$ is —CF$_3$. In some embodiments, $R_1$ is —OR$_8$. In some embodiments, $R_1$ is —N(R$_8$)$_2$. In some embodiments, $R_1$ is —C(=O)R$_8$. In some embodiments, $R_1$ is —C(=O)OR$_8$. In some embodiments, $R_1$ is —C(=O)N(R$_8$)$_2$. In some embodiments, $R_1$ is —C(=N—OH)R$_8$. In some embodiments, $R_1$ is —C(=S)N(R$_8$)$_2$. In further embodiments, $R_8$ is hydrogen, C$_1$-C$_6$alkyl, C$_1$-C$_6$heteroalkyl, —C$_1$-C$_6$alkyl-aryl, aryl, or heteroaryl. In some embodiments, $R_8$ is hydrogen. In some embodiments, $R_8$ is C$_1$-C$_6$alkyl. In some embodiments, $R_8$ is methyl. In some embodiments, $R_8$ is ethyl. In some embodiments, $R_8$ is C$_1$-C$_6$heteroalkyl. In some embodiments, $R_8$ is —C$_1$-C$_6$alkyl-aryl. In some embodiments, $R_8$ is aryl. In some embodiments, $R_8$ is heteroaryl. In some embodiments, $R_1$ is —C(=CH$_2$)CH$_3$. In some embodiments, $R_1$ is —C(=O)OCH$_2$SCH$_3$.

In some embodiments is a compound of Formula IV wherein X is —O— and $R_2$ is —C(=O)OR$_9$, —C(=O)N(R$_9$)$_2$, —NR$_{10}$C(=O)R$_9$, —C(=N—OH)R$_9$, —C(=S)N(R$_9$)$_2$, or —C(=O)OCH$_2$SCH$_3$. In some embodiments, $R_2$ is —C(=O)OR$_9$. In some embodiments, $R_2$ is —C(=O)N(R$_9$)$_2$. In some embodiments, $R_2$ is —NR$_{10}$C(=O)R$_9$. In some embodiments, $R_2$ is —C(=N—OH)R$_9$. In some embodiments, $R_2$ is —C(=S)N(R$_9$)$_2$. In some embodiments, $R_2$ is —C(=O)OCH$_2$SCH$_3$. In further embodiments, $R_9$ is hydrogen, C$_1$-C$_6$alkyl, C$_1$-C$_6$heteroalkyl, —C$_1$-C$_6$alkyl-aryl, aryl, or heteroaryl. In some embodiments, $R_9$ is hydrogen. In some embodiments, $R_9$ is C$_1$-C$_6$alkyl. In some embodiments, $R_9$ is methyl. In some embodiments, $R_9$ is ethyl. In some embodiments, $R_9$ is C$_1$-C$_6$heteroalkyl. In some embodiments, $R_9$ is —C$_1$-C$_6$alkyl-aryl. In some embodiments, $R_9$ is aryl. In some embodiments, $R_9$ is heteroaryl.

In some embodiments is a compound of Formula IV wherein X is —O— and $L_1$ is a bond, C$_1$-C$_6$alkyl, or C$_1$-C$_6$heteroalkyl. In some embodiments is a compound of Formula IV wherein X is —O— and $L_2$ is C$_1$-C$_6$alkyl, or C$_1$-C$_6$heteroalkyl. In further embodiments, $L_1$ is a bond and $L_2$ is C$_1$-C$_6$alkyl. In further embodiments, $L_1$ is a bond and $L_2$ is C$_1$-C$_6$heteroalkyl. In further embodiments, $L_1$ and $L_2$ are each C$_1$-C$_6$alkyl. In further embodiments, $L_1$ is C$_1$-C$_6$alkyl and $L_2$ is C$_1$-C$_6$heteroalkyl. In further embodiments, $L_1$ and $L_2$ are each C$_1$-C$_6$heteroalkyl. In further embodiments, $L_1$ is C$_1$-C$_6$heteroalkyl and $L_2$ is C$_1$-C$_6$alkyl.

In some embodiments is a compound of Formula IV wherein X is —O— and $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula IV wherein X is —O—, $R_4$ is phenyl substituted with at least one $R_{11}$, and each $R_{11}$ is independently —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, NR$_{10}$SO$_2$R$_{10}$, —SOR$_{10}$, —SO$_2$R$_{10}$, —SO$_2$N(R$_{10}$)$_2$, —C(=O)OCH$_2$SCH$_3$, C$_1$-C$_6$alkyl, C$_3$-C$_8$cycloalkyl, C$_1$-C$_6$haloalkyl, C$_1$-C$_6$heteroalkyl, —C$_1$-C$_6$alkyl-aryl, optionally substituted aryl, or optionally substituted heteroaryl. In some embodiments is a compound of Formula IV wherein X is —O—, $R_4$ is heteroaryl substituted with at least one $R_{11}$, and each $R_{11}$ is independently —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, NR$_{10}$SO$_2$R$_{10}$, —SOR$_{10}$, —SO$_2$R$_{10}$, —SO$_2$N(R$_{10}$)$_2$, C$_1$-C$_6$alkyl, C$_3$-C$_8$cycloalkyl, C$_1$-C$_6$haloalkyl, C$_1$-C$_6$heteroalkyl, —C$_1$-C$_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)$N(R_{10})_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_1$ is —C(=O)$OCH_2SCH_3$. In further embodiments, $R_{11}$ is $C_1$-$C_6$alkyl. In further embodiments, $R_1$, is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula IV wherein X is —O—, $R_1$ is C(=O)$OR_8$, $R_8$ is $C_1$-$C_6$alkyl, and $L_2$ is $C_1$-$C_6$alkyl. In a further embodiment, $R_2$ is —C(=O)$OCH_2SCH_3$. In a further embodiment, $R_2$ is —C(=O)$N(R_9)_2$. In a further embodiment, $R_2$ is —C(=O)$OR_9$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula IV wherein X is —O—, $L_1$ is a bond, $R_1$ is —$CF_3$, $L_2$ is $C_1$-$C_6$alkyl, $R_2$ is C(=O)$OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula IV wherein X is —O—, $L_1$ is a bond, $R_1$ is —$CF_3$, $L_2$ is $C_1$-$C_6$alkyl, $R_2$ is C(=O)$OR_9$, and $R_9$ is $C_1$-$C_6$heteroalkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula IV wherein X is —O—, $L_1$ is a bond, $R_1$ is —$CF_3$, $L_2$ is $C_1$-$C_6$alkyl, $R_2$ is —C(=O)$OCH_2SCH_3$. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In another aspect is a compound of Formula (E):

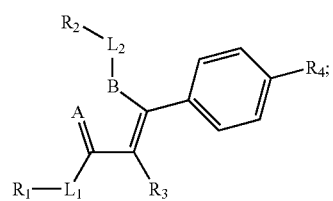

Formula (E)

wherein:
A and B are each nitrogen, wherein A and B are bonded together to form a five-membered heteroaryl ring;
$L_1$ is a bond, $C_1$-$C_6$alkyl, or $C_1$-$C_6$heteroalkyl;
$L_2$ is $C_1$-$C_6$alkyl or $C_1$-$C_6$heteroalkyl;
$R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, —C(=$CH_2$)$CH_3$, or —C(=O)$OCH_2SCH_3$;
$R_2$ is —C(=O)$OR_9$, —C(=O)$N(R_9)_2$, —$NR_{10}$C(=O)$R_9$, —C(=N—OH)$R_9$, —C(=S)$N(R_9)_2$, or —C(=O)$OCH_2SCH_3$;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
or a pharmaceutically acceptable salt, pharmaceutically acceptable solvate, or pharmaceutically acceptable prodrug thereof In another aspect is a compound of Formula (V):

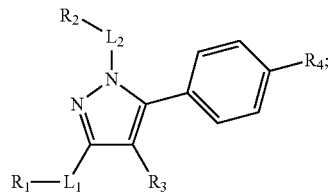

Formula (V)

wherein:
$L_1$ is a bond, $C_1$-$C_6$alkyl, or $C_1$-$C_6$heteroalkyl;
$L_2$ is $C_1$-$C_6$alkyl or $C_1$-$C_6$heteroalkyl;
$R_1$ is hydrogen, halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, —C(=$CH_2$)$CH_3$, or —C(=O)$OCH_2SCH_3$;
$R_2$ is —C(=O)$OR_9$, —C(=O)$N(R_9)_2$, —$NR_{10}$C(=O)$R_9$, —C(=N—OH)$R_9$, —C(=S)$N(R_9)_2$, or —C(=O)$OCH_2SCH_3$;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl; or a pharmaceutically acceptable salt, pharmaceutically acceptable solvate, or pharmaceutically acceptable prodrug thereof.

In some embodiments is a compound of Formula V wherein $R_1$ is hydrogen, halogen, —$CF_3$, —$OR_8$, —$N(R_8)_2$, —C(=O)$R_8$, —C(=O)$OR_8$, —C(=O)N($R_8$)$_2$, —C(=N—OH)$R_8$, —C(=S)N($R_8$)$_2$, —C(=$CH_2$)$CH_3$, or —C(=O)$OCH_2SCH_3$. In some embodiments, $R_1$ is hydrogen. In some embodiments, $R_1$ is halogen. In some embodiments, $R_1$ is —$CF_3$. In some embodiments, $R_1$ is —$OR_8$. In some embodiments, $R_1$ is —$N(R_8)_2$. In some embodiments, $R_1$ is —C(=O)$R_8$. In some embodiments, $R_1$ is —C(=O)$OR_8$. In some embodiments, $R_1$ is —C(=O)N($R_8$)$_2$. In some embodiments, $R_1$ is —C(=N—OH)$R_8$. In some embodiments, $R_1$ is —C(=S)N($R_8$)$_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is —C(=$CH_2$)$CH_3$. In some embodiments, $R_1$ is —C(=O)$OCH_2SCH_3$.

In some embodiments is a compound of Formula V wherein $R_2$ is —C(=O)$OR_9$, —C(=O)N($R_9$)$_2$, —$NR_{10}$C(=O)$R_9$, —C(=N—OH)$R_9$, —C(=S)N($R_9$)$_2$, or —C(=O)$OCH_2SCH_3$. In some embodiments, $R_2$ is —C(=O)$OR_9$. In some embodiments, $R_2$ is —C(=O)N($R_9$)$_2$. In some embodiments, $R_2$ is —$NR_{10}$C(=O)$R_9$. In some embodiments, $R_2$ is —C(=N—OH)$R_9$. In some embodiments, $R_2$ is —C(=S)N($R_9$)$_2$. In some embodiments, $R_2$ is —C(=O)$OCH_2SCH_3$. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl.

In some embodiments is a compound of Formula V wherein $L_1$ is a bond, $C_1$-$C_6$alkyl, or $C_1$-$C_6$heteroalkyl. In some embodiments is a compound of Formula V wherein $L_2$ is $C_1$-$C_6$alkyl, or $C_1$-$C_6$heteroalkyl. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is $C_1$-$C_6$alkyl.

In some embodiments is a compound of Formula V wherein $R_4$ is aryl or heteroaryl; wherein aryl or heteroaryl is substituted with at least one $R_{11}$. In some embodiments, $R_4$ is aryl substituted with one $R_{11}$. In some embodiments, $R_4$ is aryl substituted with two $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula V wherein $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula V wherein $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)N($R_{10}$)$_2$, —$NR_{10}$C(=O)$R_{10}$, $NR_{10}SO_2R_{10}$, —$SOR_{10}$, —$SO_2R_{10}$, —$SO_2N(R_{10})_2$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments, $R_{11}$ is —$OR_{10}$. In further embodiments, $R_{11}$ is —$N(R_{10})_2$. In further embodiments, $R_{11}$ is —CN. In further embodiments, $R_{11}$ is —C(=O)$R_{10}$. In further embodiments, $R_{11}$ is —C(=O)$OR_{10}$. In further embodiments, $R_{11}$ is —C(=O)N($R_{10}$)$_2$. In further embodiments, $R_{11}$ is —$NR_{10}$C(=O)$R_{10}$. In further embodiments, $R_{11}$ is $NR_{10}SO_2R_{10}$. In further embodiments, $R_{11}$ is —$SOR_{10}$. In further embodiments, $R_{11}$ is —$SO_2R_{10}$. In further embodiments, $R_{11}$ is —$SO_2N(R_{10})_2$. In further embodiments, $R_{11}$ is —C(=O)$OCH_2SCH_3$. In further embodiments, $R_{11}$ is $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula V wherein $R_1$ is C(=O)$OR_8$, $R_8$ is $C_1$-$C_6$alkyl, and $L_2$ is $C_1$-$C_6$alkyl. In a further embodiment, $R_2$ is —C(=O)$OCH_2SCH_3$. In a further embodiment, $R_2$ is —C(=O)N($R_9$)$_2$. In a further embodiment, $R_2$ is —C(=O)$OR_9$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula V wherein $L_1$ is a bond, $R_1$ is —$CF_3$, $L_2$ is $C_1$-$C_6$alkyl, $R_2$ is C(=O)$OR_9$, and $R_9$ is $C_1$-$C_6$alkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula V wherein $L_1$ is a bond, $R_1$ is —$CF_3$, $L_2$ is $C_1$-$C_6$alkyl, $R_2$ is C(=O)$OR_9$, and $R_9$ is $C_1$-$C_6$heteroalkyl. In a further embodiment, $R_4$ is phenyl substituted with one $R_{11}$. In yet a further embodiment, $R_{11}$ is —$SO_2R_{10}$ and $R_{10}$ is $C_1$-$C_6$alkyl. In a further embodiment, $R_{11}$ is —$SO_2R_{10}$ and $R_{10}$ is $CH_3$.

In another embodiment is a compound of Formula V wherein $L_1$ is a bond, $R_1$ is —$CF_3$, $L_2$ is $C_1$-$C_6$alkyl, $R_2$ is —C(=O)OCH$_2$SCH$_3$. In a further embodiment, $R_4$ is phenyl substituted with one $R_{11}$. In yet a further embodiment, $R_{11}$ is —SO$_2$R$_{10}$ and $R_{10}$ is $C_1$-$C_6$alkyl. In a further embodiment, $R_{11}$ is —SO$_2$R$_{10}$ and $R_{10}$ is CH$_3$.

In another embodiment of the aforementioned embodiments, $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

In another aspect is a compound of Formula (F):

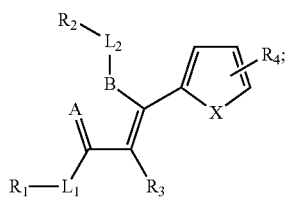

Formula (F)

wherein:
X is —S—;
A and B are each nitrogen, wherein A and B are bonded together to form a five-membered heteroaryl ring;
$L_1$ is a bond, $C_1$-$C_6$alkyl, or $C_1$-$C_6$heteroalkyl;
$L_2$ is $C_1$-$C_6$alkyl or $C_1$-$C_6$heteroalkyl;
$R_1$ is hydrogen, halogen, $C_1$-$C_6$alkyl, $C_2$-$C_6$alkenyl, $C_2$-$C_6$alkynyl, —$CF_3$, —$OR_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$;
$R_2$ is —C(=O)OR$_{13}$, —NR$_{10}$C(=O)R$_9$, —C(=N—OH)R$_9$, —C(=S)N(R$_9$)$_2$, or —C(=O)OCH$_2$SR$_{15}$;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, NR$_{10}$SO$_2$R$_{10}$, —SOR$_{10}$, —SO$_2$R$_{14}$, —SO$_2$N(R$_{10}$)$_2$, —C(=O)OCH$_2$SCH$_3$, optionally substituted $C_1$-$C_6$alkyl, optionally substituted $C_3$-$C_8$cycloalkyl, $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl;
$R_{13}$ is hydrogen, $C_1$-$C_6$alkyl, $C_1$-$C_6$heteroalkyl, —$C_1$-$C_6$alkyl-aryl, aryl, or heteroaryl;
$R_{14}$ is $C_1$-$C_6$alkyl, $C_1$-$C_6$heteroalkyl, —$C_1$-$C_6$alkyl-aryl, aryl, or heteroaryl;
$R_{15}$ is $C_1$-$C_6$alkyl;
or a pharmaceutically acceptable salt, pharmaceutically acceptable solvate, or pharmaceutically acceptable prodrug thereof.

In another aspect is a compound of Formula (VI):

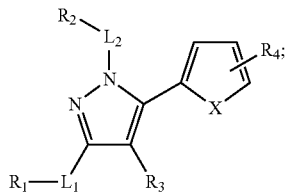

Formula (VI)

wherein:
X is —S—;
$L_1$ is a bond, $C_1$-$C_6$alkyl, or $C_1$-$C_6$heteroalkyl;
$L_2$ is $C_1$-$C_6$alkyl or $C_1$-$C_6$heteroalkyl;
$R_1$ is hydrogen, halogen, $C_1$-$C_6$alkyl, $C_2$-$C_6$alkenyl, $C_2$-$C_6$alkynyl, —$CF_3$, —$OR_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$;
$R_2$ is —C(=O)OR$_{13}$, —NR$_{10}$C(=O)R$_9$, —C(=N—OH)R$_9$, —C(=S)N(R$_9$)$_2$, or —C(=O)OCH$_2$SR$_{15}$;
$R_3$ is hydrogen, halogen, $C_1$-$C_6$alkyl, or $C_1$-$C_6$haloalkyl;
$R_4$ is aryl or heteroaryl; wherein aryl or heteroaryl is substituted with at least one $R_{11}$;
each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;
$R_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, NR$_{10}$SO$_2$R$_{10}$, —SOR$_{10}$, —SO$_2$R$_{14}$, —SO$_2$N(R$_{10}$)$_2$, —C(=O)OCH$_2$SCH$_3$, optionally substituted $C_1$-$C_6$alkyl, optionally substituted $C_3$-$C_8$cycloalkyl, $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl;
$R_{13}$ is hydrogen, $C_1$-$C_6$alkyl, $C_1$-$C_6$heteroalkyl, —$C_1$-$C_6$alkyl-aryl, aryl, or heteroaryl;
$R_{14}$ is $C_1$-$C_6$alkyl, $C_1$-$C_6$heteroalkyl, —$C_1$-$C_6$alkyl-aryl, aryl, or heteroaryl;
$R_{15}$ is $C_1$-$C_6$alkyl;
or a pharmaceutically acceptable salt, pharmaceutically acceptable solvate, or pharmaceutically acceptable prodrug thereof.

In some embodiments is a compound of Formula VI wherein $R_1$ hydrogen, halogen, $C_1$-$C_6$alkyl, $C_2$-$C_6$alkenyl, $C_2$-$C_6$alkynyl, —$CF_3$, —$OR_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$. In further embodiments, $R_1$ is —$CF_3$. In some embodiments is a compound of Formula VI wherein $R_1$ is hydrogen, halogen, $C_1$-$C_6$alkyl, $C_2$-$C_6$alkenyl, $C_2$-$C_6$alkynyl, —$OR_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, —C(=CH$_2$)CH$_3$, or —C(=O)OCH$_2$SCH$_3$. In some embodiments, $R_1$ is hydrogen. In some embodiments, $R_1$ is halogen. In some embodiments, $R_1$ is $C_1$-$C_6$alkyl. In some embodiments, $R_1$ is $C_2$-$C_6$alkenyl. In some embodiments, $R_1$ is $C_2$-$C_6$alkynyl. In some embodiments, $R_1$ is —$OR_8$. In some embodiments, $R_1$ is —N(R$_8$)$_2$. In some embodiments, $R_1$ is —C(=O)R$_8$. In some embodiments, $R_1$ is —C(=O)OR$_8$. In some embodiments, $R_1$ is —C(=O)N(R$_8$)$_2$. In some embodiments, $R_1$ is —C(=N—OH)R$_8$. In some embodiments, $R_1$ is —C(=S)N(R$_8$)$_2$. In further embodiments, $R_8$ is hydrogen, $C_1$-$C_6$alkyl, $C_1$-$C_6$heteroalkyl, —$C_1$-$C_6$alkyl-aryl, aryl, or heteroaryl. In some embodiments, $R_8$ is hydrogen. In some embodiments, $R_8$ is $C_1$-$C_6$alkyl. In some embodiments, $R_8$ is methyl. In some embodiments, $R_8$ is ethyl. In some embodiments, $R_8$ is $C_1$-$C_6$heteroalkyl. In some embodiments, $R_8$ is —$C_1$-$C_6$alkyl-aryl. In some embodiments, $R_8$ is aryl. In some embodiments, $R_8$ is heteroaryl. In some embodiments, $R_1$ is $C_1$-$C_6$alkyl or —C(=$CH_2$)$CH_3$. In some embodiments, $R_1$ is —C(=$CH_2$)$CH_3$. In some embodiments, $R_1$ is —C(=O)O$CH_2$S$CH_3$.

In some embodiments is a compound of Formula VI wherein $R_2$ is —C(=O)O$R_{13}$, —$NR_{10}$C(=O)$R_9$, —C(=N—OH)$R_9$, —C(=S)N($R_9$)$_2$, or —C(=O)OCH$_2$S$R_{15}$. In some embodiments, $R_2$ is —$NR_{10}$C(=O)$R_9$. In some embodiments, $R_2$ is —C(=N—OH)$R_9$. In some embodiments, $R_2$ is —C(=S)N($R_9$)$_2$. In further embodiments, $R_9$ is hydrogen, $C_1$-$C_6$alkyl, $C_1$-$C_6$heteroalkyl, —$C_1$-$C_6$alkyl-aryl, aryl, or heteroaryl. In some embodiments, $R_9$ is hydrogen. In some embodiments, $R_9$ is $C_1$-$C_6$alkyl. In some embodiments, $R_9$ is methyl. In some embodiments, $R_9$ is ethyl. In some embodiments, $R_9$ is $C_1$-$C_6$heteroalkyl. In some embodiments, $R_9$ is —$C_1$-$C_6$alkyl-aryl. In some embodiments, $R_9$ is aryl. In some embodiments, $R_9$ is heteroaryl. In some embodiments, $R_2$ is —C(=O)O$R_{13}$. In further embodiments, $R_{13}$ is hydrogen, $C_1$-$C_6$alkyl, $C_1$-$C_6$heteroalkyl, —$C_1$-$C_6$alkyl-aryl, aryl, or heteroaryl. In some embodiments, $R_3$ is hydrogen. In some embodiments, $R_{13}$ is $C_1$-$C_6$alkyl. In some embodiments, $R_{13}$ is methyl. In some embodiments, $R_{13}$ is ethyl. In some embodiments, $R_{13}$ is $C_1$-$C_6$heteroalkyl. In some embodiments, $R_{13}$ is —$C_1$-$C_6$alkyl-aryl. In some embodiments, $R_{13}$ is aryl. In some embodiments, $R_{13}$ is heteroaryl. In some embodiments, $R_2$ is —C(=O)OCH$_2$S$R_{15}$. In further embodiments, $R_{15}$ is $C_1$-$C_6$alkyl. In some embodiments, $R_{15}$ is methyl. In some embodiments, $R_{15}$ is ethyl.

In some some embodiments is a compound of Formula VI wherein $R_2$ is —C(=O)O$R_{13}$ and $R_{13}$ is $C_2$-$C_6$alkyl, $C_1$-$C_6$heteroalkyl, —$C_1$-$C_6$alkyl-aryl, aryl, or heteroaryl. In some embodiments, $R_{13}$ is $C_2$-$C_6$alkyl or $C_1$-$C_6$heteroalkyl. In some embodiments, $R_{13}$ is $C_2$-$C_6$alkyl. In some embodiments, $R_{13}$ is ethyl. In some embodiments, $R_{13}$ is $C_1$-$C_6$heteroalkyl. In some embodiments, $R_{13}$ is —$C_1$-$C_6$alkyl-aryl. In some embodiments, $R_{13}$ is aryl. In some embodiments, $R_{13}$ is heteroaryl.

In some embodiments is a compound of Formula VI wherein $L_1$ is a bond, $C_1$-$C_6$alkyl, or $C_1$-$C_6$heteroalkyl. In some embodiments is a compound of Formula VI wherein $L_2$ is $C_1$-$C_6$alkyl, or $C_1$-$C_6$heteroalkyl. In further embodiments, $L_1$ is a bond and $L_2$ is $C_1$-$C_6$alkyl. In further embodiments, $L_1$ is a bond and $L_2$ is $C_1$-$C_6$heteroalkyl. In further embodiments, $L_1$ and $L_2$ are each $C_1$-$C_6$alkyl. In further embodiments, $L_1$ is $C_1$-$C_6$alkyl and $L_2$ is $C_1$-$C_6$heteroalkyl. In further embodiments, $L_1$ and $L_2$ are each $C_1$-$C_6$heteroalkyl. In further embodiments, $L_1$ is $C_1$-$C_6$heteroalkyl and $L_2$ is $C_1$-$C_6$alkyl.

In some embodiments is a compound of Formula VI wherein $R_4$ is aryl or heteroaryl; wherein aryl or heteroaryl is substituted with at least one $R_{11}$. In some embodiments, $R_4$ is substituted with one $R_{11}$. In some embodiments, $R_4$ is aryl substituted with one $R_{11}$. In some embodiments is a compound of Formula VI wherein $R_4$ is substituted with at least two $R_{11}$. In some embodiments, $R_4$ is aryl substituted with two $R_{11}$. In some embodiments, $R_4$ is substituted with three $R_{11}$. In some embodiments, $R_4$ is aryl substituted with three $R_{11}$. In further embodiments, $R_4$ is phenyl substituted with one $R_{11}$. In further embodiments, $R_4$ is phenyl substituted with two $R_{11}$. In further embodiments, $R_4$ is phenyl substituted with three $R_{11}$. In some embodiments, $R_4$ is heteroaryl substituted with one $R_{11}$. In some embodiments, $R_4$ is heteroaryl substituted with two $R_{11}$. In some embodiments, $R_4$ is heteroaryl substituted with three $R_{11}$.

In some embodiments is a compound of Formula VI wherein $R_4$ is phenyl substituted with at least one $R_{11}$, and each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —$NR_{10}$C(=O)$R_{10}$, $NR_{10}$SO$_2$$R_{10}$, —SO$R_{10}$, —SO$_2$$R_{14}$, —SO$_2$N($R_{10}$)$_2$, —C(=O)OCH$_2$S$CH_3$, optionally substituted $C_1$-$C_6$alkyl, optionally substituted $C_3$-$C_8$cycloalkyl, $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl. In some embodiments is a compound of Formula VI wherein $R_4$ is heteroaryl substituted with at least one $R_{11}$, and each $R_{11}$ is independently independently halogen, nitro, —O$R_{10}$, —N($R_{10}$)$_2$, —CN, —C(=O)$R_{10}$, —C(=O)O$R_{10}$, —C(=O)N($R_{10}$)$_2$, —$NR_{10}$C(=O)$R_{10}$, $NR_{10}$SO$_2$$R_{10}$, —SO$R_{10}$, —SO$_2$$R_{14}$, —SO$_2$N($R_{10}$)$_2$, —C(=O)OCH$_2$S$CH_3$, optionally substituted $C_1$-$C_6$alkyl, optionally substituted $C_3$-$C_8$cycloalkyl, $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl. In further embodiments, $R_{11}$ is halogen. In further embodiments, $R_{11}$ is nitro. In further embodiments, $R_{11}$ is —O$R_{10}$. In further embodiments, $R_{11}$ is —N($R_{10}$)$_2$. In further embodiments, $R_{11}$ is —CN. In further embodiments, $R_{11}$ is —C(=O)$R_{10}$. In further embodiments, $R_{11}$ is —C(=O)O$R_{10}$. In further embodiments, $R_{11}$ is —C(=O)N($R_{10}$)$_2$. In further embodiments, $R_{11}$ is —$NR_{10}$C(=O)$R_{10}$. In further embodiments, $R_{11}$ is $NR_{10}$SO$_2$$R_{10}$. In further embodiments, $R_{11}$ is —SO$R_{10}$. In further embodiments, $R_{11}$ is —SO$_2$$R_{14}$. In further embodiments, $R_{11}$ is —SO$_2$N($R_{10}$)$_2$. In further embodiments, $R_{11}$ is —C(=O)OCH$_2$S$CH_3$. In further embodiments, $R_{11}$ is optionally substituted $C_1$-$C_6$alkyl. In further embodiments, $R_{11}$ is optionally substituted $C_3$-$C_8$cycloalkyl. In further embodiments, $R_{11}$ is $C_1$-$C_6$haloalkyl. In further embodiments, $R_{11}$ is $C_1$-$C_6$heteroalkyl. In further embodiments, $R_{11}$ is —$C_1$-$C_6$alkyl-aryl. In further embodiments, $R_{11}$ is optionally substituted aryl. In further embodiments, $R_{11}$ is optionally substituted heteroaryl. In yet further embodiments, each $R_{14}$ is independently $C_1$-$C_6$alkyl, $C_1$-$C_6$heteroalkyl, —$C_1$-$C_6$alkyl-aryl, aryl, or heteroaryl. In some embodiments, $R_{14}$ is $C_1$-$C_6$alkyl. In further embodiments, $R_{14}$ is methyl. In further embodiments, $R_{14}$ is ethyl. In some embodiments, $R_{14}$ is $C_1$-$C_6$heteroalkyl. In some embodiments, $R_{14}$ is —$C_1$-$C_6$alkyl-aryl. In some embodiments, $R_{14}$ is aryl. In some embodiments, $R_{14}$ is heteroaryl. In yet further embodiments, each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments, $R_{10}$ is hydrogen. In some embodiments, $R_{10}$ is $C_1$-$C_6$alkyl. In some embodiments, $R_{10}$ is $C_1$-$C_6$heteroalkyl. In some embodiments, $R_{10}$ is —$C_1$-$C_6$alkyl-aryl. In some embodiments, $R_{10}$ is aryl. In some embodiments, $R_{10}$ is heteroaryl.

In another embodiment is a compound of Formula VI wherein $R_4$ is substituted with at least two $R_{11}$ and $R_{11}$ is independently halogen, —SO$_2$$R_{14}$, $NR_{10}$SO$_2$$R_{10}$, or —SO$_2$N($R_{10}$)$_2$. In another embodiment is a compound of Formula VI wherein $R_4$ is substituted with one $R_{11}$ and $R_{11}$ is —SO$_2$$R_{14}$. In another embodiment is a compound of Formula VI wherein $R_4$ is substituted with at one $R_{11}$, $R_{11}$ is —SO$_2$$R_{14}$, and $R_{14}$ is $C_2$-$C_6$alkyl, $C_1$-$C_6$heteroalkyl, —$C_1$-$C_6$alkyl-aryl, aryl, or heteroaryl. In another embodiment is a compound of Formula VI wherein $R_4$ is substituted with at one $R_{11}$, $R_{11}$ is —SO$_2$$R_{14}$, and $R_{14}$ is $C_2$-$C_6$alkyl. In another embodiment is a compound of Formula VI wherein $R_4$ is phenyl substituted with at one $R_{11}$ and $R_{11}$ is $—SO_2R_{14}$. In another embodiment is a compound of Formula VI wherein $R_4$ is phenyl substituted with at one $R_{11}$, $R_{11}$ is $—SO_2R_{14}$, and $R_{14}$ is $C_2$-$C_6$alkyl, $C_1$-$C_6$heteroalkyl, $—C_1$-$C_6$alkyl-aryl, aryl, or heteroaryl. In another embodiment is a compound of Formula VI wherein $R_4$ is phenyl substituted with at one $R_{11}$, $R_{11}$ is $—SO_2R_{14}$, and $R_{14}$ is $C_2$-$C_6$alkyl.

In another embodiment is a compound of Formula VI wherein $R_1$ is $C(=O)OR_8$, $R_8$ is $C_1$-$C_6$alkyl, and $L_2$ is $C_1$-$C_6$alkyl. In a further embodiment, $R_2$ is $—C(=O)OCH_2SCH_3$. In a further embodiment, $R_2$ is $—C(=O)OR_{13}$. In a further embodiment, $L_1$ is a bond. In a further embodiment, $L_1$ is $C_1$-$C_6$alkyl. In yet a further embodiment, $R_4$ is phenyl substituted with one $R_{11}$. In a further embodiment, $R_{11}$ is $—SO_2R_{10}$ and $R_{10}$ is $C_1$-$C_6$alkyl. In a further embodiment, $R_{11}$ is $—SO_2R_{10}$ and $R_{10}$ is $CH_3$.

In another embodiment is a compound of Formula VI wherein $L_1$ is a bond, $R_1$ is $—CF_3$, $L_2$ is $C_1$-$C_6$alkyl, $R_2$ is $C(=O)OR_9$, and $R_9$ is $C_2$-$C_6$alkyl. In a further embodiment, $R_4$ is phenyl substituted with one $R_{11}$. In yet a further embodiment, $R_{11}$ is $—SO_2R_{10}$ and $R_{10}$ is $C_1$-$C_6$alkyl. In a further embodiment, $R_{11}$ is $—SO_2R_{10}$ and $R_{10}$ is $CH_3$.

In another embodiment is a compound of Formula VI wherein $L_1$ is a bond, $R_1$ is $—CF_3$, $L_2$ is $C_1$-$C_6$alkyl, $R_2$ is $C(=O)OR_9$, and $R_9$ is $C_1$-$C_6$heteroalkyl. In a further embodiment, $R_4$ is phenyl substituted with one $R_{11}$. In yet a further embodiment, $R_{11}$ is $—SO_2R_{10}$ and $R_{10}$ is $C_1$-$C_6$alkyl. In a further embodiment, $R_{11}$ is $—SO_2R_{10}$ and $R_{10}$ is $CH_3$.

In another embodiment is a compound of Formula VI wherein $L_1$ is a bond, $R_1$ is $—CF_3$, $L_2$ is $C_1$-$C_6$alkyl, $R_2$ is $—C(=O)OCH_2SCH_3$. In a further embodiment, $R_4$ is phenyl substituted with one $R_{11}$. In yet a further embodiment, $R_{11}$ is $—SO_2R_{10}$ and $R_{10}$ is $C_1$-$C_6$alkyl. In a further embodiment, $R_{11}$ is $—SO_2R_{10}$ and $R_{10}$ is $CH_3$.

In another embodiment of the aforementioned embodiments of Formula VI is a compound wherein $R_3$ is hydrogen, halogen, $C_1$-$C_6$alkyl, or $C_1$-$C_6$haloalkyl. In some embodiments of the aforementioned embodiments, $R_3$ is hydrogen. In some embodiments of the aforementioned embodiments, $R_3$ is halogen. In some embodiments of the aforementioned embodiments, $R_3$ is $C_1$-$C_6$alkyl. In some embodiments of the aforementioned embodiments, $R_3$ is $C_1$-$C_6$haloalkyl.

Any combination of the groups described above for the various variables is contemplated herein. Throughout the specification, groups and substituents thereof can be chosen by one skilled in the field to provide stable moieties and compounds.

In some embodiments is a compound selected from:

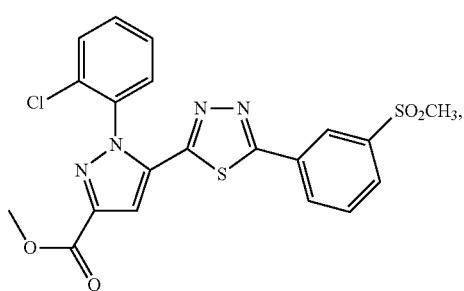

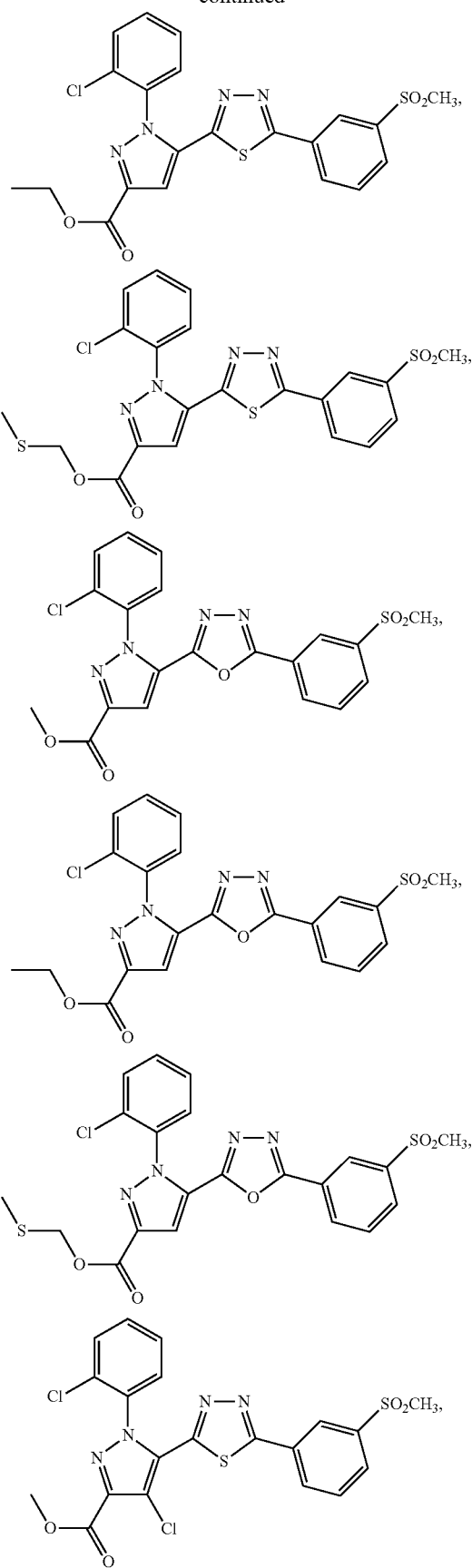

45
-continued
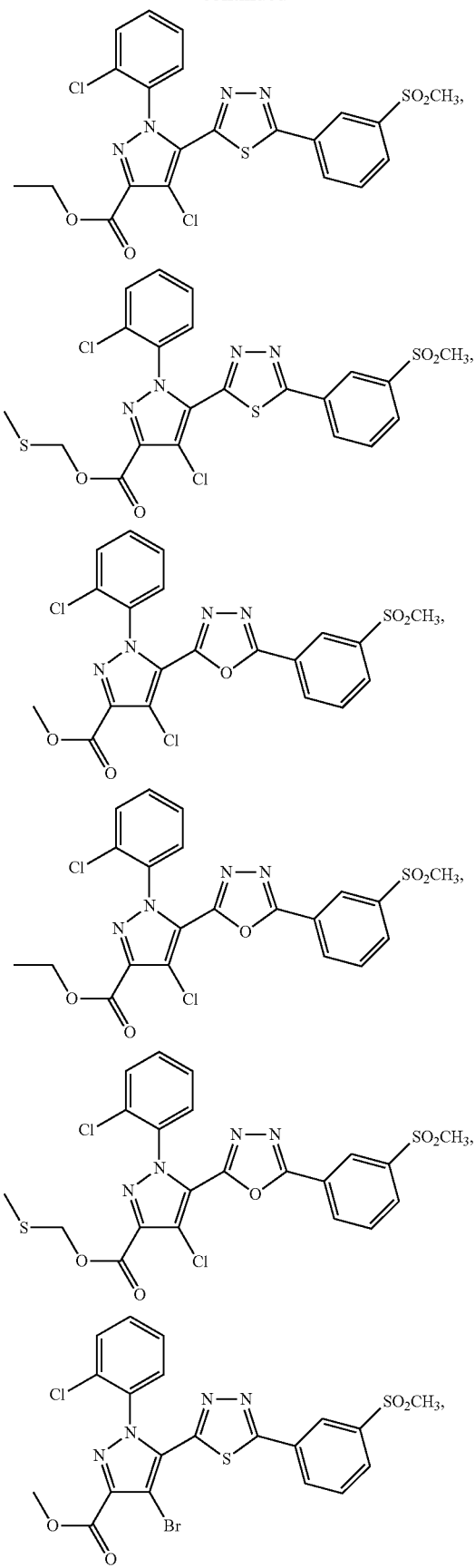
46
-continued
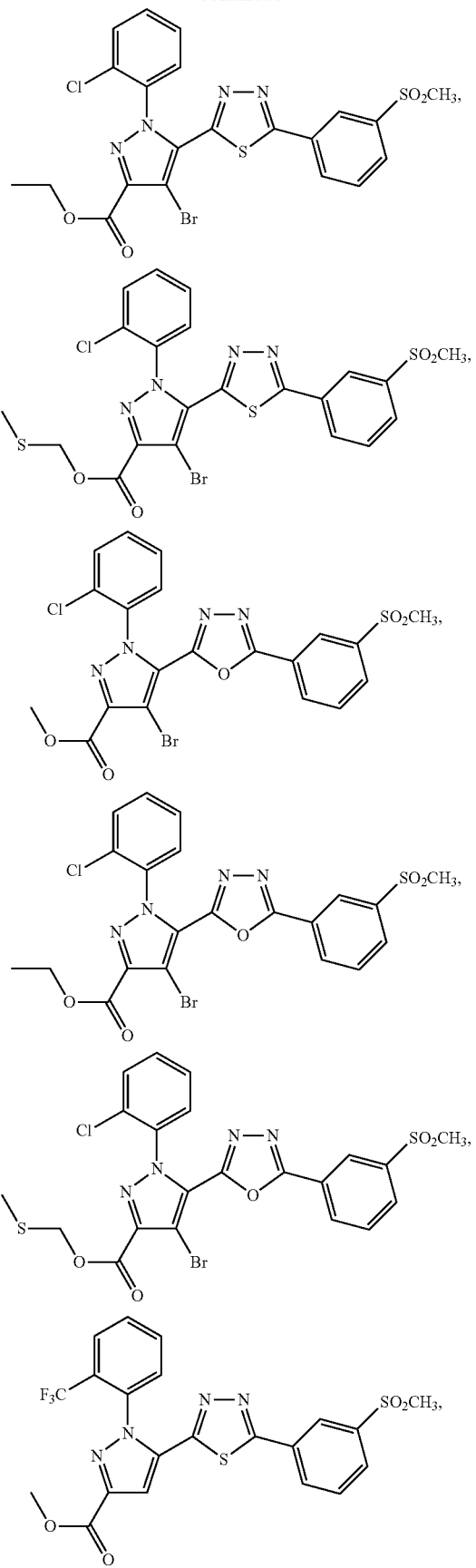

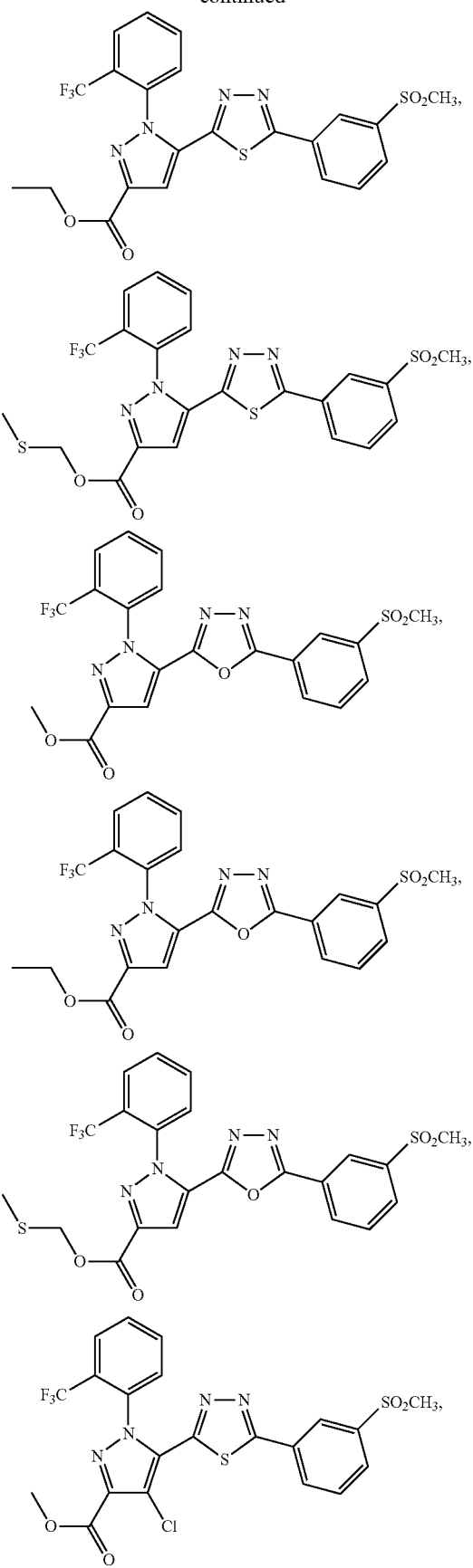
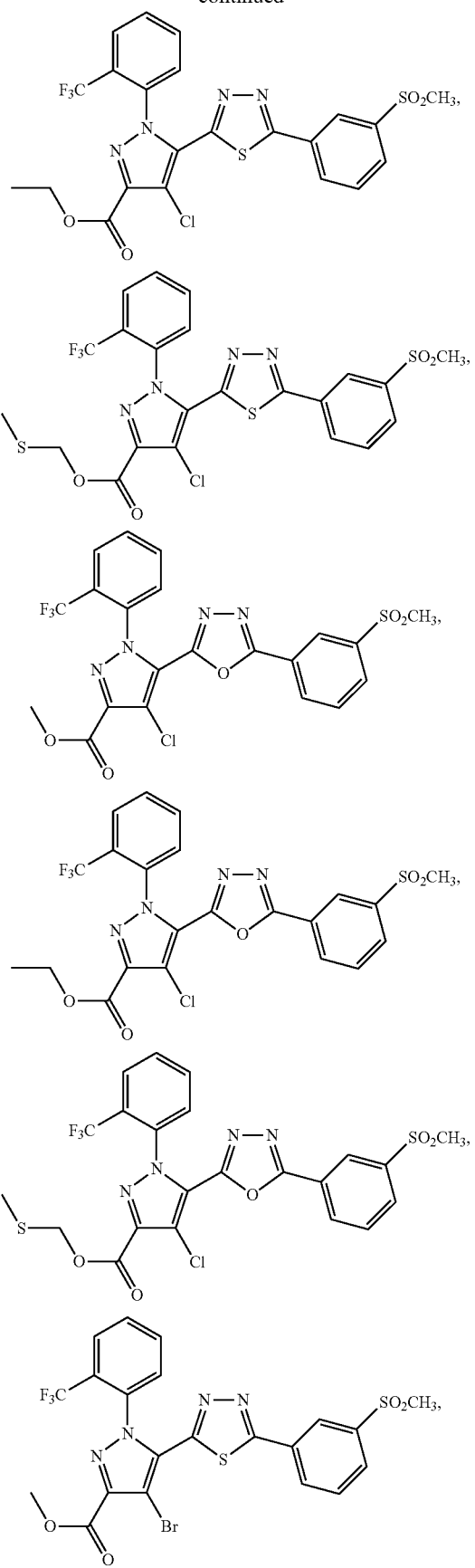

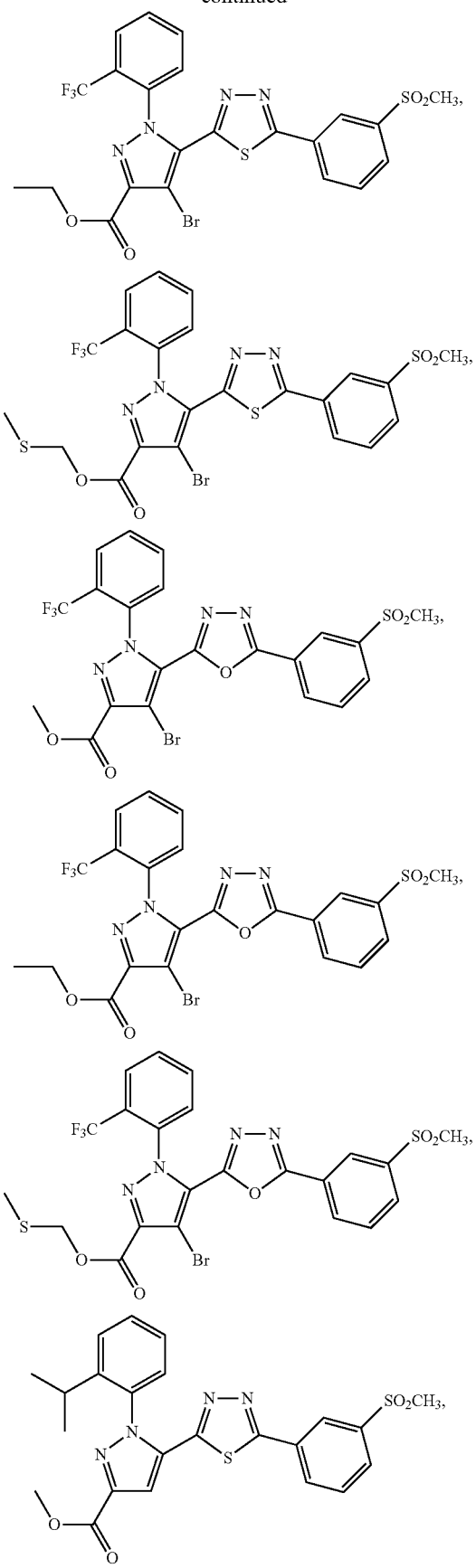
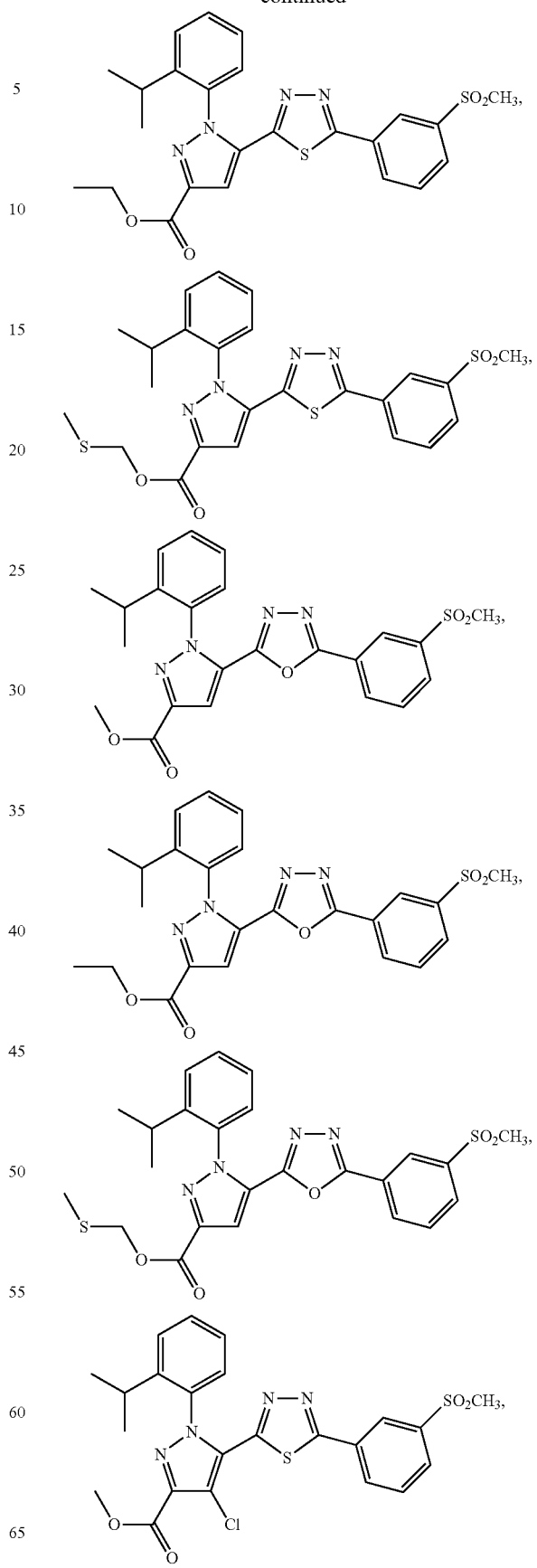

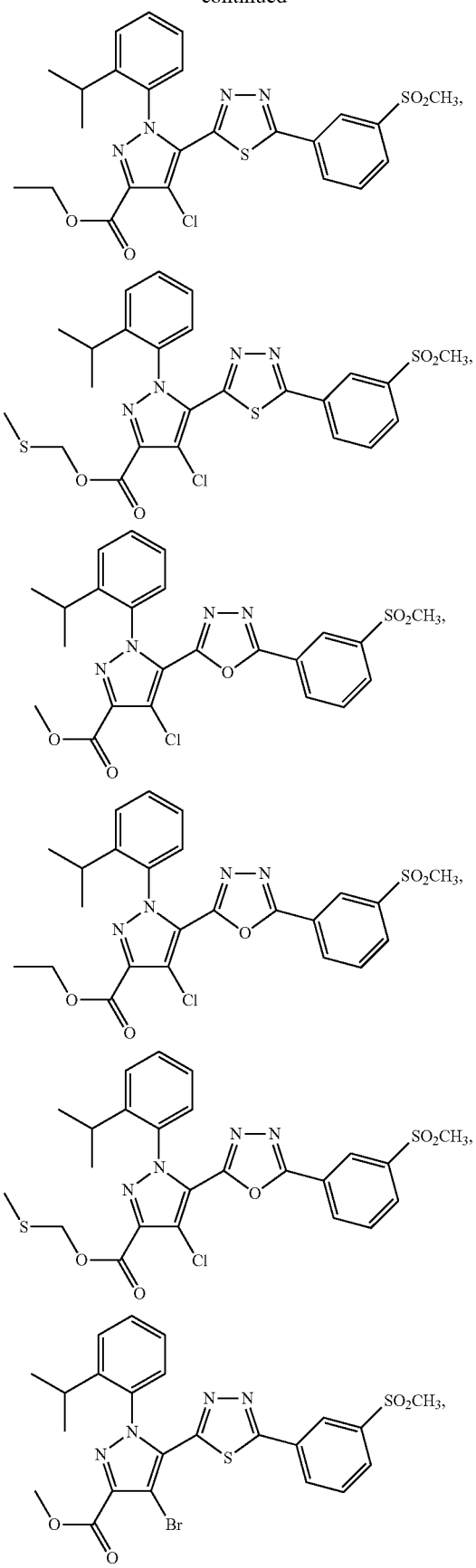
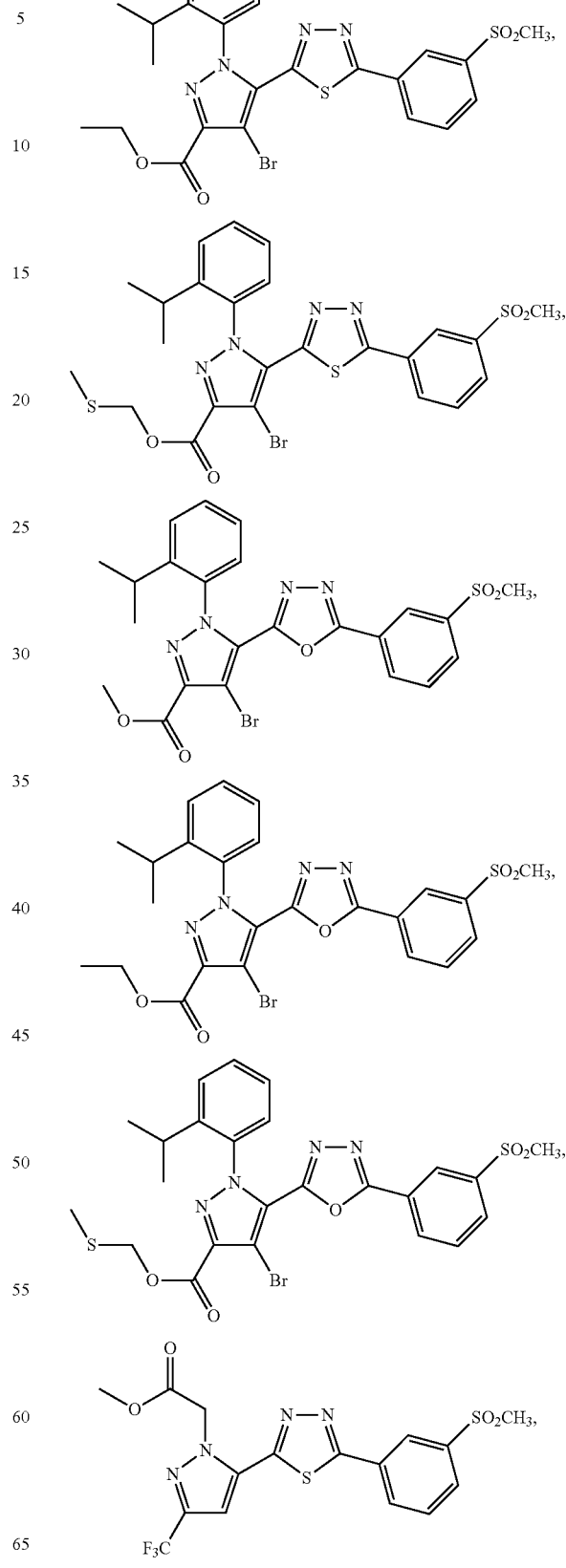

53
-continued
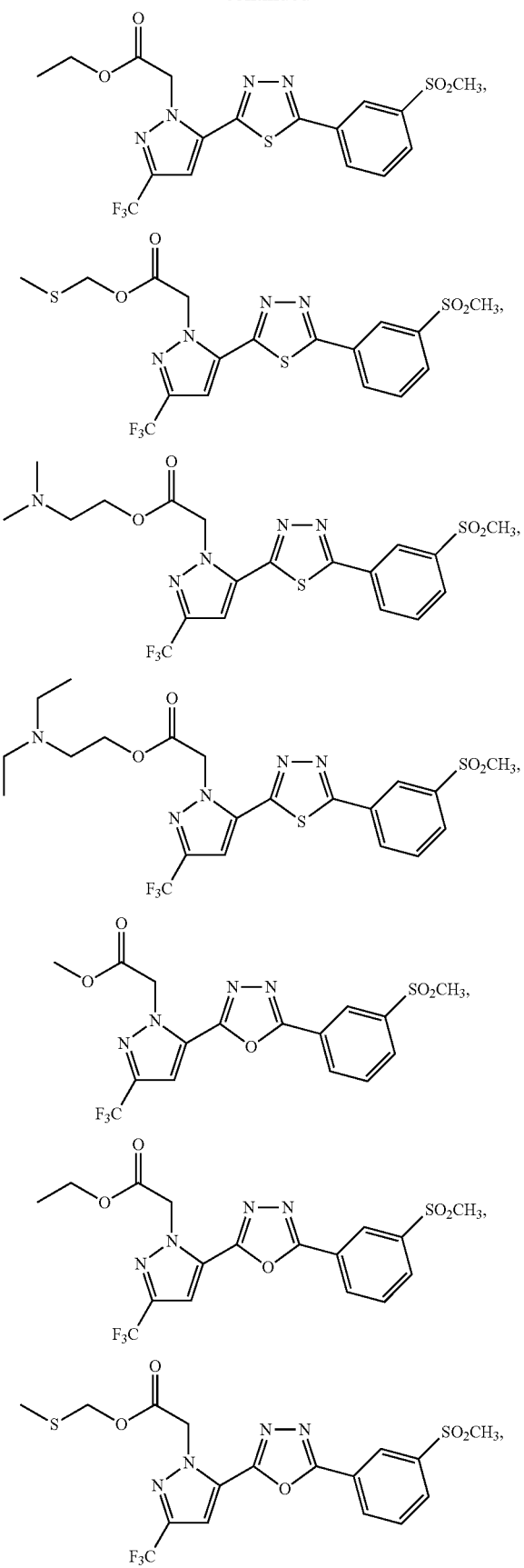
54
-continued
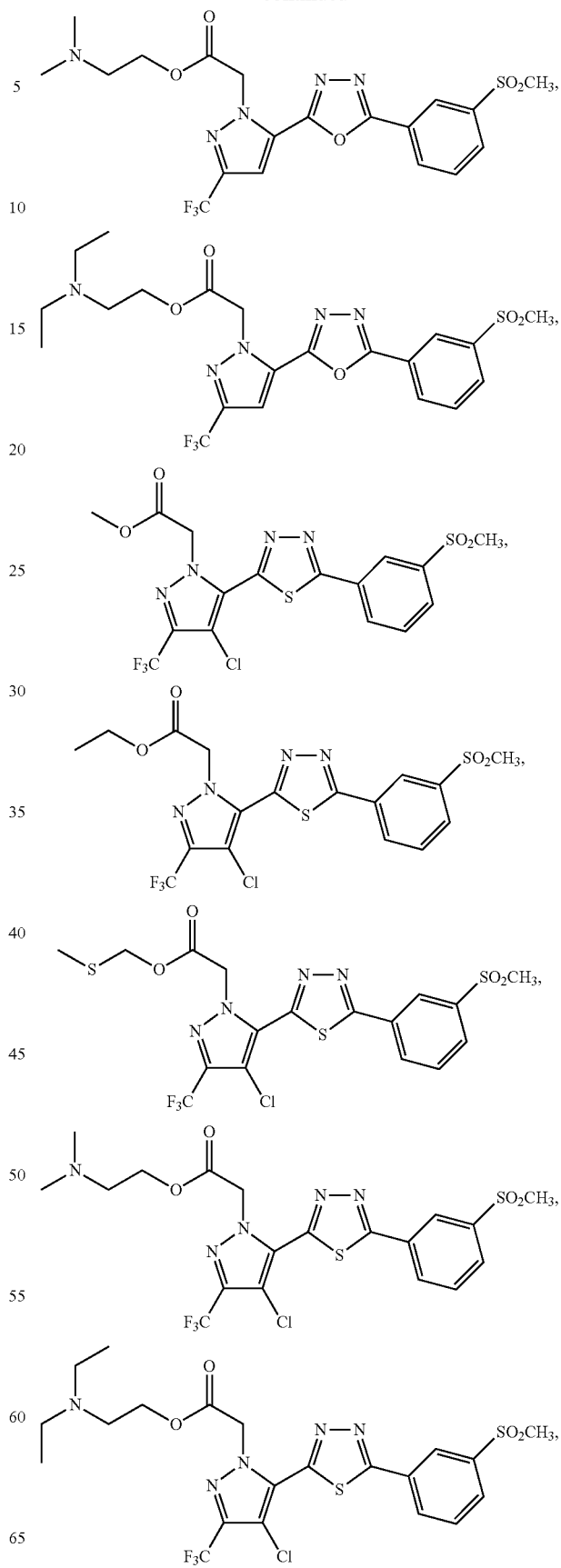

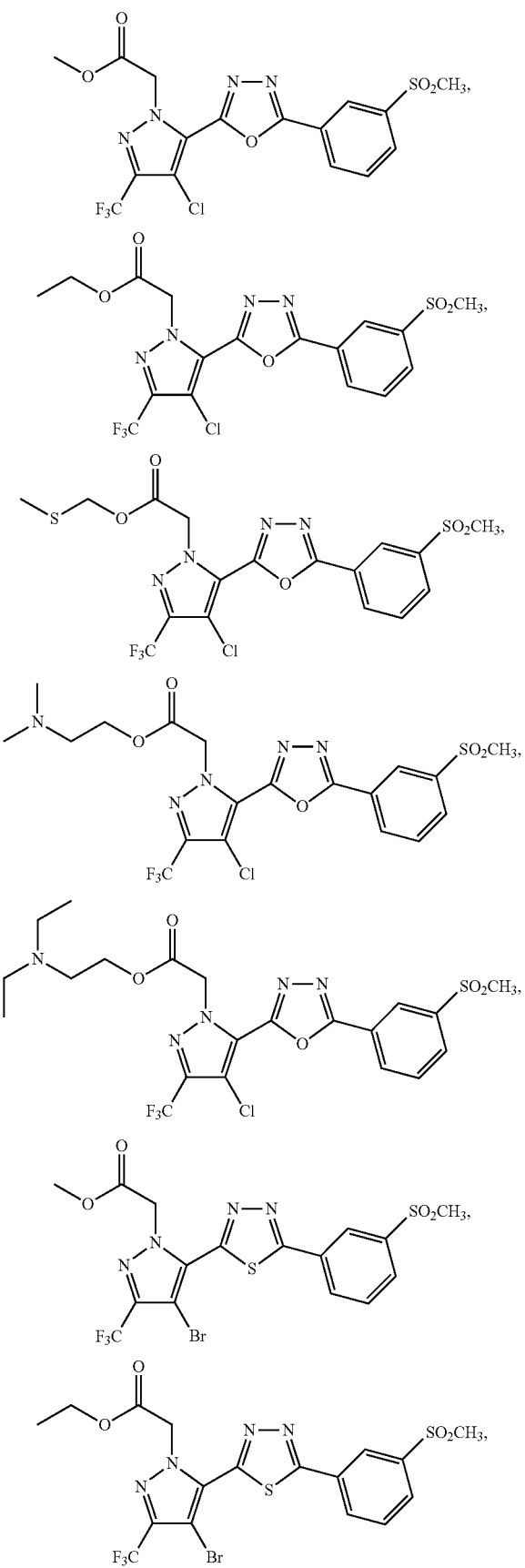
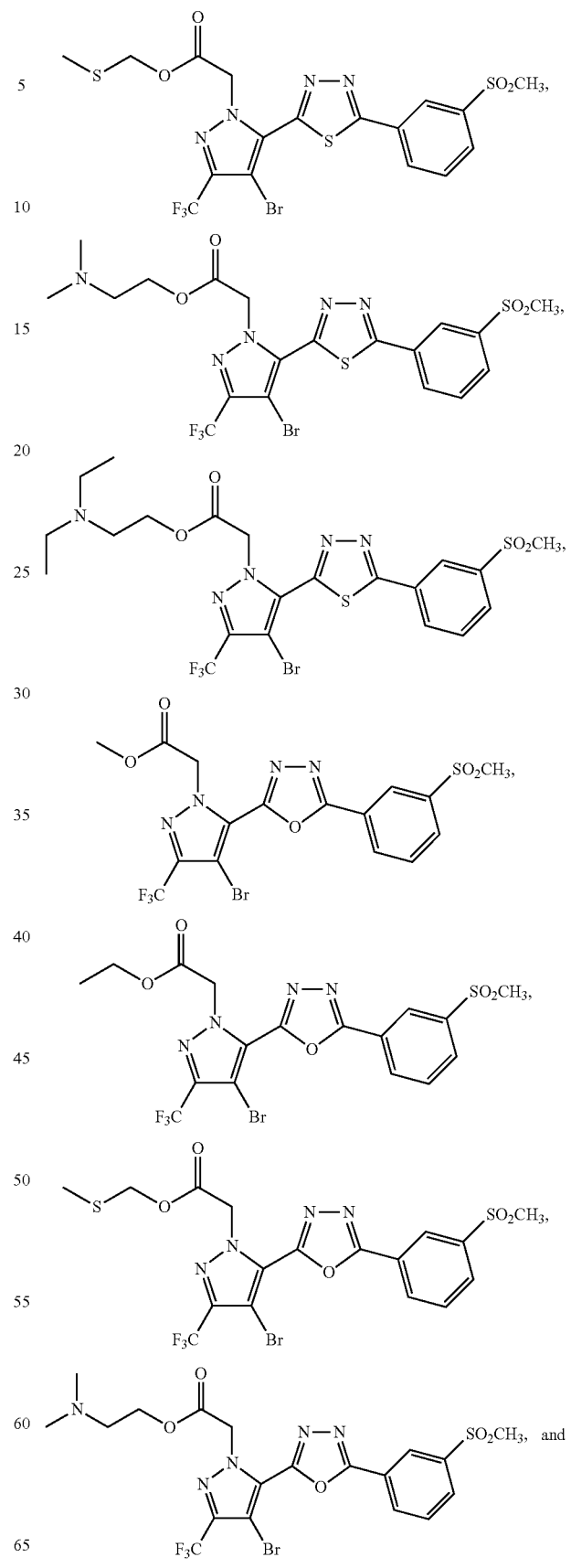

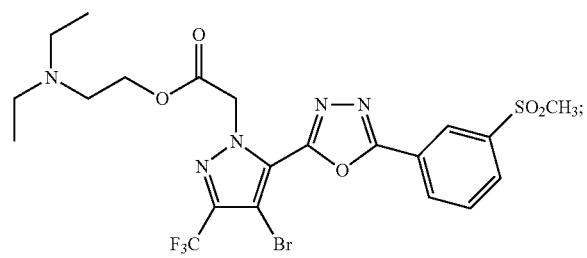
pharmaceutically acceptable salt, pharmaceutically acceptable solvate, or pharmaceutically acceptable prodrug thereof.
In some embodiments is a compound selected from:
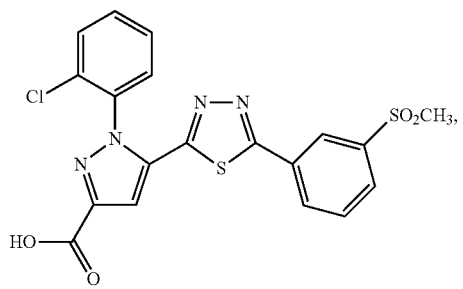
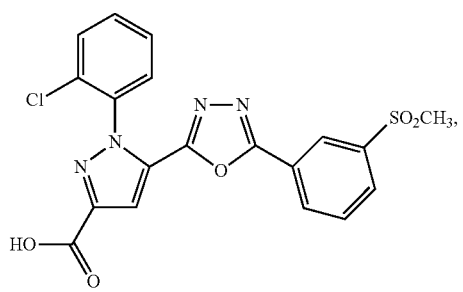
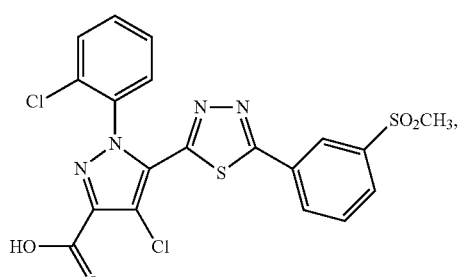
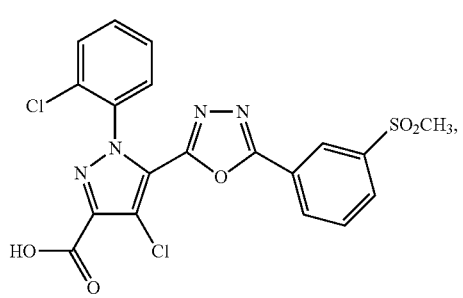
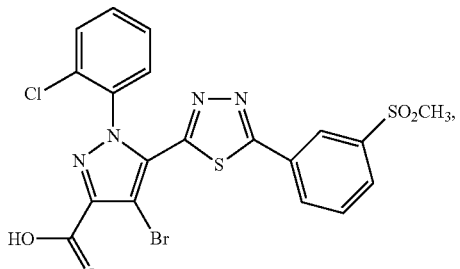
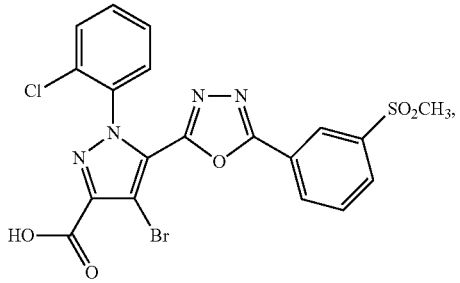
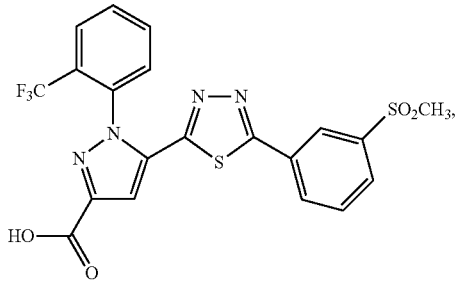
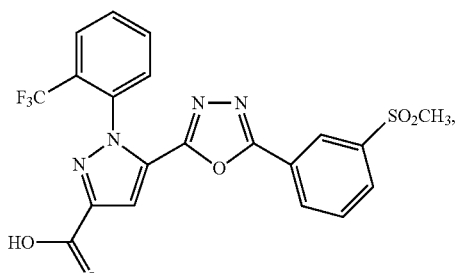
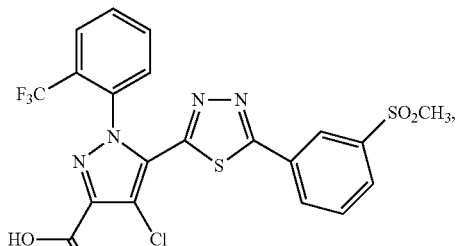
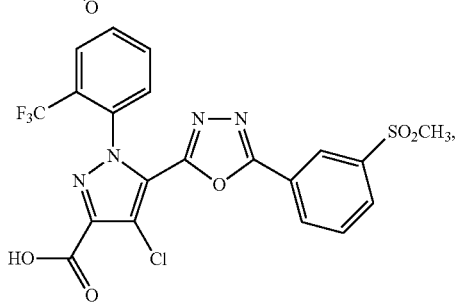

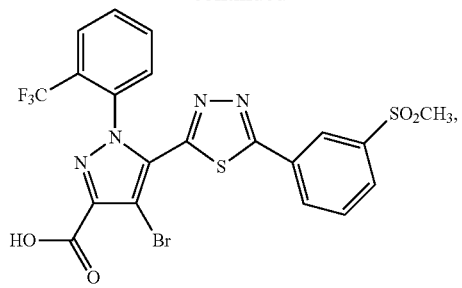
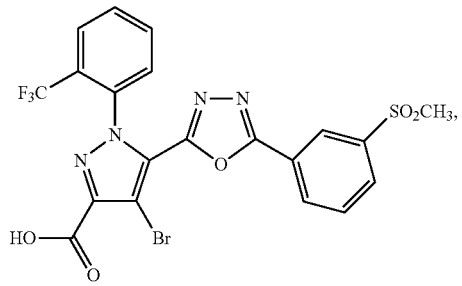
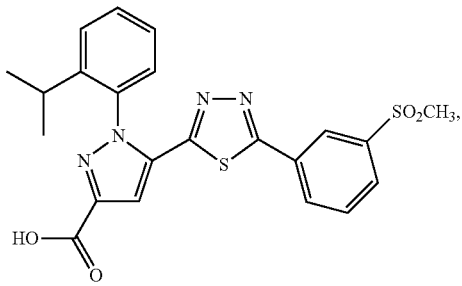
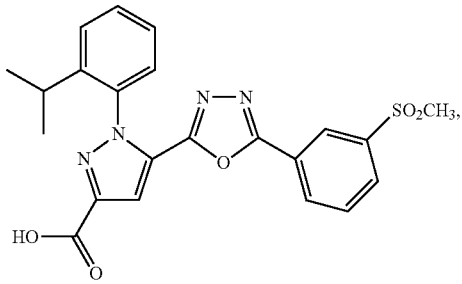
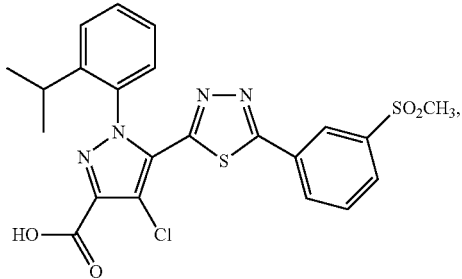
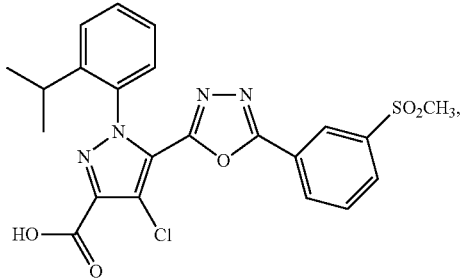
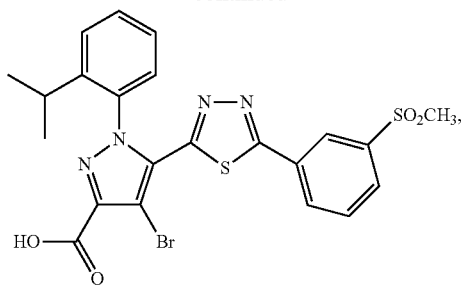
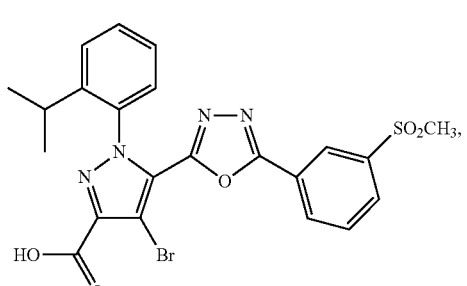
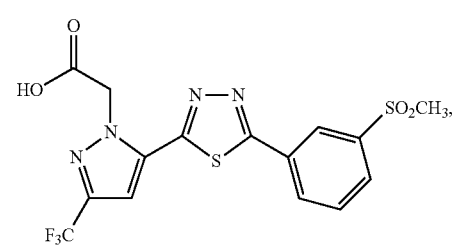
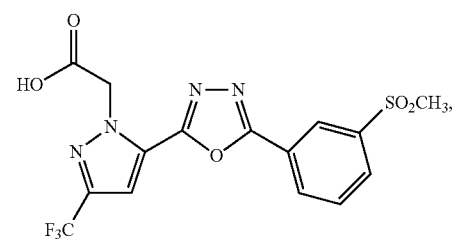
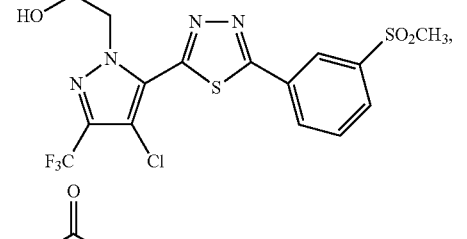
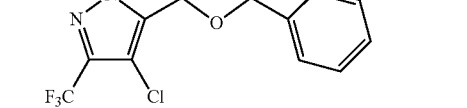

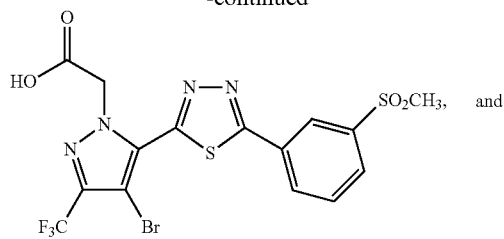
and
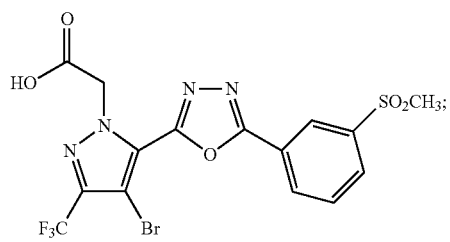
or a pharmaceutically acceptable salt, pharmaceutically acceptable solvate, or pharmaceutically acceptable prodrug thereof.
In some embodiments is a compound selected from:
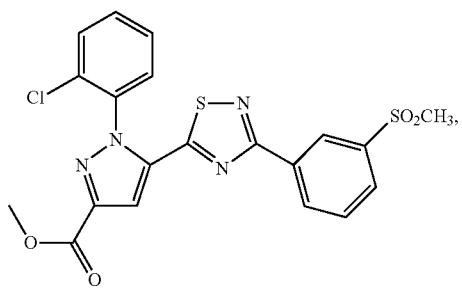
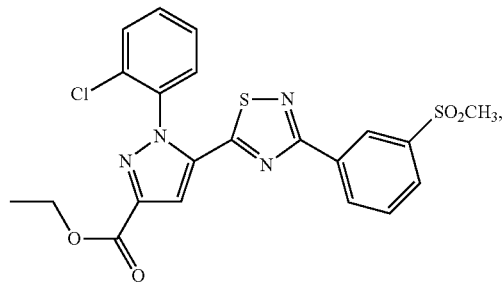
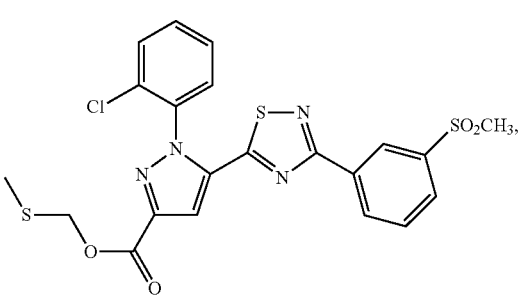
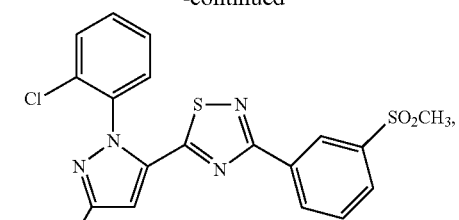
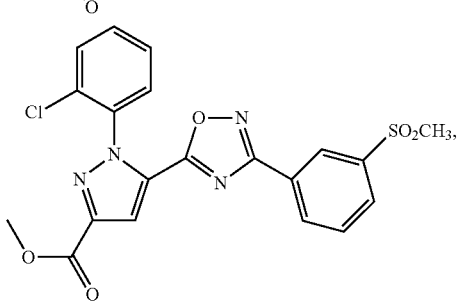
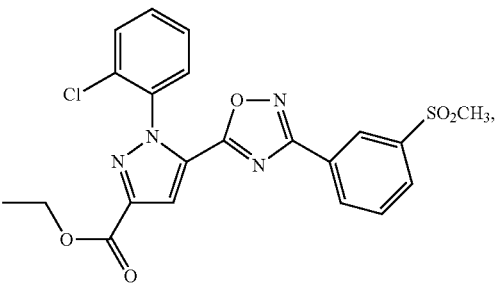
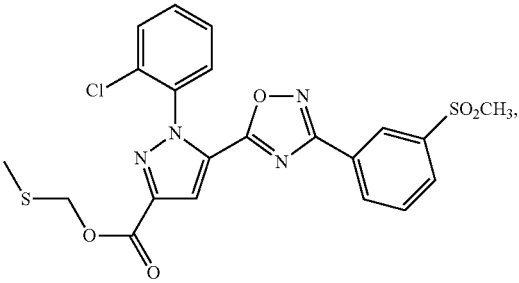
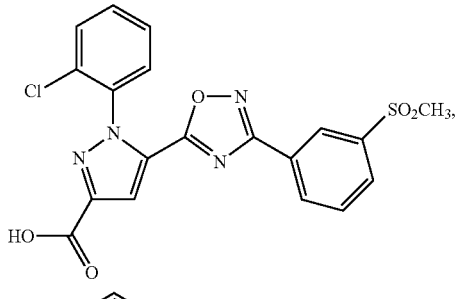
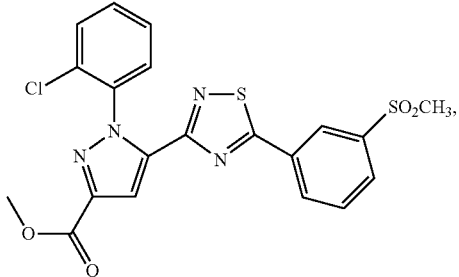

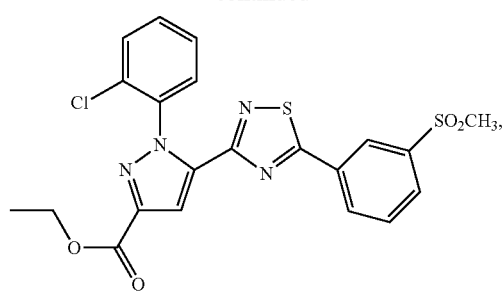
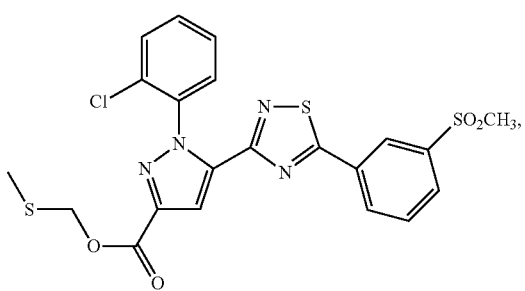
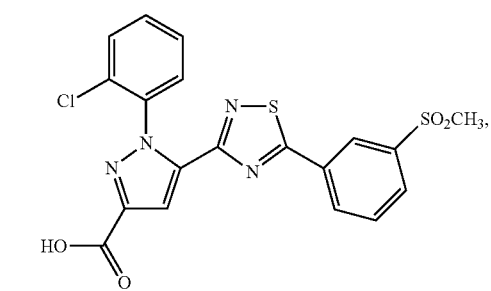
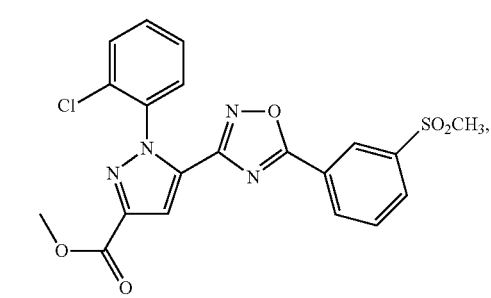
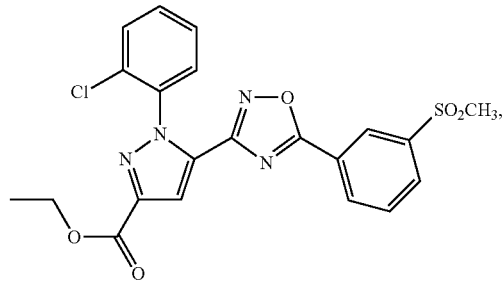
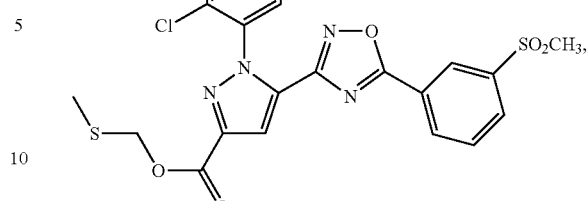
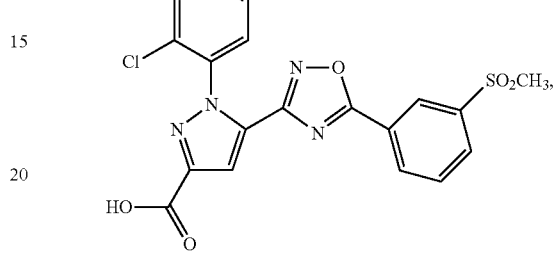
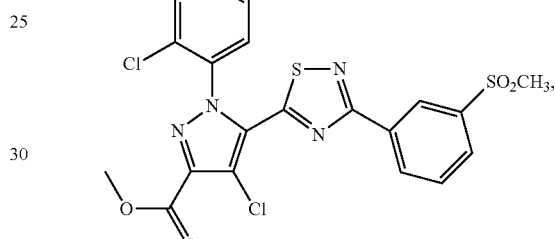
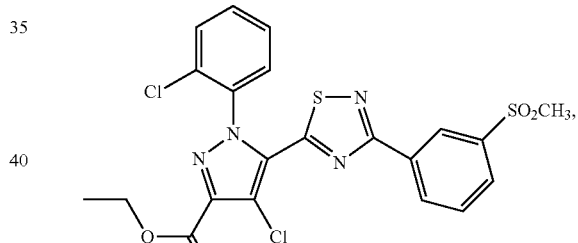
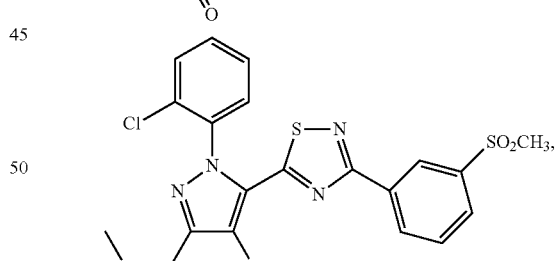
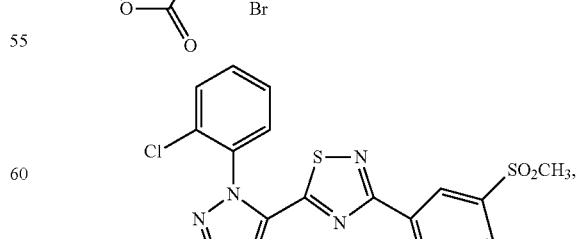
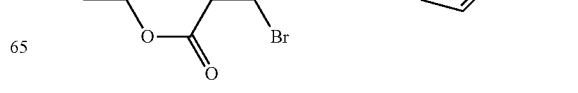

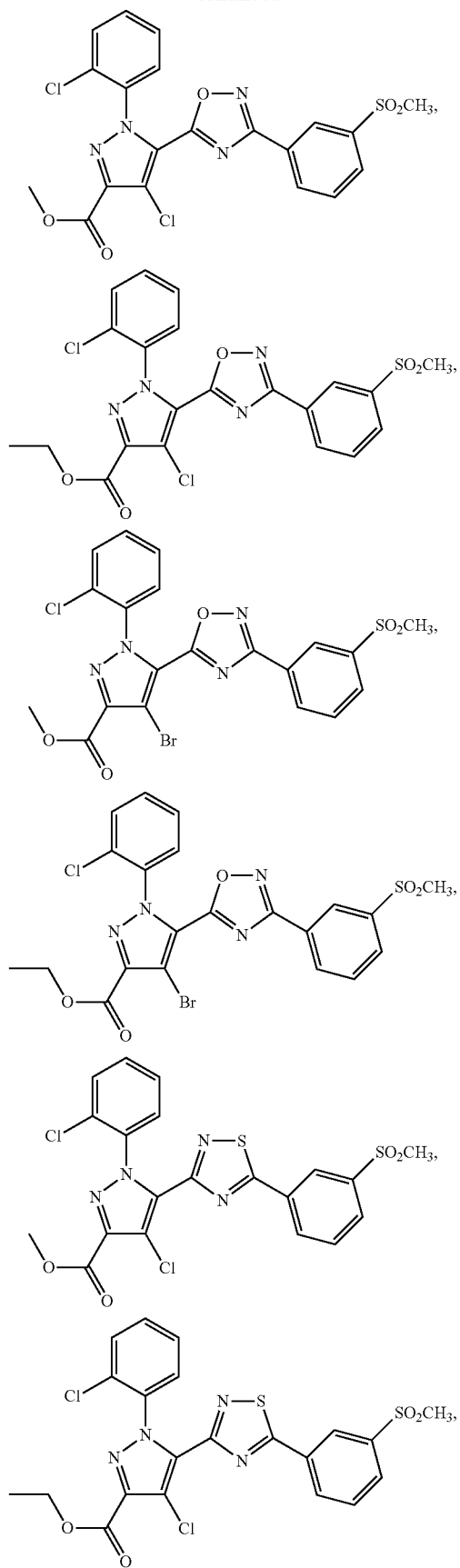
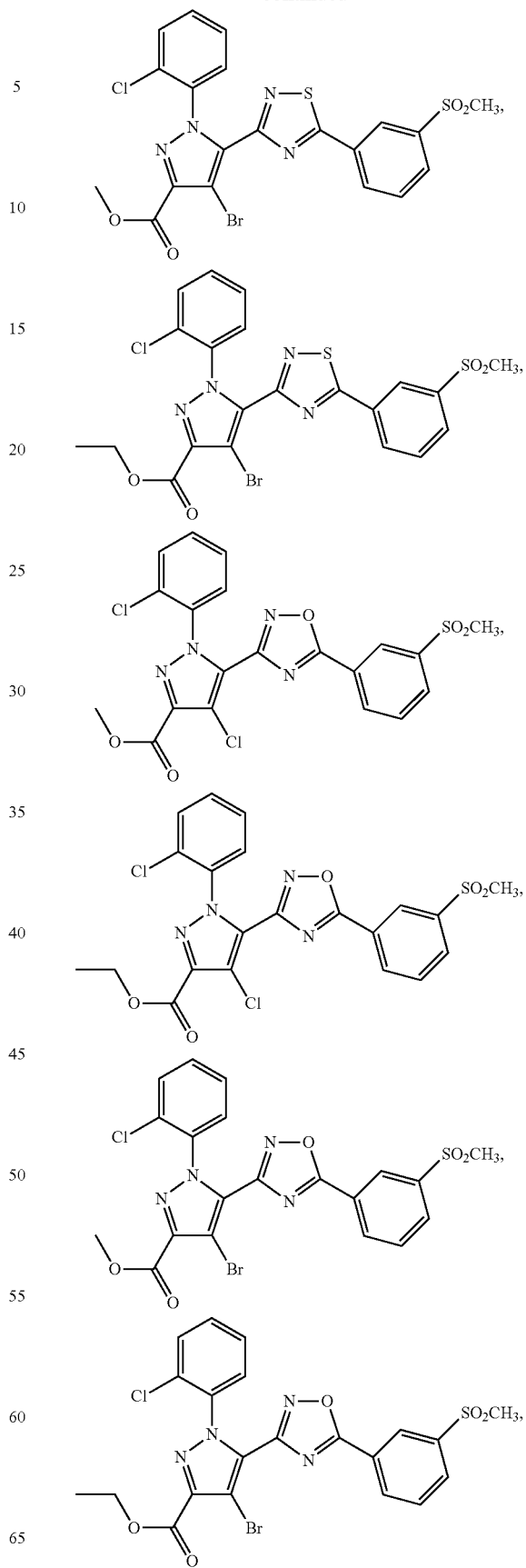

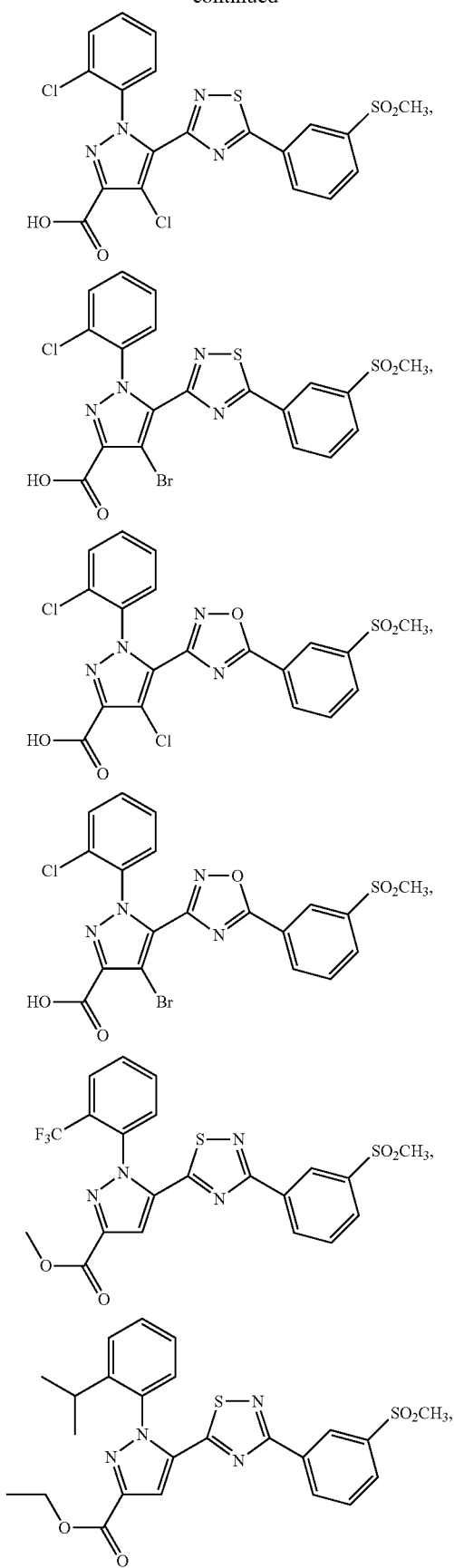
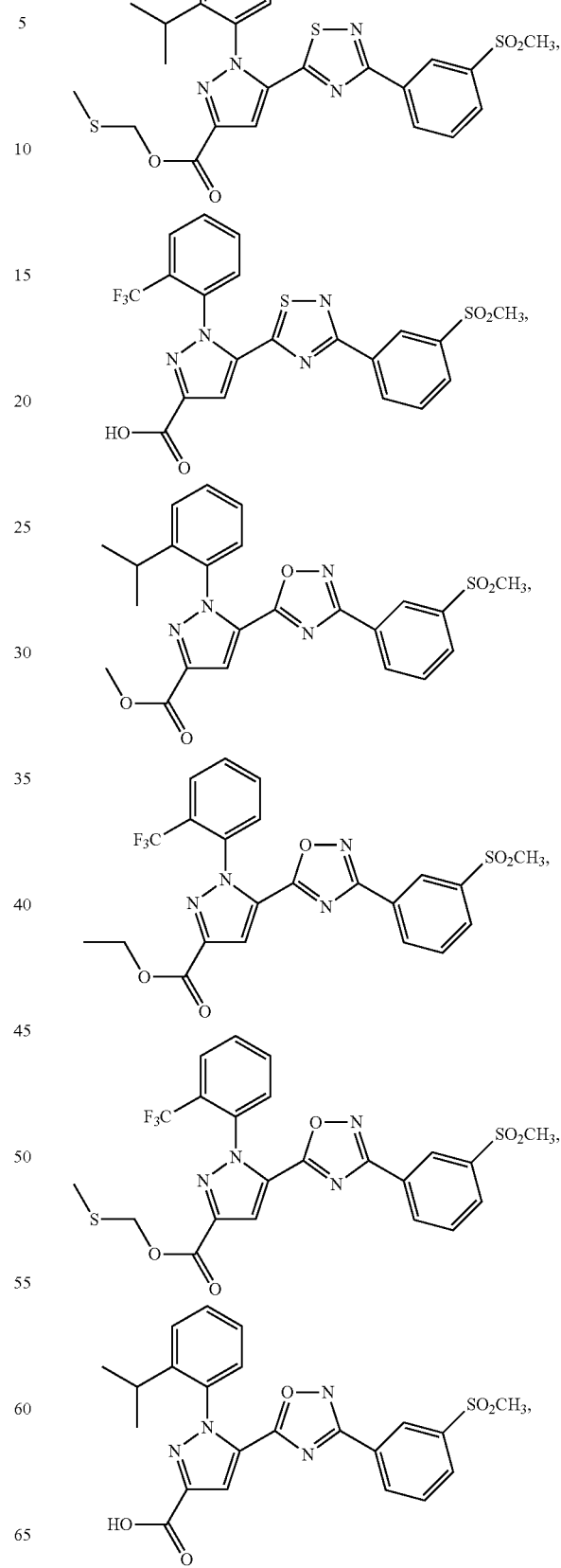

-continued
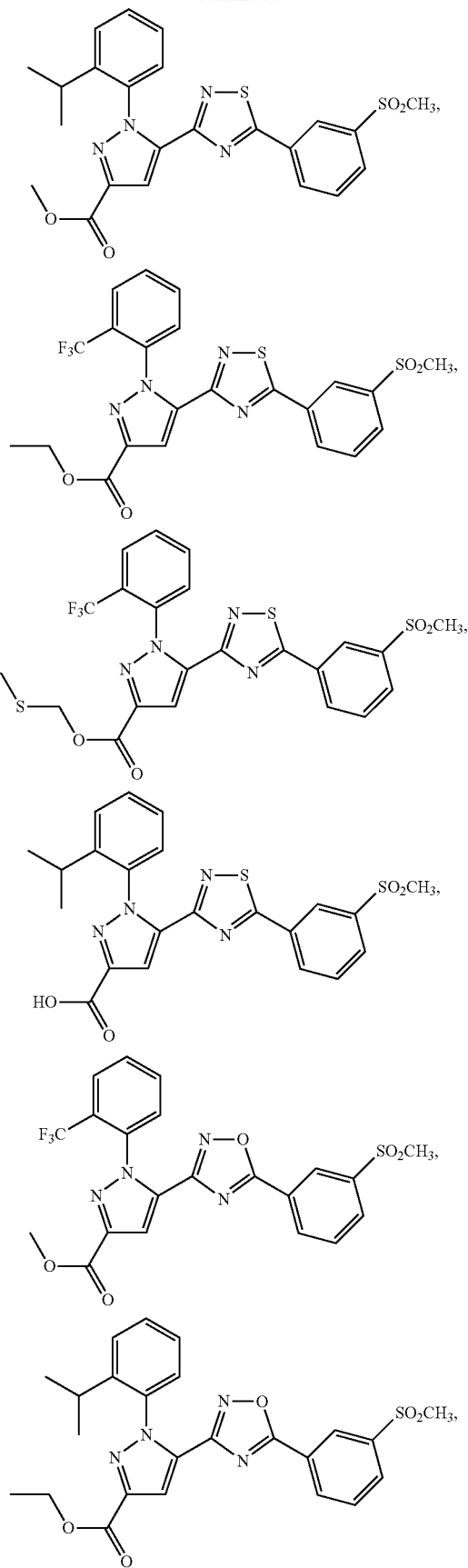
-continued
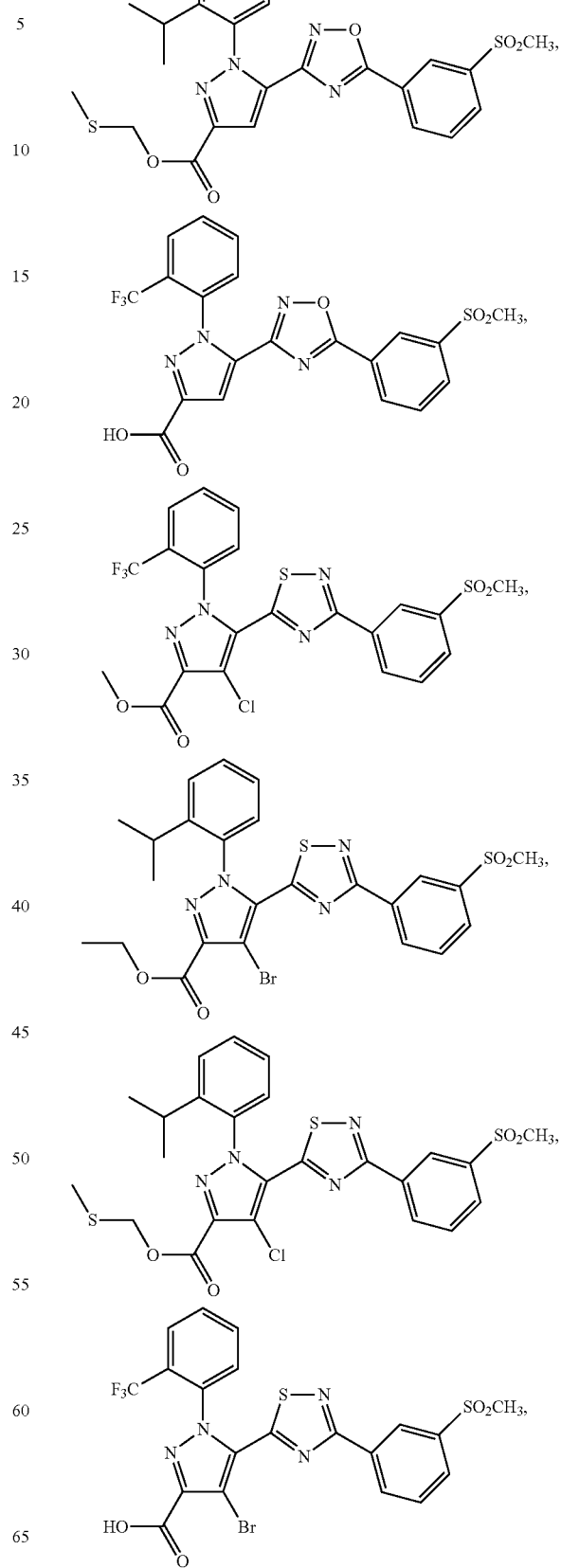

-continued
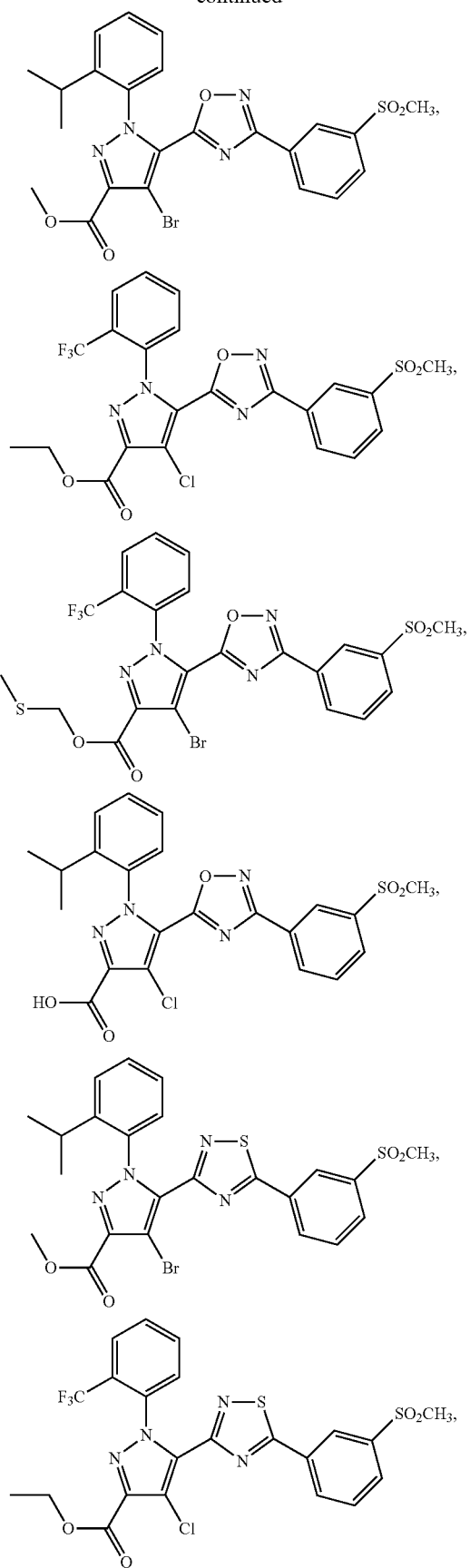
-continued
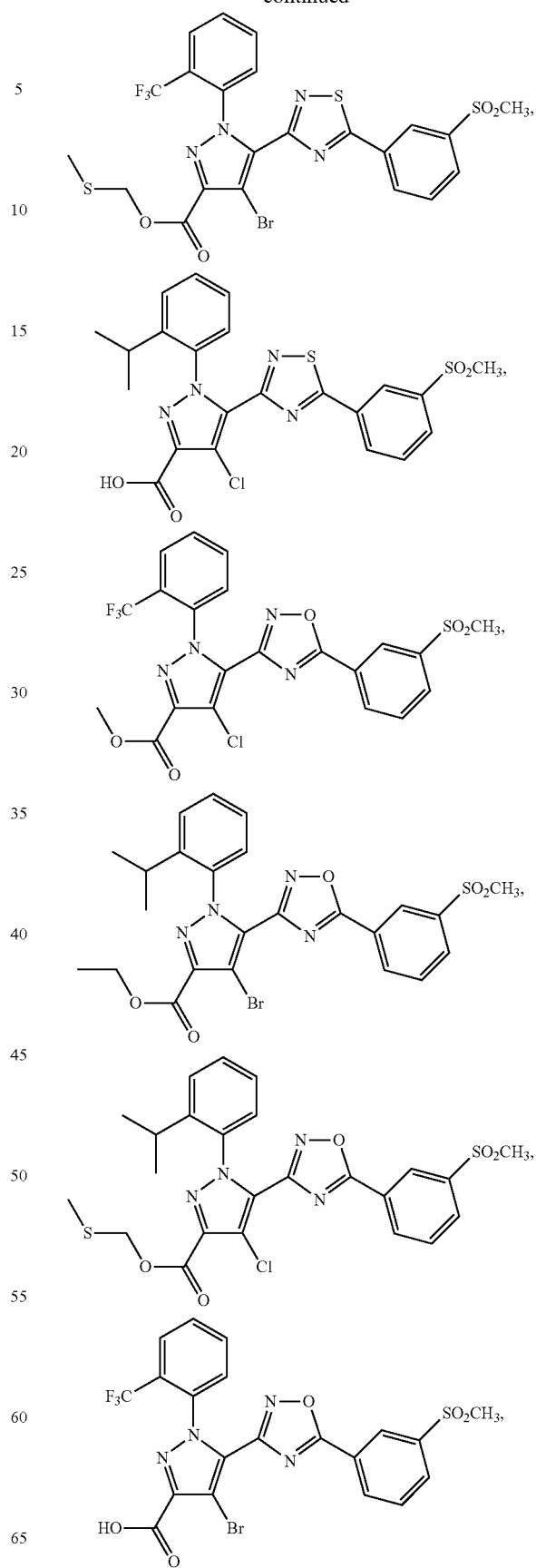

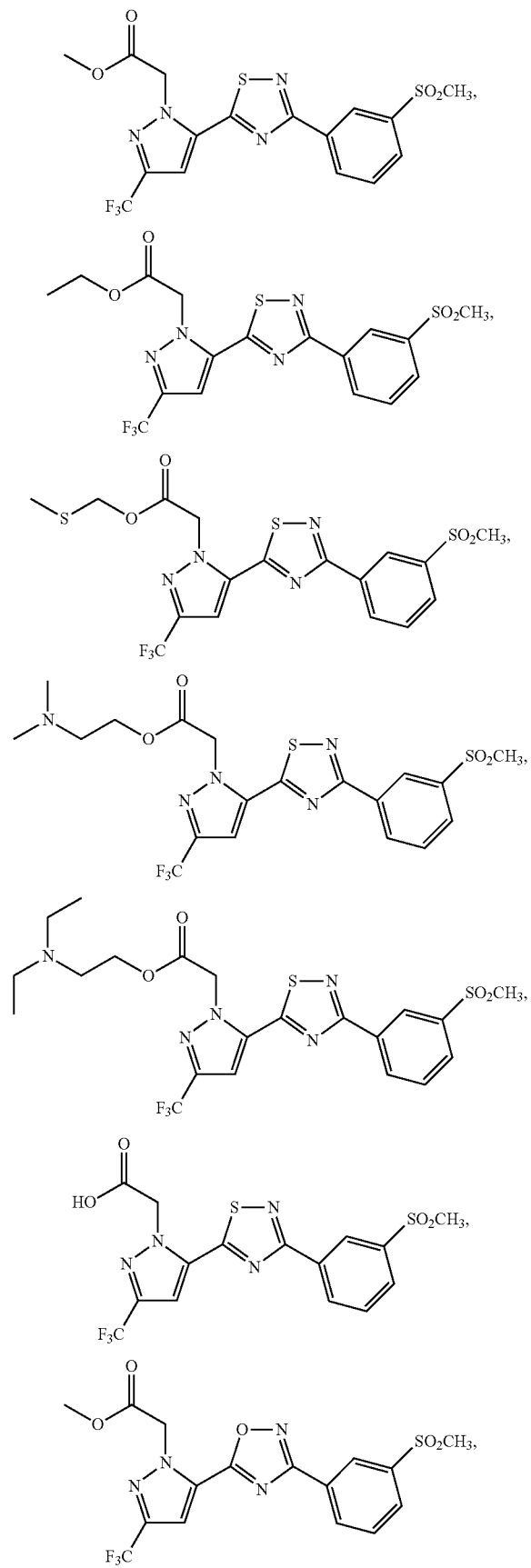
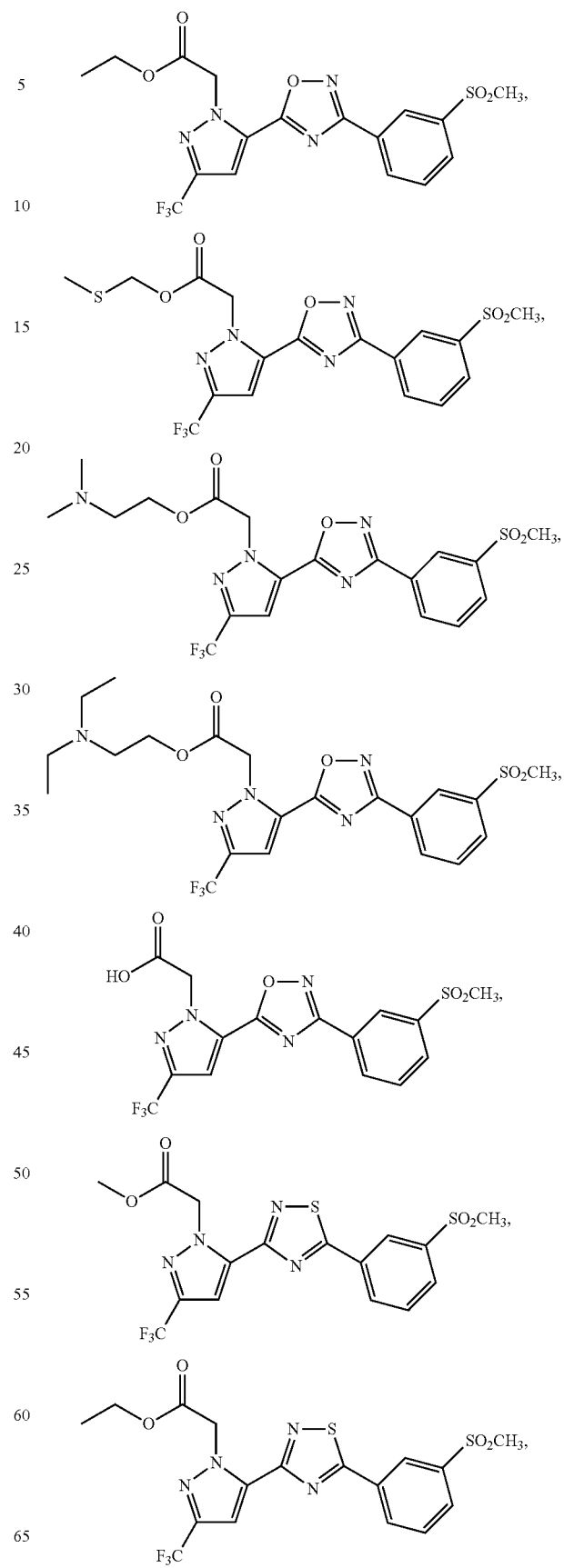

75
-continued
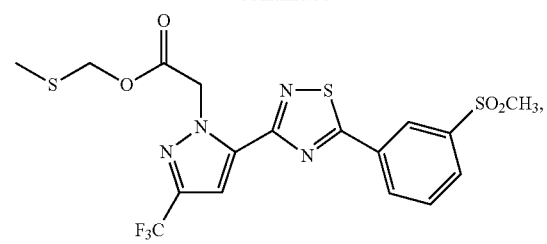
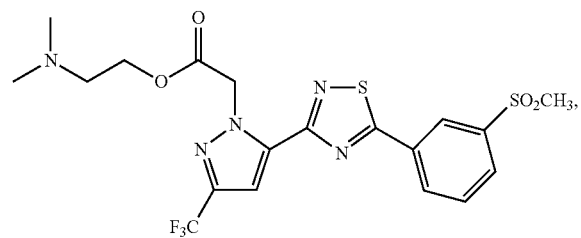
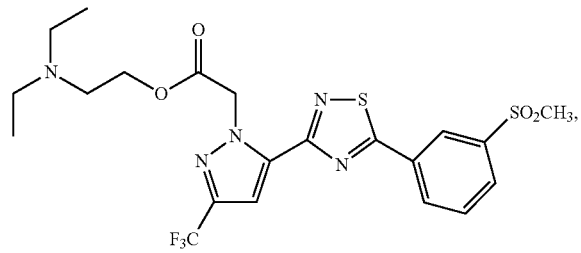
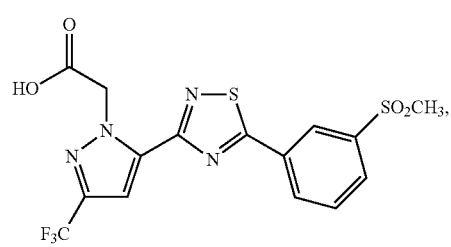
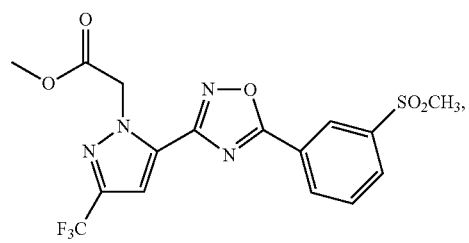
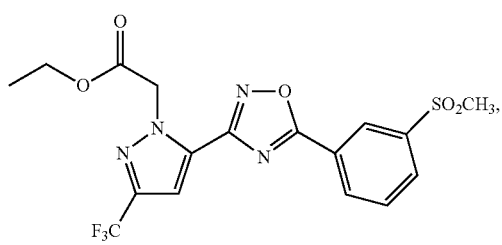
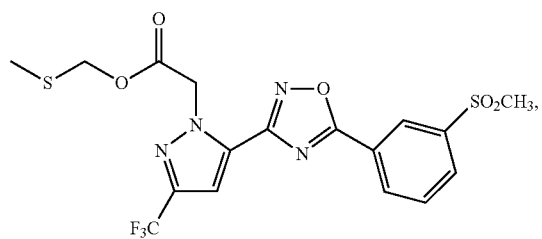
76
-continued
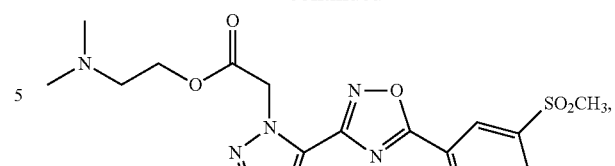
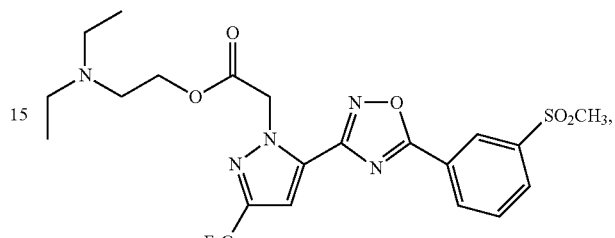
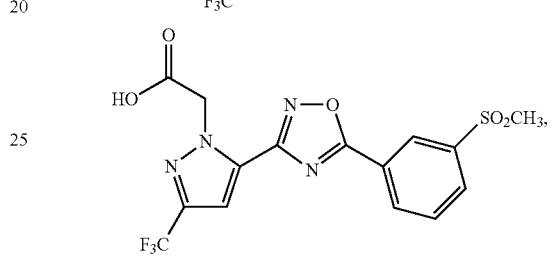
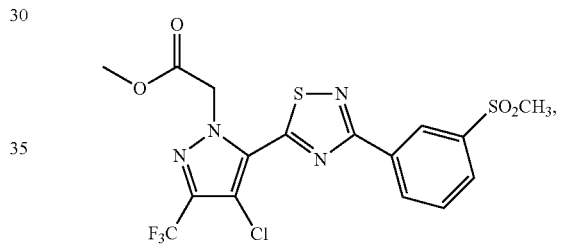
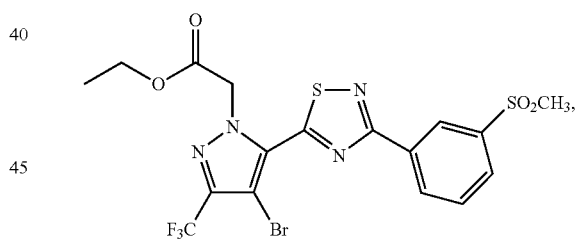
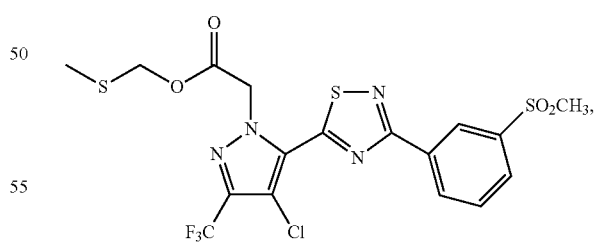
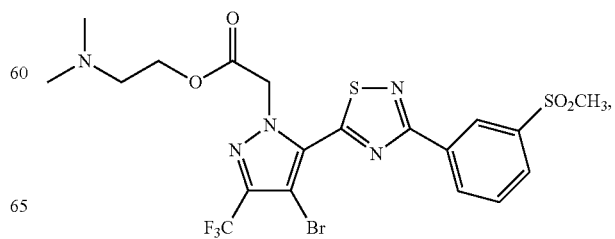

77
-continued
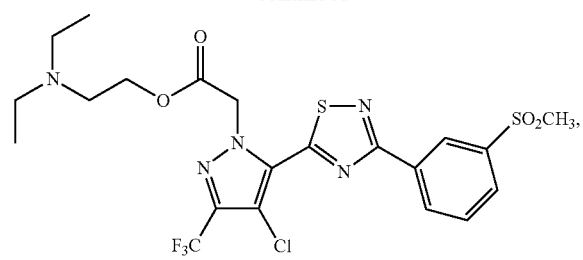
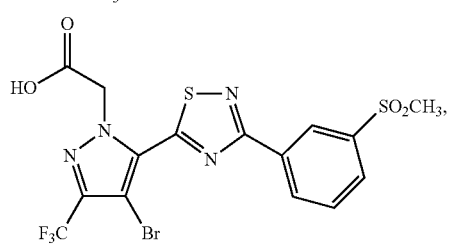
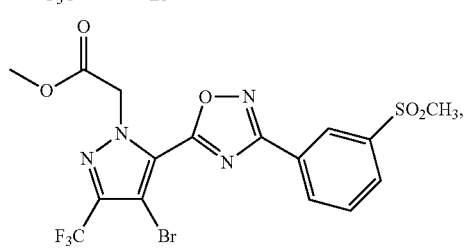
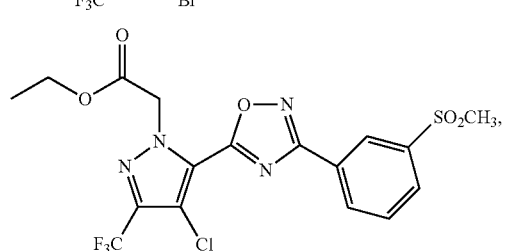
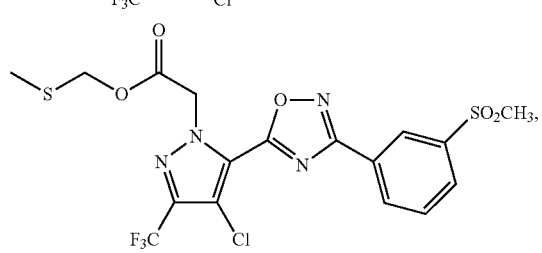
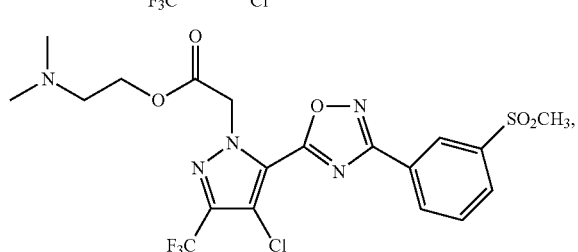
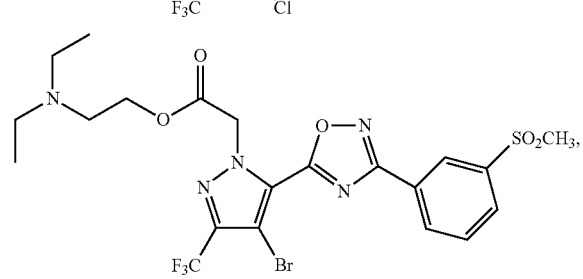
78
-continued
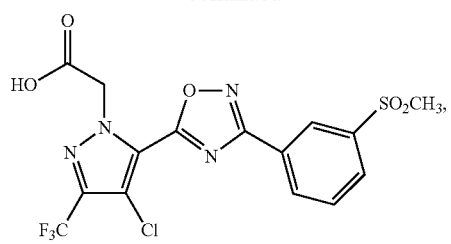 [SMILES: CS(=O)(=O)c1cccc(-c2nc(-c3c(Br)c(C(F)(F)F)nn3CC(=O)O)no2)c1]
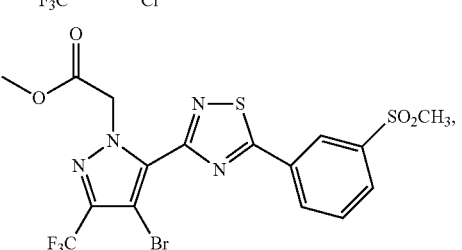
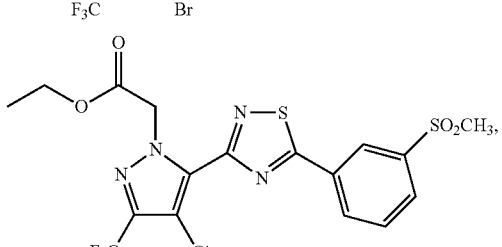
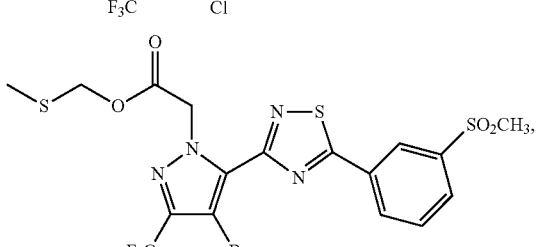
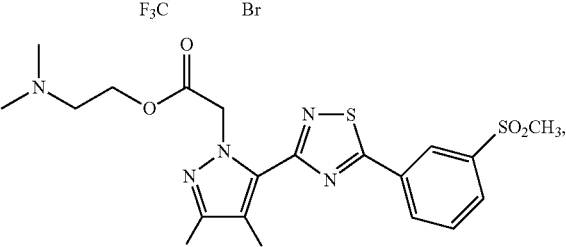
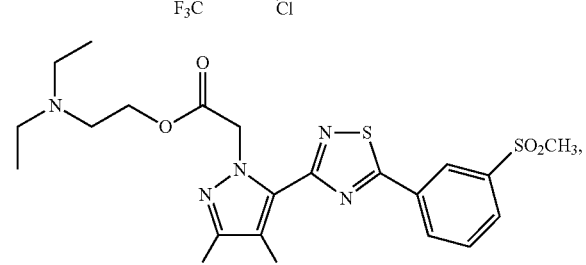
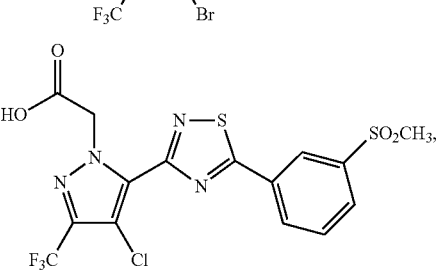

-continued
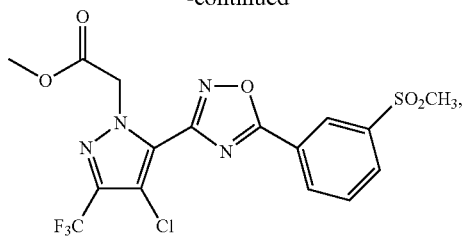
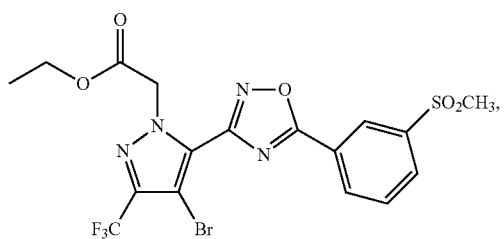
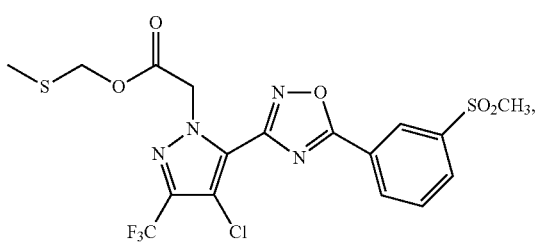
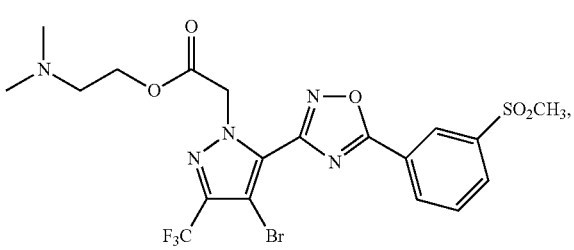
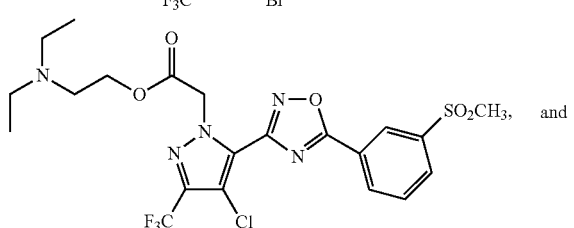 and
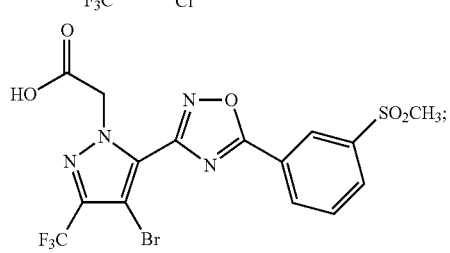
or a pharmaceutically acceptable salt, pharmaceutically acceptable solvate, or pharmaceutically acceptable prodrug thereof.
In some embodiments is a compound selected from:
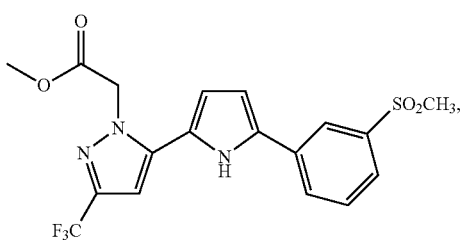
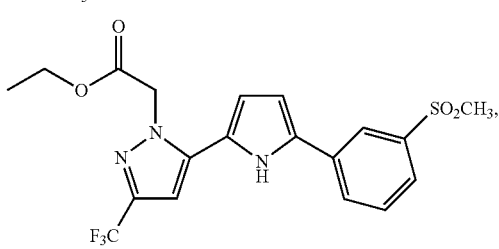
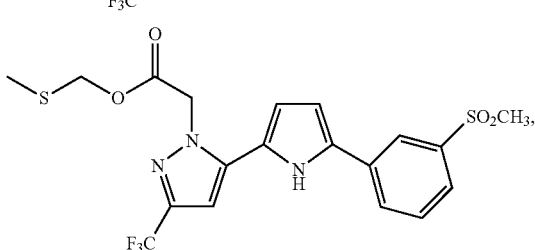
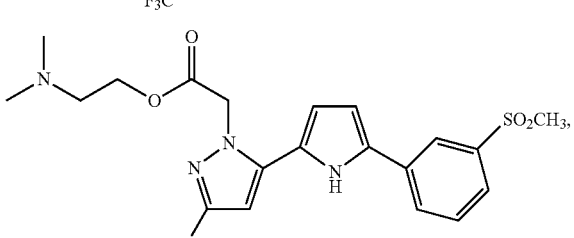
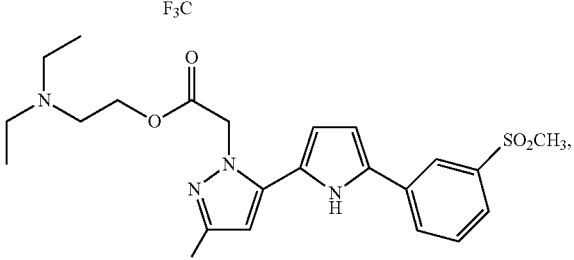
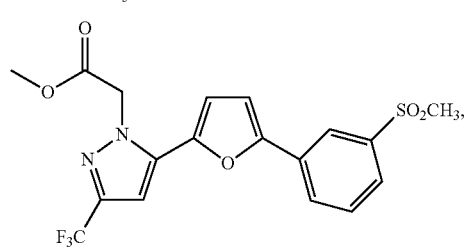
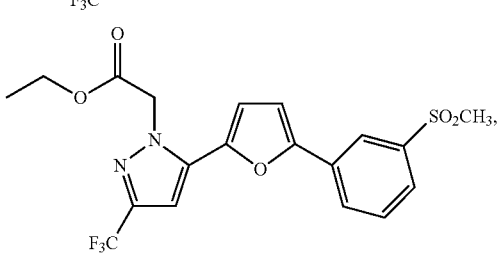

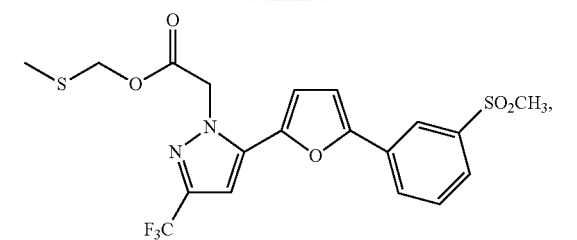
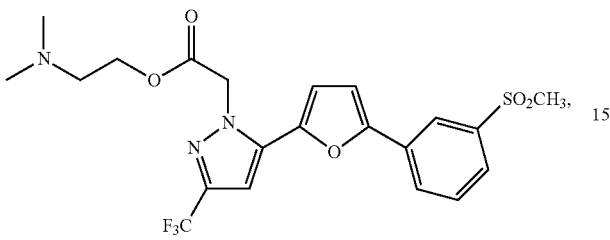
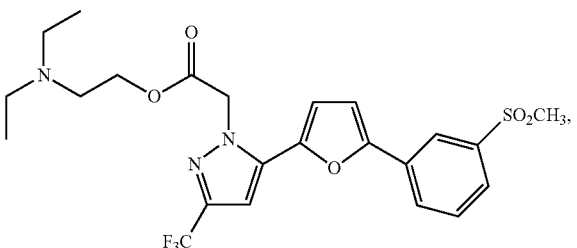
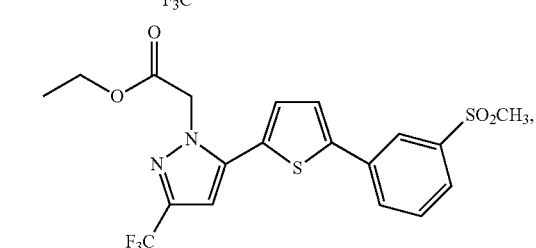
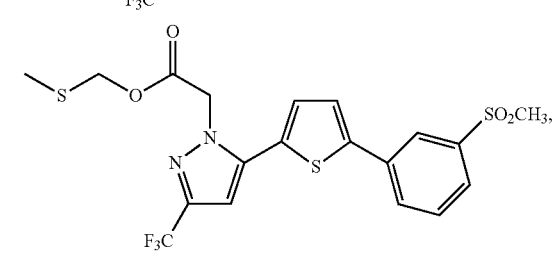
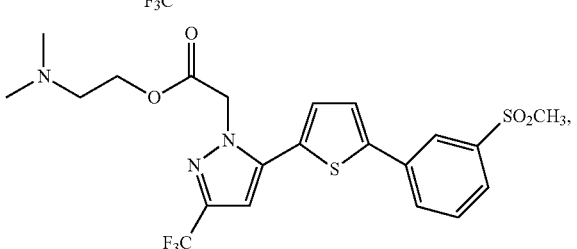
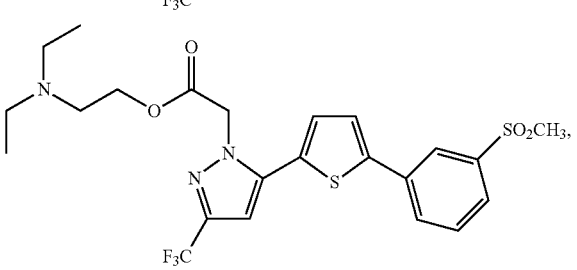
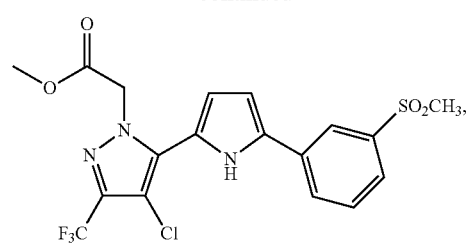
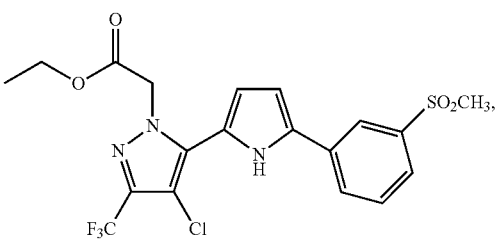
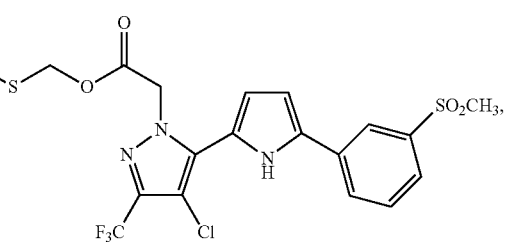
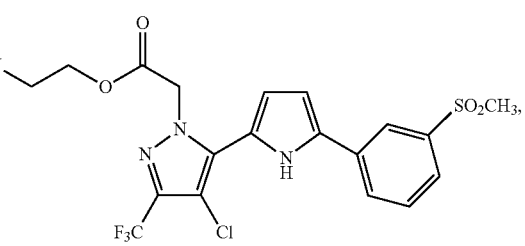
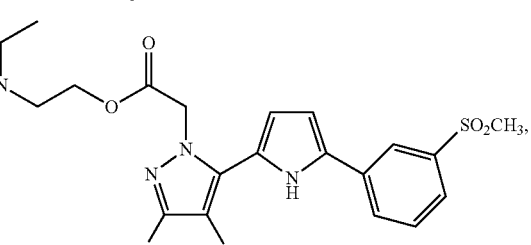
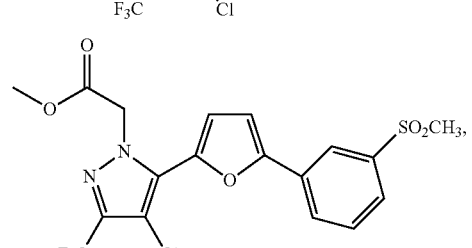
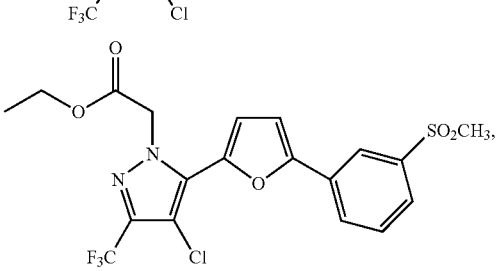

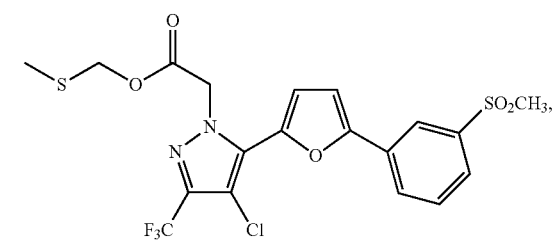
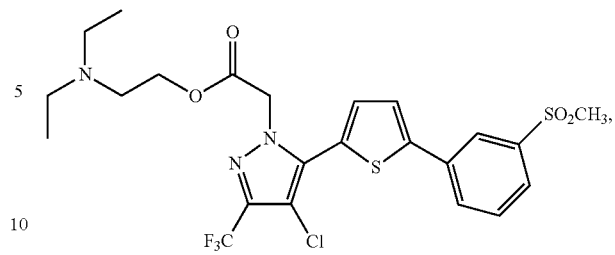
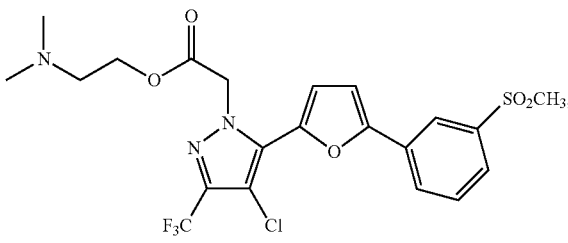
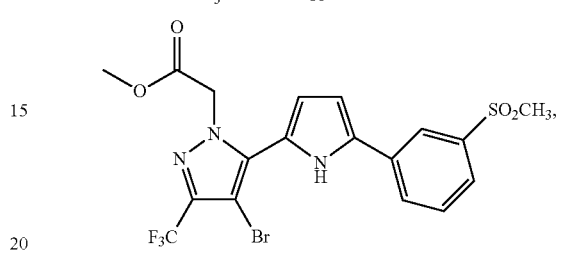
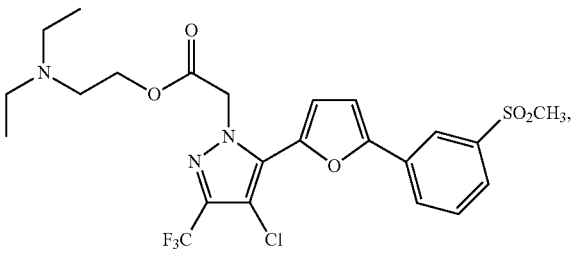
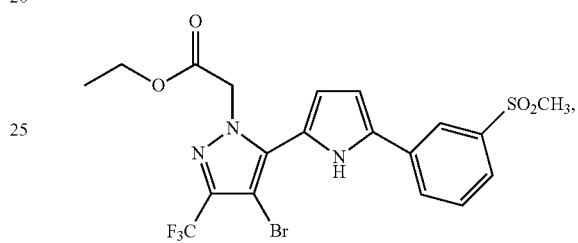
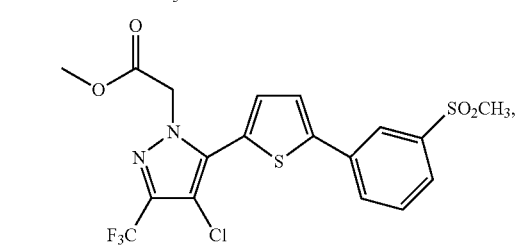
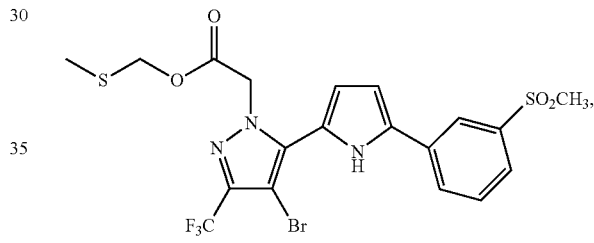
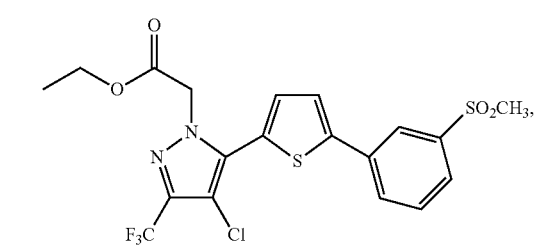
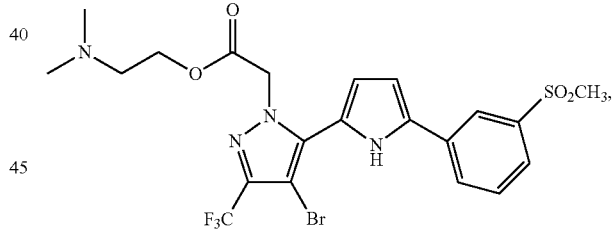
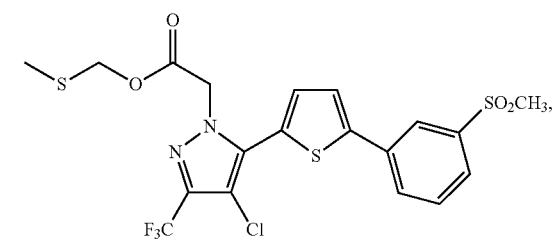
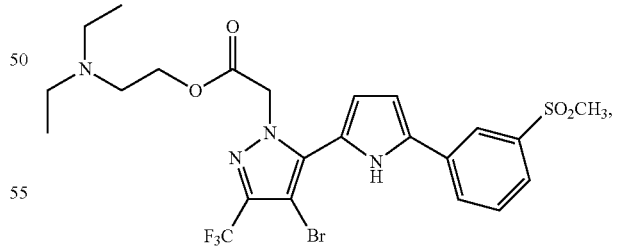
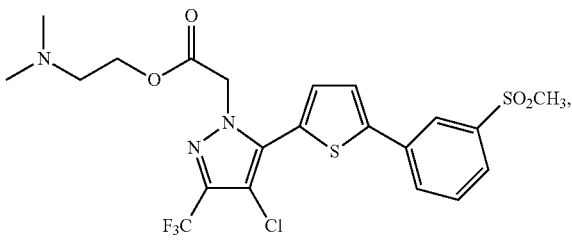
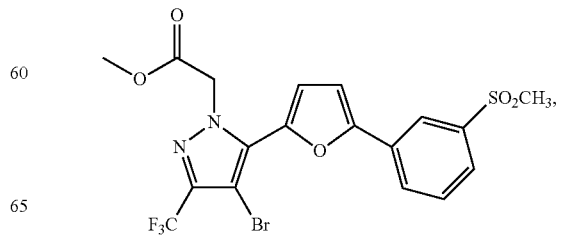

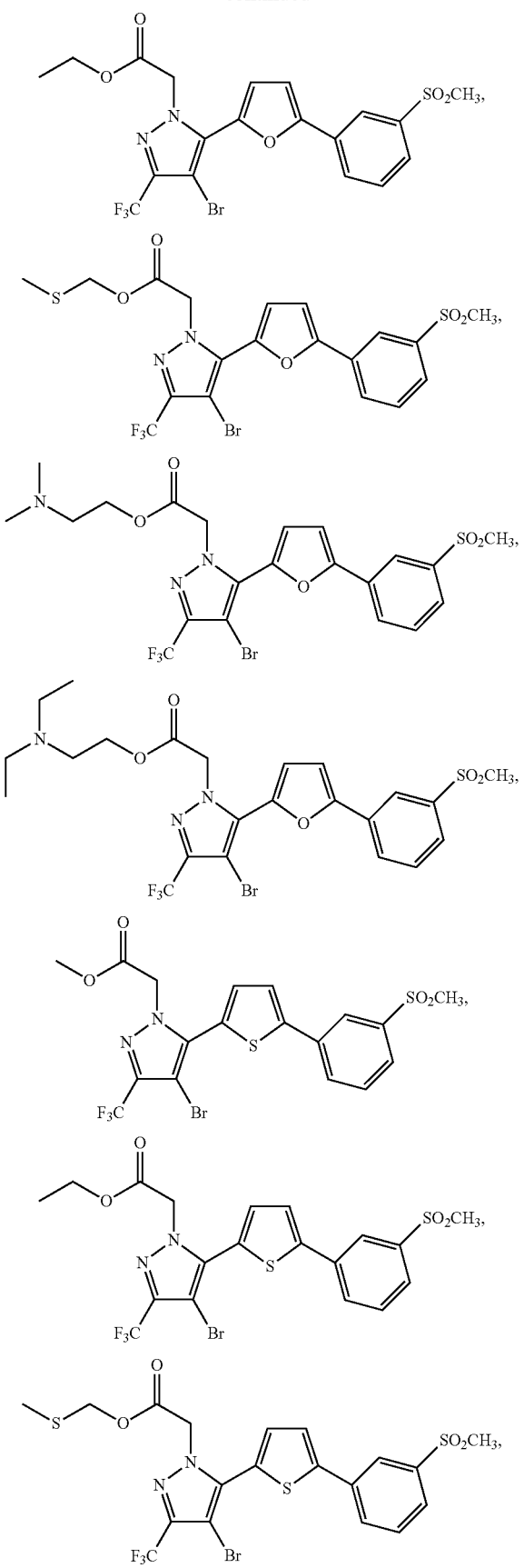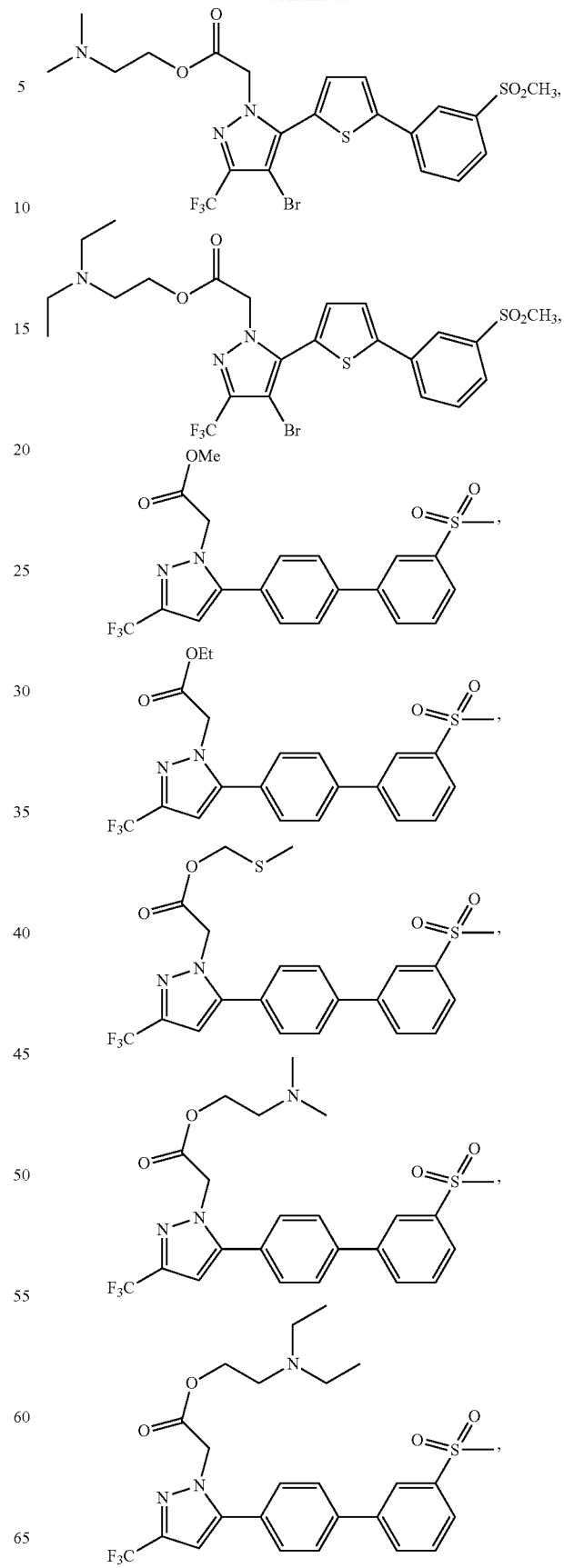

87
-continued
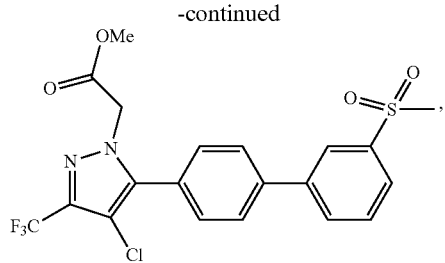
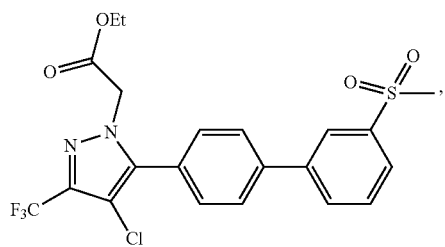
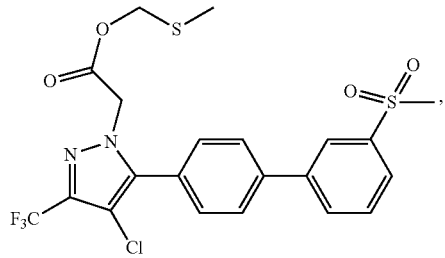
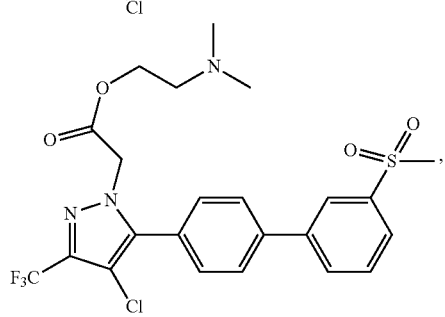
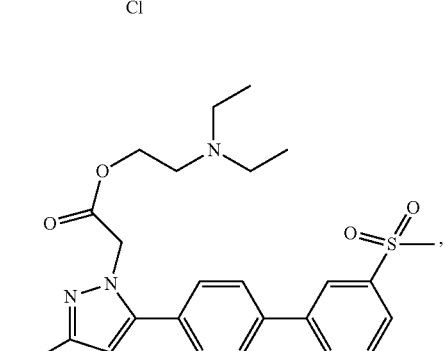
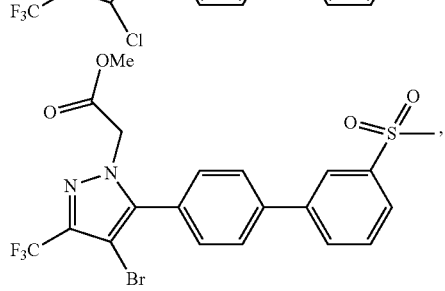
88
-continued
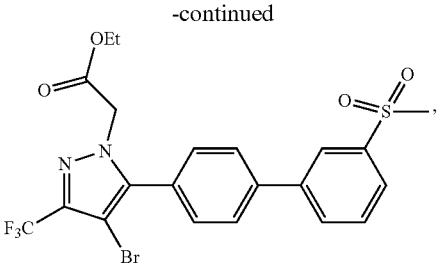
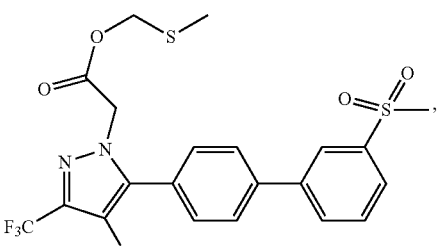
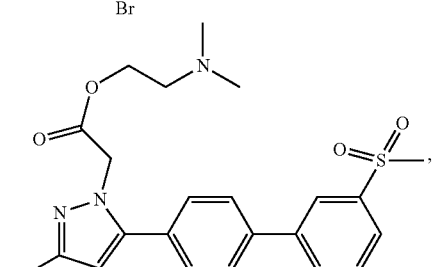
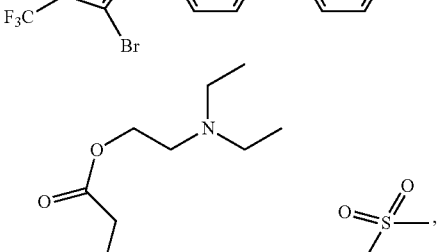
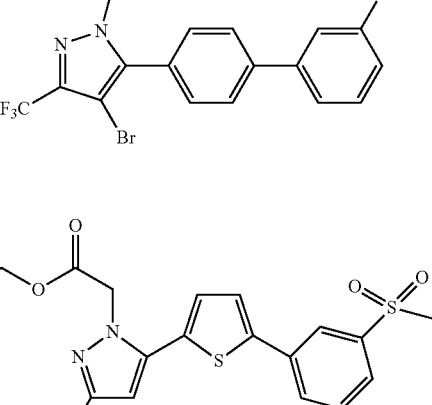
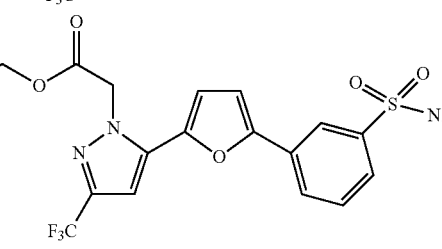

89
-continued
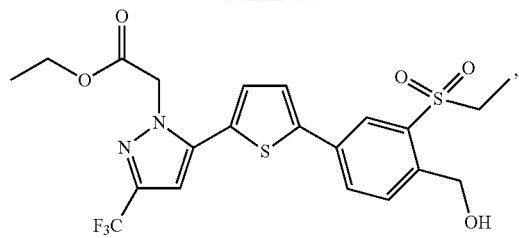
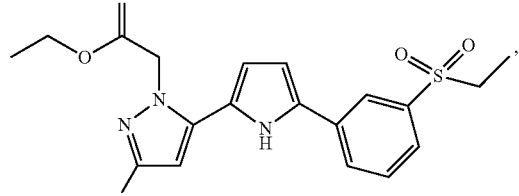
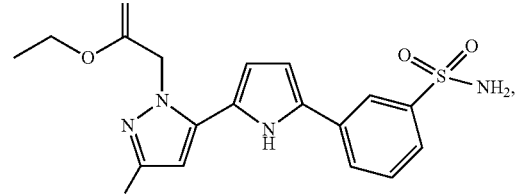
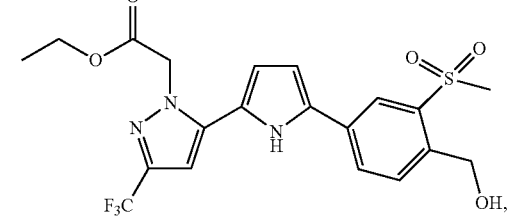
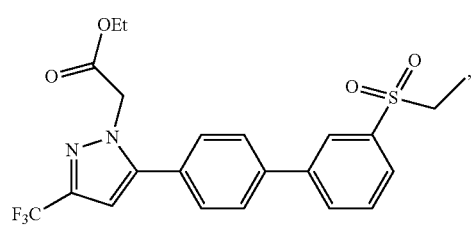
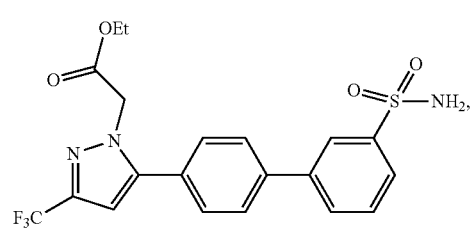
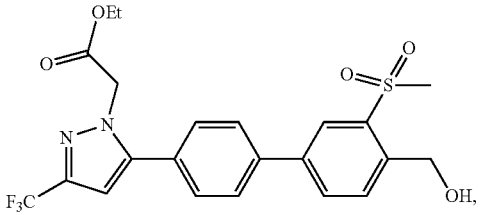
90
-continued
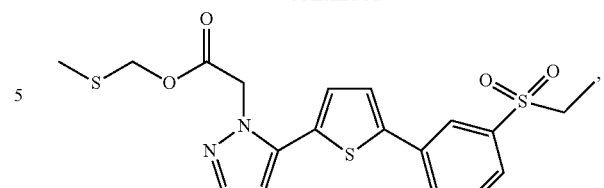
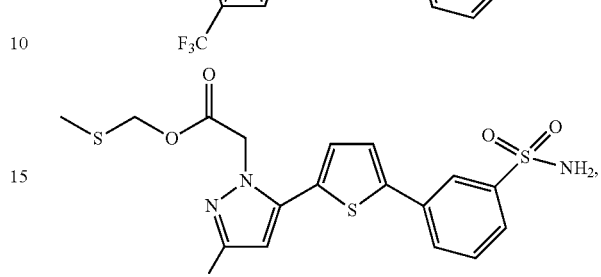
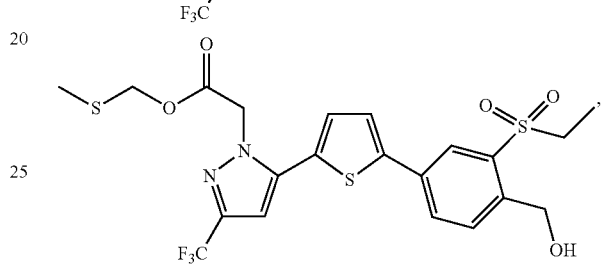
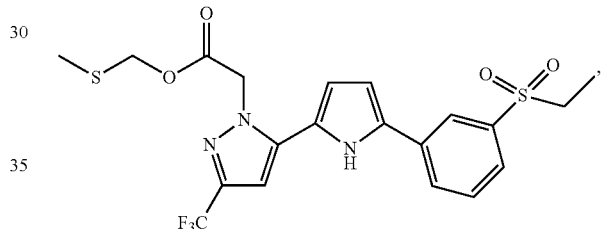
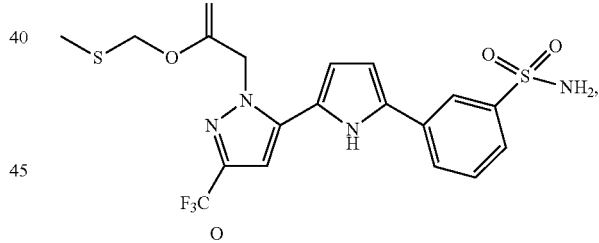
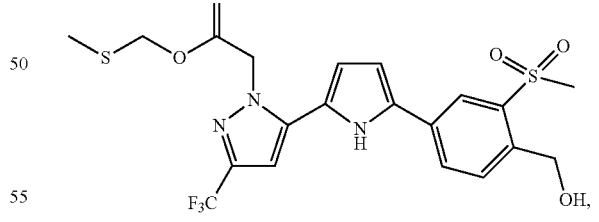
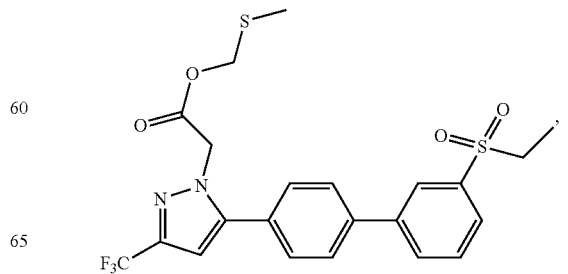

-continued

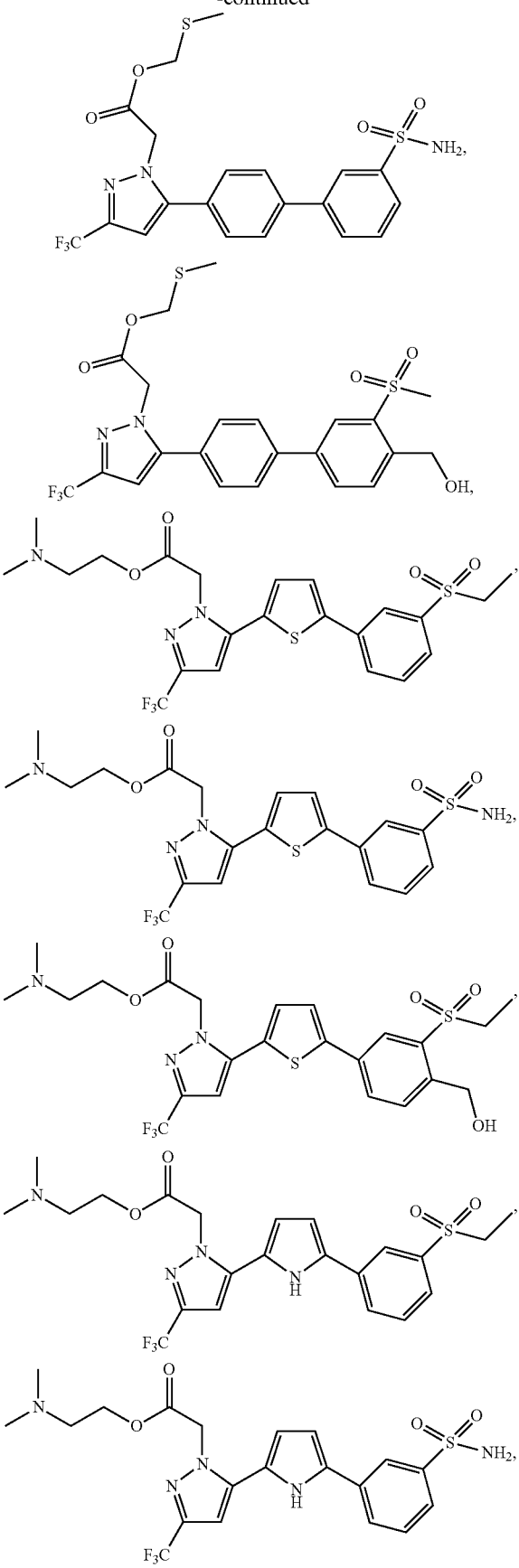

-continued

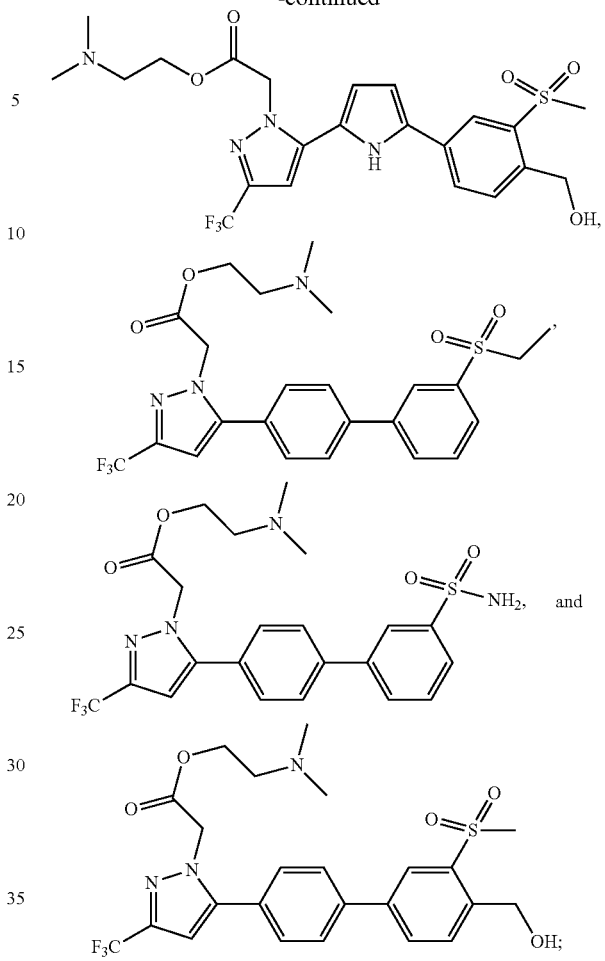

or a pharmaceutically acceptable salt, pharmaceutically acceptable solvate, or pharmaceutically acceptable prodrug thereof.

In some embodiments, the therapeutic agent(s) (e.g. compound of Formula I, II, III, IV, V, or VI) is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula I, II, III, IV, V, or VI is used as a single enantiomer. In some embodiments, a compound of Formula I, II, III, IV, V, or VI is used as a racemic mixture.

The methods and formulations described herein include the use of N-oxides (if appropriate), crystalline forms (also known as polymorphs), or pharmaceutically acceptable salts of compounds having the structures presented herein, as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

In some embodiments, the compounds of Formula I, II, III, IV, V, or VI described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

In some embodiments, sites on the compounds of Formula I, II, III, IV, V, or VI disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula I, II, III, IV, V, or VI disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

In some embodiments, compounds described herein, such as compounds of Formula I, II, III, IV V, or VI, are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles and/or nucleophiles to form new functional groups or substituents. Table IA entitled "Examples of Covalent Linkages and Precursors Thereof" lists selected non-limiting examples of covalent linkages and precursor functional groups which yield the covalent linkages. Table IA may be used as guidance toward the variety of electrophiles and nucleophiles combinations available that provide covalent linkages. Precursor functional groups are shown as electrophilic groups and nucleophilic groups.

TABLE IA

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |

TABLE IA-continued

Examples of Covalent Linkages
and Precursors Thereof

| Covalent Linkage Product | Electrophile | Nucleophile |
|---|---|---|
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Alkyl amines | sulfonate esters | amines/anilines |
| hioethers | sulfonate esters | Thiols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

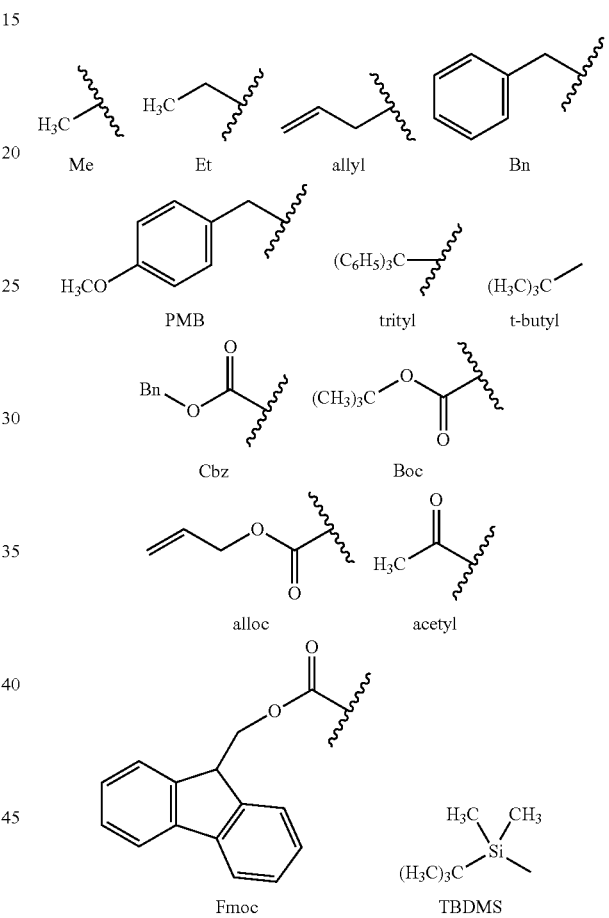

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)═CR$_2$, wherein R refers to the remaining portions of the alkenyl group, which may be the same or different. Non-limiting examples of an alkenyl group include —CH═CH$_2$, —C(CH$_3$)═CH$_2$, —CH═CHCH$_3$, —CH═C(CH$_3$)$_2$ and —C(CH$_3$)═CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

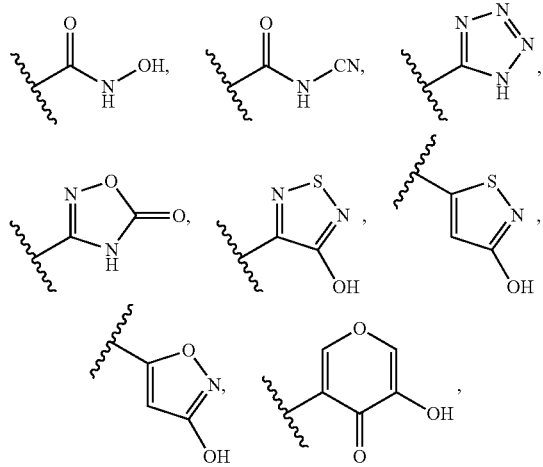

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

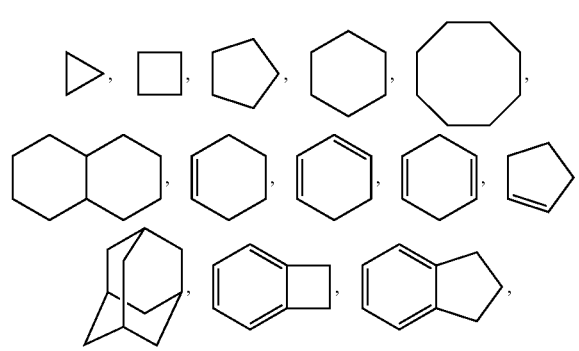

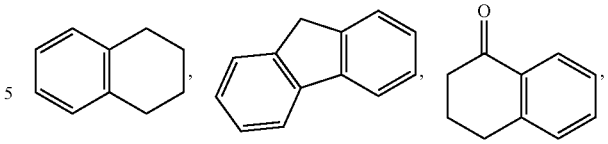

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

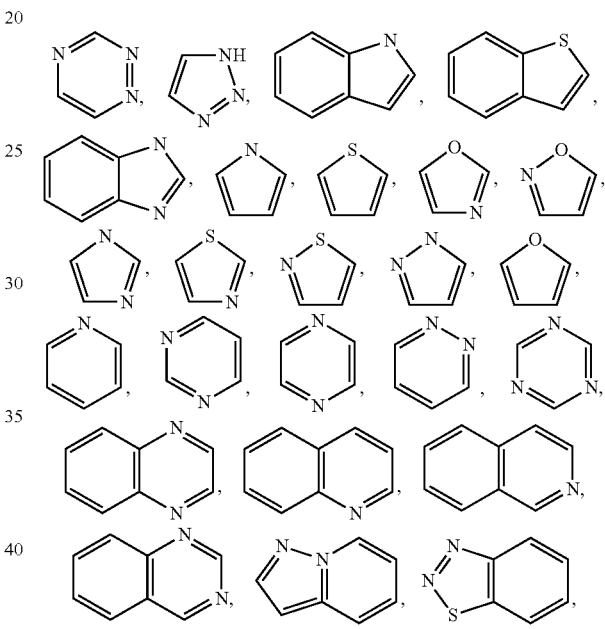

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

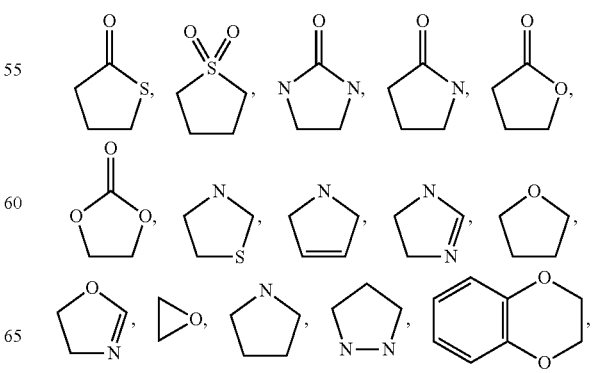

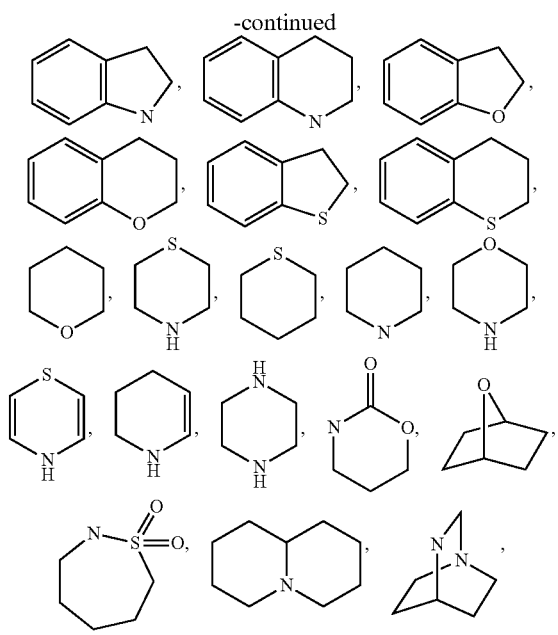

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —CH$_2$Cl, —CF$_3$, —CHF$_2$, —CH$_2$CF$_3$, —CF$_2$CF$_3$, —CF(CH$_3$)$_3$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, C$_1$-C$_6$alkylalkyne, halo, acyl, acyloxy, —CO$_2$H, —CO$_2$-alkyl, nitro, haloalkyl, fluoroalkyl, and amino, including mono- and di-substituted amino groups (e.g. —NH$_2$, —NHR, —N(R)$_2$), and the protected derivatives thereof. By way of example, an optional substituents may be L$^s$R$^s$, wherein each L$^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —(C$_1$-C$_6$alkyl)-, or —(C$_2$-C$_6$alkenyl)-; and each R$^s$ is independently selected from among H, (C$_1$-C$_6$alkyl), (C$_3$-C$_8$cycloalkyl), aryl, heteroaryl, heterocycloalkyl, and C$_1$-C$_6$heteroalkyl. The protecting groups that may form the protective derivatives of the above substituents are found in sources such as Greene and Wuts, above.

The methods and formulations described herein include the use of crystalline forms (also known as polymorphs), or pharmaceutically acceptable salts of compounds having the structure of Formulas I, II, III, IV, V, or VI, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Methods of Treatment and Prevention

In one embodiment, provided herein are methods for stimulation of LXR activity in a cell by contacting the cell with an LXR modulator. Examples of such LXR modulators are described above. Other LXR modulators that can be used to stimulate the LXR activity are identified using screening assays that select for such compounds, as described in detail herein.

Prophylactic Methods

In one aspect, provided herein are methods for preventing skin aging in a subject by administering to the subject an LXR modulator. Administration of a prophylactic LXR modulator can occur prior to the manifestation of skin aging symptoms, such that skin aging is prevented or, alternatively, delayed in its progression.

Therapeutic Methods

In another aspect, provided herein are methods of modulating LXR activity for the treatment of skin aging. Accordingly, in an exemplary embodiment, provided herein are methods which involve contacting a cell with an LXR modulator that induces TIMP1, ASAH1, SPTLC1, SMPD1, LASS2, TXNRD1, GPX3, GSR, CAT, ApoE, ABCA1, ABCA2, ABCA12, ABCA13, ABCG1, and/or decorin expression and/or inhibits TNFα, MMP1, MMP3, and/or IL-8 expression. These methods are performed in vitro (e.g., by culturing the cell with an LXR modulator) or, alternatively, in vivo (e.g., by administering an LXR modulator to a subject). As such, the present methods are directed to treating a subject affected by skin aging that would benefit from induction of TIMP1, ASAH1, SPTLC1, SMPD1, LASS2, TXNRD1, GPX3, GSR, CAT, ApoE, ABCA1, ABCA2, ABCA12, ABCA13, ABCG1, and/or decorin expression and/or inhibition of TNFα, MMP1, MMP3, and/or IL-8 expression.

LXR modulators induce the expression of differential genes in keratinocytes. In human keratinocytes, LXR modulators induce the keratinocyte early differentiation marker involucrin (IVL) as well as late differentiation markers loricrin (LOR), filaggrin (FLG), and transglutaminase 1 (TGM1). The LXR modulator may induce the expression of these genes directly or indirectly.

LXR modulators increase expression of genes involved in fatty acid synthesis and lipid transport in the skin. The LXR ligand induced the expression of genes involved in fatty acid synthesis, namely SREBF1, SREBF2, FASN, and SCD, and genes involved in cholesterol and phospholipid transport namely APOE, APOD, ABCG1, ABCA1, ABCA12, ABCA2, and ABCA13. LXR modulators increase the expression of LASS4 and SMPD2 in skin.

Pharmaceutical Compositions and Methods of Administration of LXR Modulators

LXR modulators are administered to subjects in a biologically compatible form suitable for topical administration to treat or prevent skin aging. By "biologically compatible form suitable for topical administration" is meant a form of the LXR modulator to be administered in which any toxic effects are outweighed by the therapeutic effects of the modulator. The term "subject" is intended to include living organisms in which an immune response can be elicited, for example, mammals. Administration of LXR modulators as described herein can be in any pharmacological form including a therapeutically effective amount of an LXR modulator alone or in combination with a pharmaceutically acceptable carrier.

The therapeutic or pharmaceutical compositions described herein can be administered by any other suitable route known in the art including, for example, oral, intravenous, subcutaneous, intramuscular, or transdermal, or administration to cells in ex vivo treatment protocols. Administration can be either rapid as by injection or over a period of time as by slow infusion or administration of slow release formulation. For treating or preventing skin aging, administration of the therapeutic or pharmaceutical compositions described herein can be performed, for example, by topical administration.

Topical administration of an LXR modulator may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

A therapeutically effective amount of an LXR modulator may vary according to factors such as the skin aging state, age, sex, and weight of the individual, and the ability of the LXR modulator to elicit a desired response in the individual. Dosage regime may be adjusted to provide the optimum cosmetic, response. For example, several divided doses may be administered daily, or the dose may be proportionally reduced as indicated by the exigencies of the skin aging.

LXR modulators can also be linked or conjugated with agents that provide desirable pharmaceutical or pharmacodynamic properties. For example, LXR modulators can be stably linked to a polymer such as polyethylene glycol to obtain desirable properties of solubility, stability, half-life, and other pharmaceutically advantageous properties (see, e.g., Davis et al., Enzyme Eng. 4:169-73 (1978); Burnham N L, Am. J. Hosp. Pharm. 51:210-18 (1994)).

LXR modulators can be in a composition which aids in delivery into the cytosol of a cell. For example, an LXR modulator may be conjugated with a carrier moiety such as a liposome that is capable of delivering the modulator into the cytosol of a cell. Such methods are well known in the art (see, e.g., Amselem S et al., Chem. Phys. Lipids 64:219-37 (1993)).

LXR modulators can be employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the LXR modulator, use thereof in the cosmetic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

In one embodiment, the anti-skin aging compositions disclosed herein can further comprise a retinoic acid receptor (RAR) ligand. Useful RAR ligands include, for example, all-trans retinoic acid (tretinoin) and/or synthetic retinoic acid receptor ligands. Tretinoin is sold under such trademarks as Atragen®, Avita®, Renova®, Retin-A®, Vesanoid®, and Vitinoin®. Exemplary synthetic retinoic acid receptor ligands include tazarotene (Avage®; ethyl 6-[2-(4,4-dimethylthiochroman-6-yl)ethynyl]pyridine-3-carboxylate) and Differin® (adapalene; 6-[3-(1-adamantyl)-4-methoxyphenyl]-2-naphthoic acid; CD271).

Topical compositions can be prepared by combining the anti-skin aging composition with conventional pharmaceutically acceptable diluents and carriers commonly used in topical dry, liquid, cream, and aerosol formulations. Ointment and creams can, for example, be formulated with an aqueous or oily base with the addition of suitable thickening and/or gelling agents. An exemplary base is water. Thickening agents which can be used according to the nature of the base include aluminum stearate, cetostearyl alcohol, propylene glycol, polyethylene glycols, hydrogenated lanolin, and the like. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, for example, talc, lactose, starch, and the like. Drops can be formulated with an aqueous base or non-aqueous base, and can also include one or more dispersing agents, suspending agents, solubilizing agents, and the like.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sun screens, natural retinoids (e.g., retinol), and other additives commonly found in skin treatment compositions.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the LXR modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the LXR modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such LXR modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. LXR modulators that exhibit large therapeutic indices are preferred. While LXR modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such LXR modulators lies preferably within a range of circulating concentrations that include the $ED_{50}$ with little or no toxicity. The dosage may vary within this range depending upon the dosage form employed and the route of administration utilized. For any LXR modulator used in a method described herein, the therapeutically effective dose can be estimated initially from cell culture assays. A dose may be formulated in animal models to achieve a circulating plasma concentration range that includes the $IC_{50}$ (i.e., the concentration of LXR modulator that achieves a half-maximal inhibition of symptoms)

as determined in cell culture. Such information can be used to more accurately determine useful doses in humans. Levels in plasma may be measured, for example, by high performance liquid chromatography.

Monitoring the influence of LXR modulators on the induction of TIMP1, ASAH1, SPTLC1, SMPD1, LASS2, TXNRD1, GPX3, GSR, CAT, ApoE, ABCA1, ABCA2, ABCA12, ABCA13, ABCG1, and/or decorin expression and/or inhibition of TNFα, MMP1, MMP3, and/or IL-8 expression is applied in clinical trials. For example, the effectiveness of an LXR modulator is monitored in clinical trials of subjects exhibiting increased TIMP1, ASAH1, SPTLC1, SMPD1, LASS2, TXNRD1, GPX3, GSR, CAT, ApoE, ABCA1, ABCA2, ABCA12, ABCA13, ABCG1, and/or decorin expression and/or decreased TNFα, MMP1, MMP3, and/or IL-8 expression. In such clinical trials, the expression of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 is used as a "read out" or markers of the different skin aging phenotypes.

Thus, to study the effect of LXR modulators on skin aging, for example, in a clinical trial, cells are isolated and RNA prepared and analyzed for the levels of expression of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8. The levels of gene expression (i.e., a gene expression pattern) is quantified, for example, by Northern blot analysis or RT-PCR, by measuring the amount of protein produced, or by measuring the levels of activity of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8, all by methods well known to those of ordinary skill in the art. In this way, the gene expression pattern serves as a marker, indicative of the physiological response of the cells to the LXR modulator. Accordingly, this response state is determined before, and at various points during, treatment of the individual with the LXR modulator.

Also provided is a method for monitoring the effectiveness of treatment of a subject with an LXR modulator comprising the steps of (i) obtaining a pre-administration sample from a subject prior to administration of the LXR modulator; (ii) detecting the level of expression of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8; (iii) obtaining one or more post-administration samples from the subject; (iv) detecting the level of expression of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 in the post-administration samples; (v) comparing the level of expression of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 in the pre-administration sample with the TIMP1, ABCA12, decorin, TNFα, MMP1, MMP3, and/or IL-8 expression in the post administration sample or samples; and (vi) altering the administration of the LXR modulator to the subject accordingly.

For example, increased administration of the LXR modulator may be desirable to increase TIMP1, ASAH1, SPTLC1, SMPD1, LASS2, TXNRD1, GPX3, GSR, CAT, ApoE, ABCA1, ABCA2, ABCA12, ABCA13, ABCG1, and/or decorin expression to higher levels than detected and/or reduce TNFα, MMP1, MMP3, and/or IL-8 expression to lower levels than detected, that is, to increase the effectiveness of the LXR modulator. Alternatively, decreased administration of the LXR modulator may be desirable to decrease TIMP1, ASAH1, SPTLC1, SMPD1, LASS2, TXNRD1, GPX3, GSR, CAT, ApoE, ABCA1, ABCA2, ABCA12, ABCA13, ABCG1, and/or decorin expression to lower levels than detected or activity and/or to increase TNF, MMP1, MMP3, and/or IL-8 expression to higher levels than detected, that is, to decrease the effectiveness of the LXR modulator. According to such an embodiment, TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 expression may be used as an indicator of the effectiveness of an LXR modulator, even in the absence of an observable phenotypic response.

Furthermore, in the treatment of skin aging, compositions containing LXR modulators are administered exogenously, and it is desirable to achieve certain target levels of LXR modulator in sera, in any desired tissue compartment, and/or in the affected tissue. It is, therefore, advantageous to be able to monitor the levels of LXR modulator in a patient or in a biological sample including a tissue biopsy sample obtained from a patient and, in some cases, also monitoring the levels of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 expression. Accordingly, also provided herein are methods for detecting the presence of LXR modulator in a sample from a patient using techniques described herein.

Screening Assays

In one embodiment, expression levels of cytokines and metalloproteases described herein are used to facilitate design and/or identification of compounds that treat skin aging through an LXR-based mechanism. Accordingly provided herein are methods (also referred to herein as "screening assays") for identifying modulators, i.e., LXR modulators, that have a stimulatory or inhibitory effect on, for example, TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 expression. Compounds thus identified are used as anti-skin aging compounds as described elsewhere herein.

An exemplary screening assay is a cell-based assay in which a cell that expresses LXR is contacted with a test compound, and the ability of the test compound to modulate TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 expression through an LXR-based mechanism. Determining the ability of the test compound to modulate TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8 expression is accomplished by monitoring, for example, DNA, mRNA, or protein levels, or by measuring the levels of activity of TIMP1, ASAH1, SPTLC1, SMPD1, LASS2, TXNRD1, GPX3, GSR, CAT, ApoE, ABCA1, ABCA2, ABCA12, ABCA13, ABCG1, decorin, TNFα, MMP1, MMP3, and/or IL-8. The cell, for example, is of mammalian origin, e.g., human.

Novel modulators identified by the above-described screening assays are used for treatments as described herein.

EXAMPLES

The following examples are offered for purposes of illustration, and are not intended to limit the scope of the

109 claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1

Synthesis of Intermediate 3-(methylsulfonyl)benzohydrazide (3)

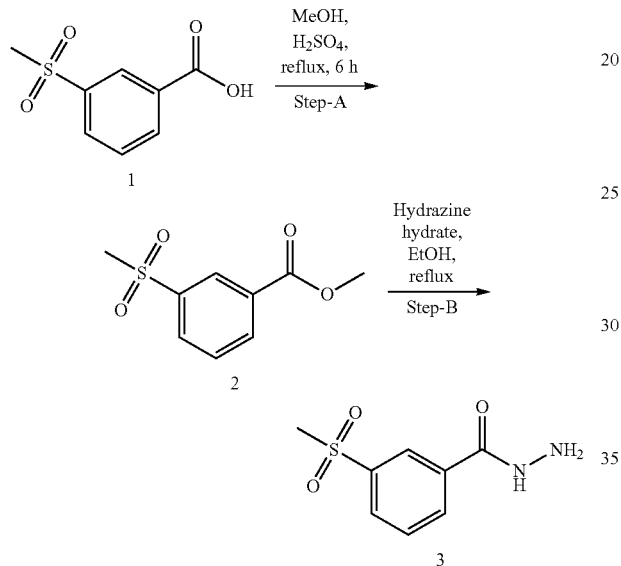

Step A: Synthesis of methyl 3-(methylsulfonyl)benzoate (2)

To a stirred solution of 3-(methylsulfonyl)benzoic acid (1) (1.5 g, 7.5 mmol) in methanol (25 mL) sulfuric acid (1.5 mL) was added and the reaction mixture was heated to reflux for 8 h. On completion, solvent was removed, diluted with water (40 mL) and extracted with ethyl acetate (60 mL×3). The combined organic layer was washed saturated sodium bicarbonate solution, brine, dried over sodium sulphate and concentrated to afford the title compound 2 (1.6 g, 99%) which was used for further reaction.

Step B: Synthesis of 3-(methylsulfonyl)benzohydrazide (3)

A stirred solution of compound 2 (2.1 g, 9.8 mmol) and hydrazine hydrate (2.4 mL, 49.0 mmol) in ethanol (70 mL) was heated to reflux for 8 h. On completion, solvent was removed, diluted with water (30 mL) and extracted with 10% methanol in dichloromethane (60 mL×4). The combined organic layer was washed with brine, dried over sodium sulphate and concentrated to afford the title compound 3 (2.0 g, 91%) which was used for further reaction.

110

Example 2

Synthesis of 1-(2-chlorophenyl)-5-(5-(3-(methylsulfonyl)phenyl)-1,3,4-thiadiazol-2-yl)-1H-pyrazole-3-carboxylic acid (10)

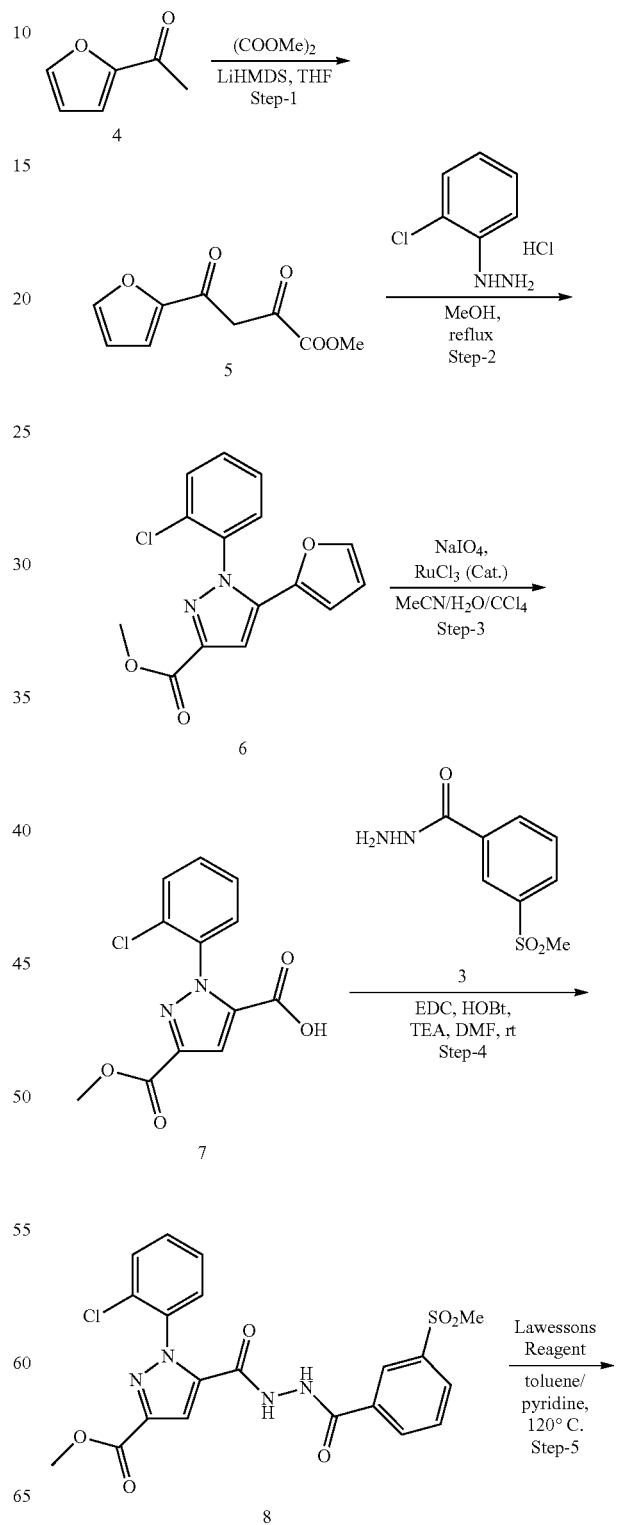

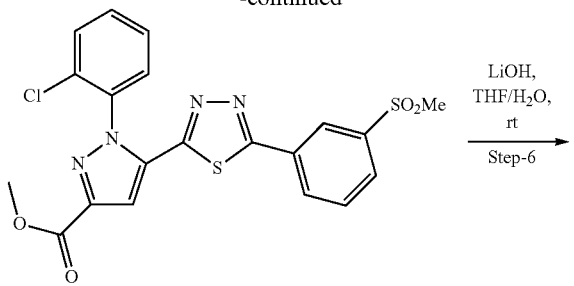

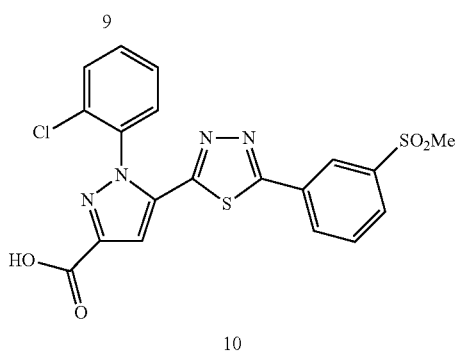

Step 1: Synthesis of methyl 4-(furan-2-yl)-2,4-dioxobutanoate (5)

To a stirred solution of compound 4 (5 g, 45.0 mmol) in THF (100 mL) at −78° C., LiHMDS (58.5 mL, 58.5 mmol) was added drop wise. After 30 min, a solution of dimethyl oxalate (7.9 g, 67.5 mmol) in THF (20 mL) was added. The reaction mixture was allowed to attain the room temperature in cooling bath gradually and stirred overnight. Solvent was removed, water (100 mL) added, extracted with ethyl acetate (50 mL×3). Combined organic layer was washed with brine, dried over sodium sulphate and concentrated to afford the title compound 5 (8.0 g, 89.9%) which was used for further reaction.

Step 2: Synthesis of methyl 1-(2-chlorophenyl)-5-(furan-2-yl)-1H-pyrazole-3-carboxylate (6)

A stirred solution compound 5 (10.0 g, 50 mmol) and (2-chlorophenyl)hydrazine hydrochloride (10.0 g, 56 mmol) in methanol 80 mL was heated to reflux for 6 h. On cooling to 0° C., solid crashed out, filtered and washed with cold methanol to afford the title compound 6 (12.0 g, 80.0%) which was used for further reaction.

Step 3: Synthesis of 1-(2-chlorophenyl)-3-(methoxycarbonyl)-1H-pyrazole-5-carboxylic acid (7)

To a stirred mixture of compound 6 (3.0 g, 9.9 mmol) in a mixture of acetonitrile (60 mL), water (80 mL) and carbon tetrachloride (60 mL) was added sodium periodate (8.3 g, 39 mmol) and ruthenium chloride (125 mg, 0.03 mmol) and the reaction mixture was stirred at room temperature for 72 h. On completion, solvent was removed, crude mass was dissolved in saturated sodium bicarbonate solution, extracted with ether (50 ml×3). Aqueous layer was acidified with 1N HCl and extracted with ethyl acetate (60 mL×4). The combined ethyl acetate layer was washed with brine, dried over sodium sulphate and concentrated to afford the title compound 7 (1.2 g, 44%) which was used for further reaction.

Step 4: Synthesis of methyl 1-(2-chlorophenyl)-5-(2-(3-(methylsulfonyl)benzoyl) hydrazinocarbonyl)-1H-pyrazole-3-carboxylate (8)

To a stirred solution of compound 7 (500 mg, 1.78 mmol) in DMF (20 mL at 0° C., EDCI (500 mg, 2.6 mm01) was added and stirred for 15 min. HOBt (351 mg, 2.6 mmol) was added to the reaction mixture and after 30 min stirring 3-(methylsulfonyl)benzohydrazide 3 from Example 1 (450 mg, 2.1 mmol) was added. Reaction mixture was allowed to attain room temperature and stirred for over night. Water (100 mL) was added to the reaction mixture and extracted with ethyl acetate (50 mL×4). Combined organic layer was washed with water, brine, dried over sodium sulphate and concentrated. The crude product on column chromatographic purification using 2% methanol in dichloromethane afforded the title compound 8 (452 mg, 52%).

Step 5: Synthesis of methyl 1-(2-chlorophenyl)-5-(5-(3-(methylsulfonyl)phenyl)-1,3,4-thiadiazol-2-yl)-1H-pyrazole-3-carboxylate (9)

To a stirred mixture of compound 8 (500 mg, 1.05 mmol) and Lawesson's reagent (637 mg, 1.57 mmol) in toluene (10 mL) was added pyridine (0.15 mL) and the reaction mixture was heated to reflux for 3 h. On completion, solvent was removed and the crude reaction mixture on column chromatographic purification using 0.5% methanol in dichloromethane the title compound 9 (250 mg, 51%). LCMS: 475.15 (M+1)$^+$; HPLC: 94.29% (@210 nm-370 nm) ($R_t$; 6.771; Method: Column: YMC ODS-A 150 mm×4.6 mm×5; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (CDCl$_3$, 400 MHz) δ 8.38 (s, 1H), 8.23 (d, 1H, J=7.6 Hz), 8.06 (d, 1H, J=7.6 Hz), 7.70 (t, 1H, J=8&7.6 Hz), 7.66 (s, 1H), 7.62-7.50 (m, 4H), 4.00 (s, 3H), 3.09 (s, 3H).

Step 6: Synthesis of 1-(2-chlorophenyl)-5-(5-(3-(methylsulfonyl)phenyl)-1,3,4-thiadiazol-2-yl)-1H-pyrazole-3-carboxylic acid (10)

To a stirred solution of compound 9 (120 mg, 0.25 mmol) in THF (6.0 mL) at room temperature, a solution of lithium hydroxide (52 mg, 1.25 mmol) in water (6.0 mL) was added and stirring continued for 2 h. On completion, solvent was removed, diluted with water (20 mL) and washed with ether (30 mL×3). The aqueous layer was acidified with 1N HCl and extracted with 10% methanol in dichloromethane (50 mL×3). Combined organic layer was washed brine, dried over sodium sulphate and concentrated. The crude product after ether and pentane washing furnished the title compound 10 (80 mg, 69%). LCMS: 461.25 (M+1)$^+$; HPLC: 94.34% (@210 nm-370 nm) ($R_t$; 5.989; Method: Column: YMC ODS-A 150 nmm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 8.39 (s, 1H), 8.24 (d, 1H, J=8 Hz), 8.12 (d, 1H, J=8 Hz), 7.85-7.60 (m, 6H), 3.30 (s, 3H).

Example 3

Synthesis of 1-(2-chlorophenyl)-5-(5-(3-(methylsulfonyl)phenyl)-1,3,4-oxadiazol-2-yl)-1H-pyrazole-3-carboxylic acid (12)

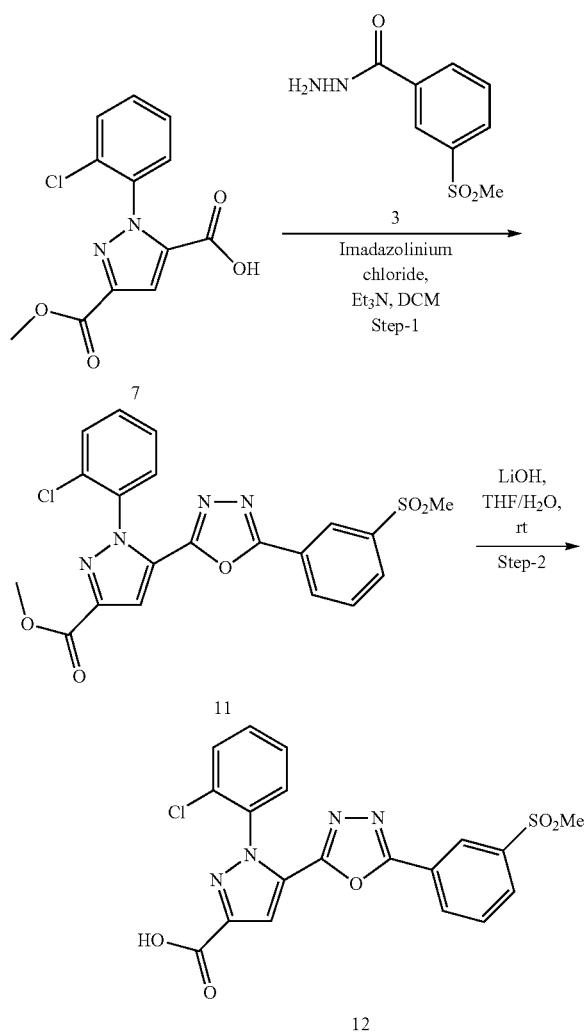

Step 1: Synthesis of methyl 1-(2-chlorophenyl)-5-(5-(3-(methylsulfonyl)phenyl)-1,3,4-oxadiazol-2-yl)-1H-pyrazole-3-carboxylate (11)

To an ice cooled stirred solution of compound 7 from Example 2 (750 mg, 2.67 mmol) and 3-(methylsulfonyl) benzohydrazide 3 from Example 1 (575 mg, 2.67 mmol) in dichloromethane (25 mL) was added imidazolinium chloride (902 mg, 5.34 mmol) and stirred for 30 min. Triethyl amine (1.5 mL, 10.68 mmol) was added to the reaction mixture slowly over a period of 30 min, allowed to attain room temperature and stirring continued for over night. Water (50 mL) added to the reaction mixture and extracted with 10% methanol in dichloromethane (50 mL×3). The combined organic layer was washed saturated sodium bicarbonate solution, brine, dried over sodium sulphate and concentrated. The crude reaction mixture on column chromatographic purification using 2% methanol in dichloromethane afforded the title compound 11 (350 mg, 50%). LCMS: 459.25 (M+1)$^+$; HPLC: 93.72% (@210 nm-370 nm) (R$_t$: 6.704; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (CDCl$_3$, 400 MHz) δ 8.28 (s, 1H), 8.26 (d, 1H), 8.11 (d, 1H, J=7.6 Hz), 7.75-7.71 (m, 2H), 7.62-7.50 (m, 4H), 4.02 (s, 3H), 3.09 (s, 3H).

Step 2: Synthesis of 1-(2-chlorophenyl)-5-(5-(3-(methylsulfonyl)phenyl)-1,3,4-oxadiazol-2-yl)-1H-pyrazole-3-carboxylic acid (12)

To a stirred solution of compound 11 (100 mg, 0.21 mmol) in THF (4.0 mL) at room temperature, a solution of lithium hydroxide (44 mg, 1.05 mmol) in water (4.0 mL) was added and stirring continued for 2 h. On completion, solvent was removed, diluted with water (20 mL) and washed with ether (30 mL×3). The aqueous layer was acidified with 1N HCl and extracted with 10% methanol in dichloromethane (50 mL×3). Combined organic layer was washed brine, dried over sodium sulphate and concentrated. The crude product after ether and pentane washing furnished the title compound 12 (30 mg, 31%). LCMS: 445.10 (M+1)$^+$; HPLC: 96.20% (@210 nm-370 nm) (R$_t$: 5.847; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (CDCl$_3$, 400 MHz) δ 8.29 (s, 1H), 8.27 (d, 1H), 8.12 (d, 1H, J=7.6 Hz), 7.79 (s, 1H), 7.74 (t, 1H, J=7.6&7.2 Hz), 7.64-7.50 (m, 4H), 3.10 (s, 3H).

Example 4

Synthesis of ethyl 2-(5-(5-(3-(methylsulfonyl)phenyl)thiophen-2-yl)-3-(trifluoromethyl)-1H-pyrazol-1-yl)acetate (16)

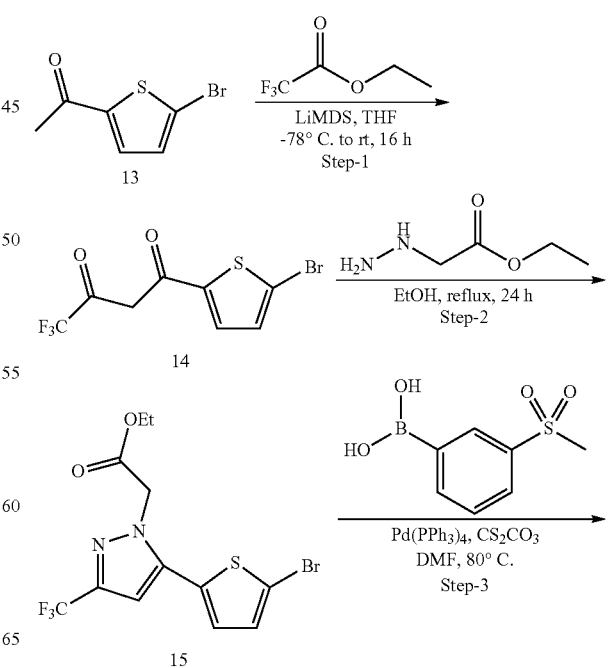

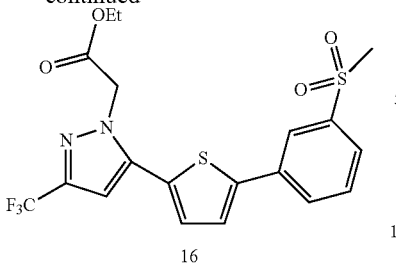

16

Step 1: Synthesis of 1-(5-bromothiophen-2-yl)-4,4,4-trifluorobutane-1,3-dione (14)

To a stirred solution of compound 13 (5.0 g, 24.0 mmol) in THF (50 mL) at −78° C., LiHMDS (37 mL, 36.0 mmol) was added dropwise. After 30 min, a solution of dimethyl oxalate (2.7 g, 36.0 mmol) in THF (20 mL) was added. The reaction mixture was allowed to gradually return to room temperature in a cooling bath and stirred overnight. Solvent was removed, water (100 mL) added, and the solution extracted with ethyl acetate (50 mL×3). Combined organic layers were washed with brine, dried over sodium sulphate and concentrated to afford the crude compound 14 (6.0 g, 82.1%) which was used without purification for subsequent reactions.

Step 2: Synthesis of ethyl 2-(5-(5-bromothiophen-2-yl)-3-(trifluoromethyl)-1H-pyrazol-1-yl)acetate (15)

A stirred solution compound 14 (5.2 g, 17.0 mmol) and ethyl 2-hydrazinylacetate (2.94 g, 19.0 mmol) in methanol (60 mL) was heated to reflux for 1.5 h. On cooling to room temperature, solvent was removed, water (100 mL) added and the solution extracted with ethyl acetate (50 mL×3). Combined organic layers were washed with brine, dried over sodium sulphate and concentrated. The crude product was purified by column chromatography using 10% ethyl acetate in hexane to afford compound 15 (1.5 g) and which was used for further reactions.

Step 3: Synthesis of ethyl 2-(5-(5-(3-(methylsulfonyl)phenyl)thiophen-2-yl)-3-(trifluoromethyl)-1H-pyrazol-1-yl)acetate (16)

A stirred solution of compound 15 (1.5 g, 3.9 mmol) and 3-(methylsulfonyl)phenylboronic acid (1.2 g, 5.8 mmol) in DMF (10 mL) was degassed with argon. Tetrakis(triphenylphosphine)palladium(0) (450 mg, 0.3 mmol) was added and the reaction degassed for 30 min. Sodium carbonate (1.03 g, 9.0 mmol) was added to the reaction mixture, the reaction was degassed with argon for 30 min and heated to 90° C. for 3 h. Solvent was removed and the reaction mixture diluted with water (30 mL) and extracted with ethyl acetate (50 mL×3). The combined organic layers were washed with saturated brine, dried over sodium sulphate and concentrated. The crude reaction mixture was purified by column chromatography using 30% ethyl acetate in hexane to afford 16 (1.2 g, 67%). LCMS: 459.20 (M+1)$^+$; $^1$H NMR (DMSO-d$_6$, 400 MHz) δ 8.13 (s, 1H), 8.05 (d, 1H, J=7.6 Hz), 7.91 (d, 1H, J=7.6 Hz), 7.82 (d, 1H, J=4 Hz), 7.75 (t, 2H, J=7.6 Hz) 7.20 (s, 1H), 5.40 (s, 2H), 4.01-4.23 (m, 2H), 3.32 (s, 3H), 1.1-1.25 (m, 3H).

Example 5

Synthesis of ethyl 2-(4-bromo-5-(5-(3-(methylsulfonyl)phenyl)thiophen-2-yl)-3-(trifluoromethyl)-1H-pyrazol-1-yl)acetate (17)

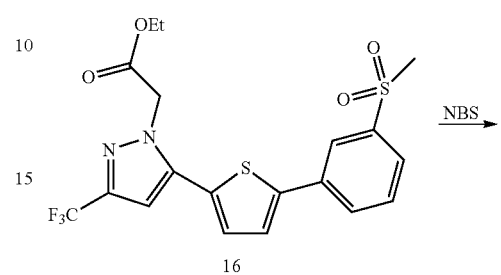

16

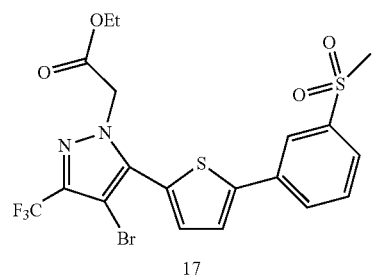

17

Following bromination with N-bromosuccinimide, the title compound 17 is prepared starting from ethyl 2-(5-(5-(3-(methylsulfonyl)phenyl)thiophen-2-yl)-3-(trifluoromethyl)-1H-pyrazol-1-yl)acetate 16.

Example 6

Synthesis of 2-(dimethylamino)ethyl 2-(5-(5-(3-(methylsulfonyl)phenyl)thiophen-2-yl)-3-(trifluoromethyl)-1H-pyrazol-1-yl)acetate (19)

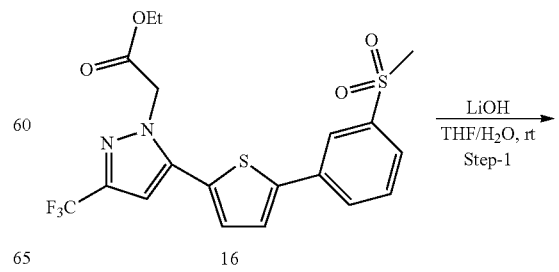

16

117

-continued

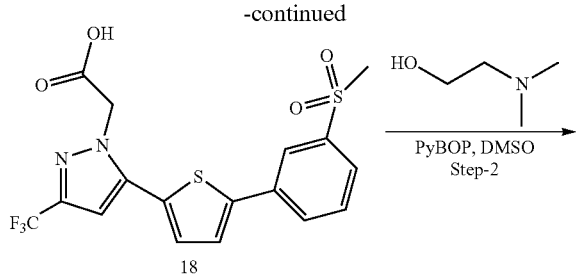

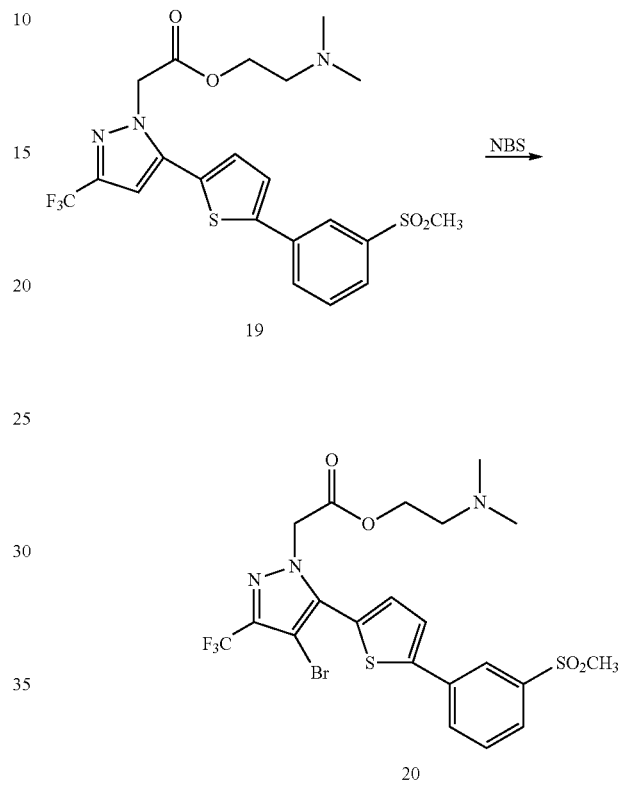

Step 1: Synthesis of methyl 2-(5-(5-(3-(methylsulfonyl)phenyl)thiophen-2-yl)-3-(trifluoromethyl)-1H-pyrazol-1-yl)acetic acid) (18)

To a stirred solution of 16 (1.2 g, 2.62 mmol) in THF (4.0 mL) at room temperature, was added a solution of lithium hydroxide (94 mg, 3.930 mmol) in water (4.0 mL) and stirring continued for 2 h. On completion, the solvent was removed, reaction mixture diluted with water (20 mL) and washed with ether (30 mL×3). The aqueous layer was acidified with 1N HCl and extracted with 10% methanol in dichloromethane (50 mL×3). Combined organic layer was washed with brine, dried over sodium sulphate and concentrated. The crude product after ether and pentane washing afforded 18 (700 mg, 63%). LCMS: 431.15 (M+1)$^+$; $^1$H NMR (DMSO-d$_6$, 400 MHz) δ13.6 (s, 1H), 8.15 (s, 1H), 8.05 (d, 1H, J=7.6 Hz), 7.91 (d, 1H, J=8 Hz), 7.81 (d, 2H, J=3.6 Hz), 7.76 (t, 1H, J=7.6 Hz), 7.16 (s, 1H), 5.23 (s, 2H), 3.35 (s, 3H).

Step 2: Synthesis of 2-(dimethylamino)ethyl 2-(5-(5-(3-(methylsulfonyl)phenyl)thiophen-2-yl)-3-(trifluoromethyl)-1H-pyrazol-1-yl)acetate (19)

To a stirred solution of compound 18 (0.2 g, 0.471 mmol), 2-(dimethylamino)ethanol (0.14 mL, 1.41 mmol) and triethylamine (0.13 mL, 0.942 mmol) in DMSO (5 ml) at RT was added Pybop (0.360 g, 0.706 mmol) and the reaction mixture stirred overnight. The reaction was then diluted with water (30 mL) and extracted with ethyl acetate (50 mL×3). The combined organic layer was washed with saturated brine, dried over sodium sulphate and concentrated. The crude reaction mixture was purified by column chromatography using 3% methanol in dichloromethane to afford 19 (15 mg, 6%).

118

Example 7

Synthesis of 2-(dimethylamino)ethyl 2-(4-bromo-5-(5-(3-(methylsulfonyl)phenyl)thiophen-2-yl)-3-(trifluoromethyl)-1H-pyrazol-1-yl)acetate (20)

Following bromination with N-bromosuccinimide, the title compound 20 is prepared starting from 2-(dimethylamino)ethyl 2-(5-(5-(3-(methylsulfonyl)phenyl)thiophen-2-yl)-3-(trifluoromethyl)-1H-pyrazol-1-yl)acetate 19.

Example 8

Synthesis of methylthiomethyl 2-(5-(5-(3-(methylsulfonyl)phenyl)thiophen-2-yl)-3-(trifluoromethyl)-1H-pyrazol-1-yl)acetate (21)

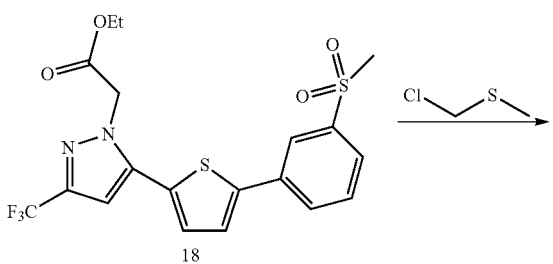

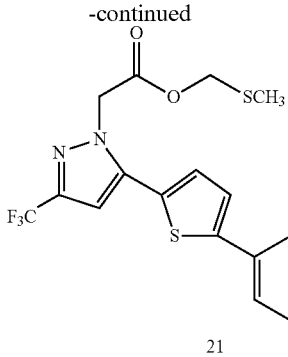

21

A stirred mixture of compound 18 (0.3 g, 0.690 mmol), (chloromethyl)(methyl)sulfane (0.269 g, 2.79 mmol) and potassium carbonate (0.480 g, 3.48 mmol) in DMF (5 mL),) was heated to 100° C. for 10 h, diluted with water (30 mL) and extracted with ethyl acetate (50 mL×3). The combined organic layer was washed with saturated brine, dried over sodium sulphate, and concentrated. The crude reaction mixture was purified by Prep HPLC to afford 21 (0.020 g, 6%). LCMS: 491.20 (M+1)$^+$; $^1$H NMR (DMSO-d$_6$, 400 MHz) δ 13.6 (s, 1H), 8.18 (s, 1H), 8.08 (d, 1H, J=8 Hz), 7.92 (d, 1H, J=8 Hz), 7.85 (d, 1H, J=3.6 Hz), 7.75 (t, 1H), 7.50 (d, 2H), 5.6-5.3 (m, 2H), 3.4-3.20 (m, 5H), 1.84 (s, 3H).

Example 9

Synthesis of methylthiomethyl 2-(4-bromo-5-(5-(3-(methylsulfonyl)phenyl)thiophen-2-yl)-3-(trifluoromethyl)-1H-pyrazol-1-yl)acetate (22)

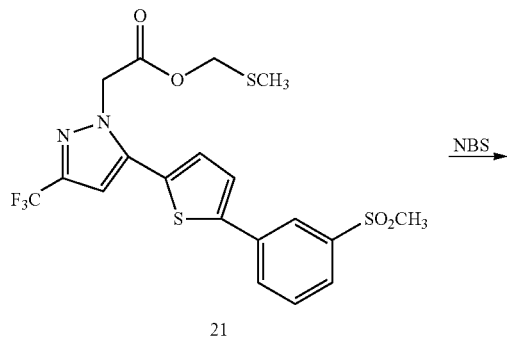

21

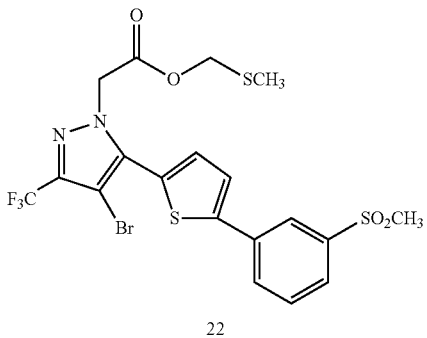

22

Following bromination with N-bromosuccinimide, the title compound 22 is prepared starting from methylthiomethyl 2-(5-(5-(3-(methylsulfonyl)phenyl)thiophen-2-yl)-3-(trifluoromethyl)-1H-pyrazol-1-yl)acetate 21.

Example 10

Synthesis of ethyl 2-(5-(5-(3-(methylsulfonyl)phenyl)-1H-pyrrol-2-yl)-3-(trifluoromethyl)-1H-pyrazol-1-yl)acetate (26)

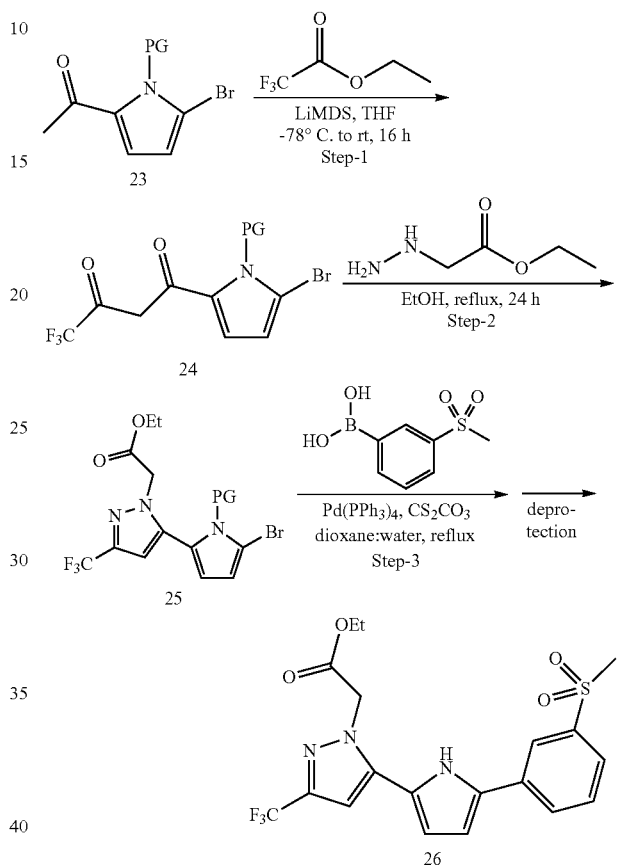

Following the reaction sequence above, the title compound 26 is prepared starting from a suitably protected pyrrole 23.

Example 11

Synthesis of ethyl 2-(5-(4-bromo-5-(3-(methylsulfonyl)phenyl)-1H-pyrrol-2-yl)-3-(trifluoromethyl)-1H-pyrazol-1-yl)acetate (27)

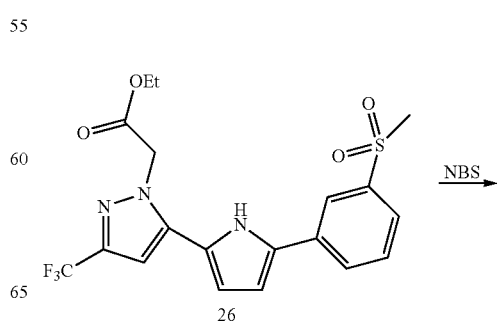

26

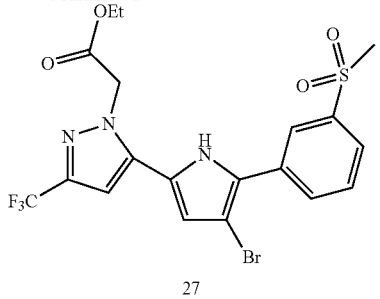

Following bromination with N-bromosuccinimide, the title compound 27 is prepared starting from ethyl 2-(5-(5-(3-(methylsulfonyl)phenyl)-1H-pyrrol-2-yl)-3-(trifluoromethyl)-1H-pyrazol-1-yl)acetate 26.

Example 12

Synthesis of 2-(dimethylamino)ethyl 2-(5-(5-(3-(methylsulfonyl)phenyl)-1H-pyrrol-2-yl)-3-(trifluoromethyl)-1H-pyrazol-1-yl)acetate (29)

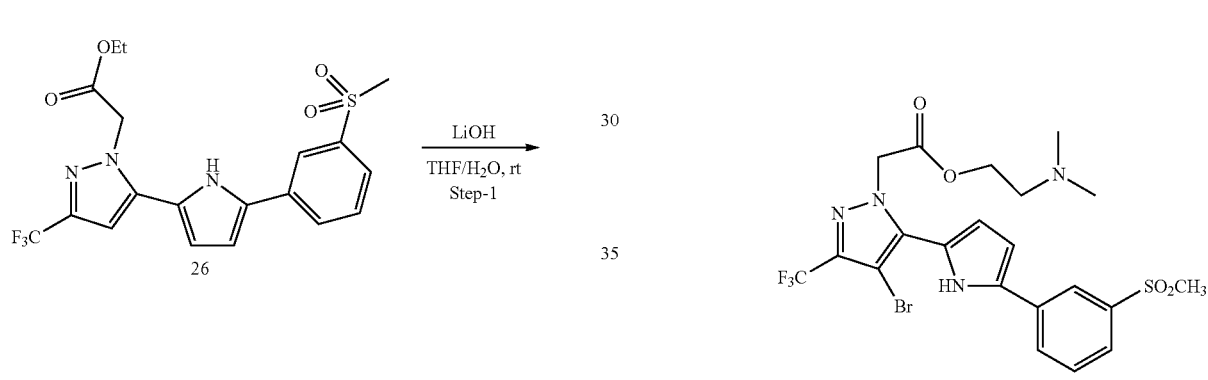

Following the two step reaction sequence above, the title compound 29 is prepared starting from ethyl 2-(5-(5-(3-(methylsulfonyl)phenyl)-1H-pyrrol-2-yl)-3-(trifluoromethyl)-1H-pyrazol-1-yl)acetate 26.

Example 13

Synthesis of 2-(dimethylamino)ethyl 2-(4-bromo-5-(5-(3-(methylsulfonyl)phenyl)thiophen-2-yl)-3-(trifluoromethyl)-1H-pyrazol-1-yl)acetate (30)

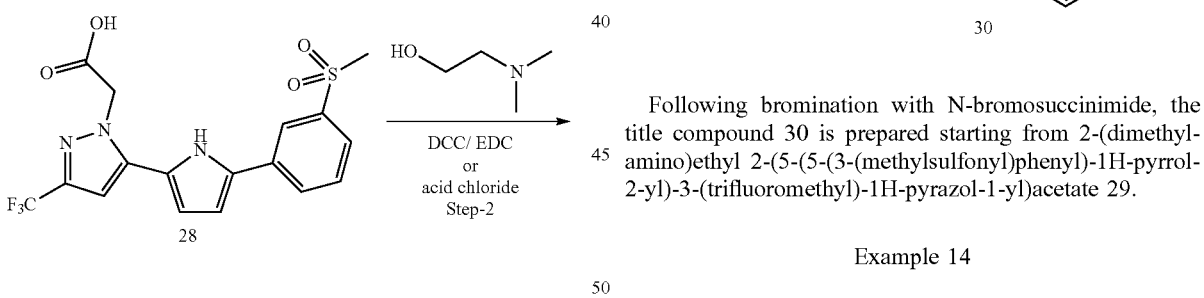

Following bromination with N-bromosuccinimide, the title compound 30 is prepared starting from 2-(dimethylamino)ethyl 2-(5-(5-(3-(methylsulfonyl)phenyl)-1H-pyrrol-2-yl)-3-(trifluoromethyl)-1H-pyrazol-1-yl)acetate 29.

Example 14

Synthesis of methylthiomethyl 2-(5-(5-(3-(methylsulfonyl)phenyl)-1H-pyrrol-2-yl)-3-(trifluoromethyl)-1H-pyrazol-1-yl)acetate (31)

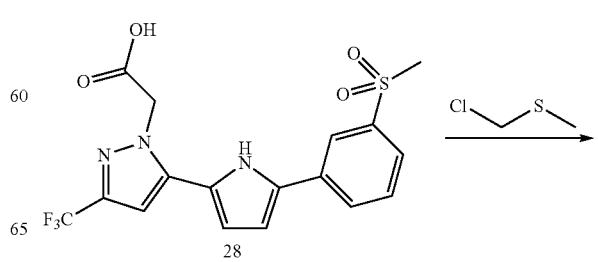

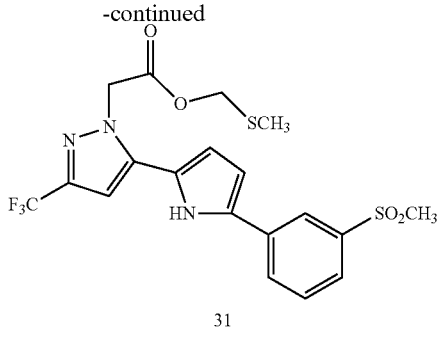

31

Following alkylation, the title compound 31 is prepared starting from 2-(5-(5-(3-(methylsulfonyl)phenyl)-1H-pyrrol-2-yl)-3-(trifluoromethyl)-1H-pyrazol-1-yl)acetic acid 28.

Example 15

Synthesis of methylthiomethyl 2-(4-bromo-5-(5-(3-(methylsulfonyl)phenyl)-1H-pyrrol-2-yl)-3-(trifluoromethyl)-1H-pyrazol-1-yl)acetate (32)

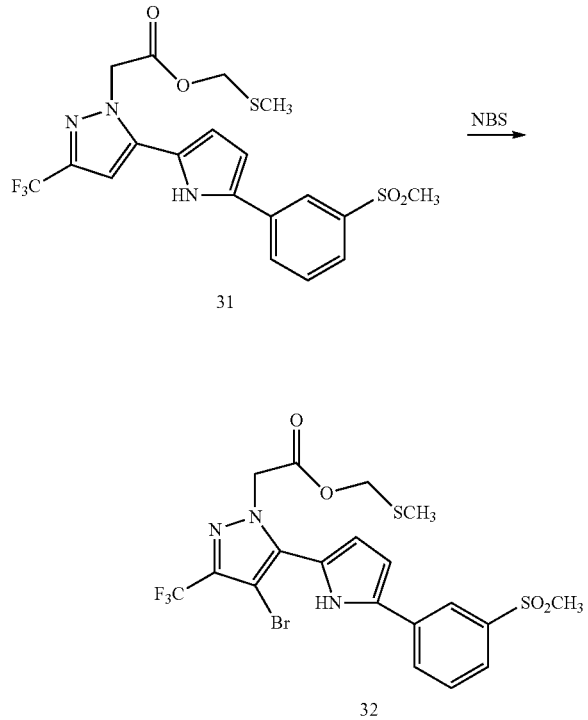

Following bromination with N-bromosuccinimide, the title compound 32 is prepared starting from methylthiomethyl 2-(5-(5-(3-(methylsulfonyl)phenyl)-1H-pyrrol-2-yl)-3-(trifluoromethyl)-1H-pyrazol-1-yl)acetate 31.

Example 16

Synthesis of ethyl 2-(5-(3'-(methylsulfonyl)biphenyl-4-yl)-3-(trifluoromethyl)-1H-pyrazol-1-yl)acetate (36)

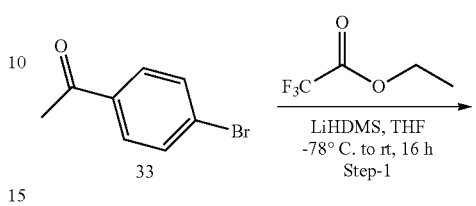

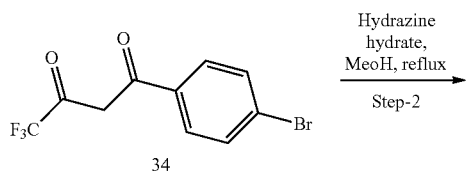

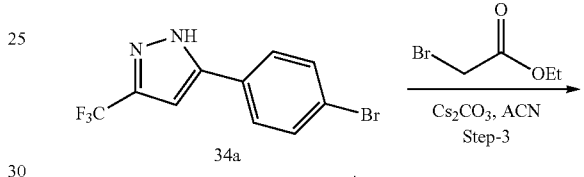

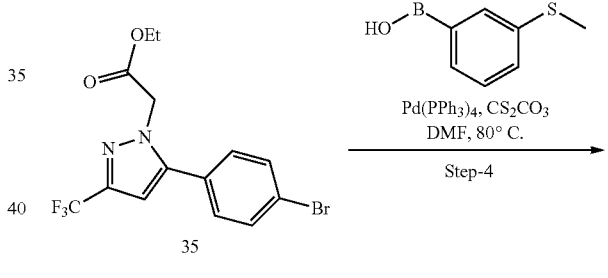

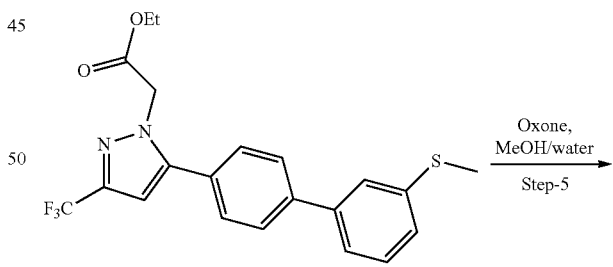

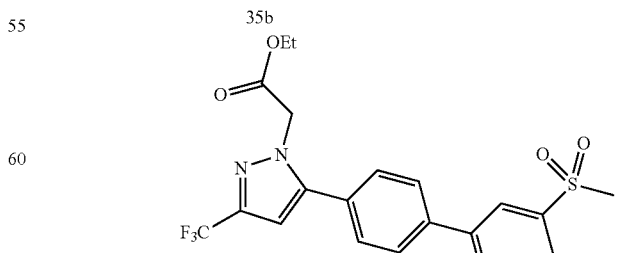

Step 1: Synthesis of 1-(4-bromophenyl)-4,4,4-trifluorobutane-1,3-dione (34)

To a stirred solution of compound 33 (15.0 g, 76.0 mmol) in THF (50 mL) at −78° C., LiHMDS (114 mL, 114.0 mmol) was added dropwise. After 30 min, a solution of dimethyl oxalate (13.6 ml, 114.0 mmol) in THF (100 mL) was added. The reaction mixture was allowed to gradually come to room temperature in a cooling bath and stirred overnight. Solvent was removed, water (100 mL) added, and the mixture was extracted with ethyl acetate (50 mL×3). Combined organic layer was washed with brine, dried over sodium sulphate and concentrated to afford compound 34 (16 g, 71%) which was used without purification in subsequent reactions.

Step 2: Synthesis of 5-(4-bromophenyl)-3-(trifluoromethyl)-1H-pyrazole (34a)

A stirred solution of compound 34 (15.0 g, 50.0 mmol) and hydrazine hydrate (10.0 g, 56 mmol) in methanol 150 mL was heated to reflux for 1 h. After cooling in an ice bath for 10 min, the solvent was removed, water (100 mL) added, and the reaction mixture extracted with ethyl acetate (50 mL×3). Combined organic layer was washed with brine, dried over sodium sulphate and concentrated crude. The crude product was purified by column chromatography using 10% ethyl acetate in hexane, to afford the crude pyrazole intermediate 34a.

Step 3: Synthesis of ethyl 2-(5-(4-bromophenyl)-3-(trifluoromethyl)-1H-pyrazol-1-yl)acetate (35)

To 6 g of 34a in acetonitrile (150 mL) was added cesium carbonate (13.5 g, 41 mmol) followed by ethylbromoacetate (1.3 mL, 30 mmol) and the reaction mixture heated to 80° C. for 6 h. On completion, the solvent was removed, water (100 mL) added and the crude reaction mixture extracted with ethyl acetate (50 mL×3). Combined organic layer was washed with brine, dried over sodium sulphate and concentrated. The crude product was purified by column chromatography using 10% ethyl acetate in hexane to afford 35 (2 g, 26%).

Step 4: Synthesis of ethyl 2-(5-(3'-(methylsulfonyl)-[1,1'-biphenyl]-4-yl)-3-(trifluoromethyl)-1H-pyrazol-1-yl)acetate (35b)

A stirred solution of compound 35 (1.6 g, 4.0 mmol) and (3-(methylthio)phenyl)boronic acid (1.06 g, 6.0 mmol) in DMF (20 mL) was degassed with argon. Tetrakis(triphenylphosphine)palladium(0) (462 mg, 0.4 mmol) was added and the reaction again degassed for 30 min. Sodium carbonate (1.06 g, 10.0 mmol) was added to the reaction mixture, and the reaction was again degassed with argon for another 30 min. The reaction mixture was heated to 90° C. for 3 h. Solvent was removed, the reaction mixture diluted with water (30 mL) and extracted with ethyl acetate (50 mL×3). The combined organic layer was washed with saturated brine, dried over sodium sulphate and concentrated. The crude reaction mixture was purified by column chromatography using 30% ethyl acetate in hexane to afford 35b (1.5 g, 99%).

Step 5: Synthesis of ethyl 2-(5-(3'-(methylsulfonyl)-[1,1'-biphenyl]-4-yl)-3-(trifluoromethyl)-1H-pyrazol-1-yl)acetate (36)

To a stirred solution of 35b (1.5 g, 3.5 mmol) in methanol (20.0 mL) and water (20 mL) at room temperature, was added oxone (5.46 g, 8.9 mmol) and stirring continued for 1.5 h. On completion, solvent was removed and the reaction mixture diluted with water (30 mL) and extracted with ethyl acetate (50 mL×3). The combined organic layer was washed with saturated brine, dried over sodium sulphate and concentrated. The crude reaction mixture was purified by column chromatography using 50% ethyl acetate in hexane to afford 36 (1.3 g, 81%). LCMS: 453.20 (M+1)$^+$; $^1$H NMR (CD$_3$OD, 400 MHz) δ 8.24 (s, 1H), 8.04 (d, 1H, J=7.6 Hz), 7.99 (d, 1H, J=8.4 Hz), 7.86 (d, 1H, J=8 Hz), 7.77 (m, 1H, J=8.4 Hz), 7.62 (d, 2H, J=8.4 Hz), 7.62 (d, 2H, J=8.4 Hz), 6.80 (s, 1H), 5.09 (s, 1H), 4.25-4.15 (m, 2H), 3.19 (s, 3H), 1.25-1.2 (m, 3H).

Example 17

Synthesis of ethyl 2-(4-bromo-5-(3'-(methylsulfonyl)biphenyl-4-yl)-3-(trifluoromethyl)-1H-pyrazol-1-yl)acetate (37)

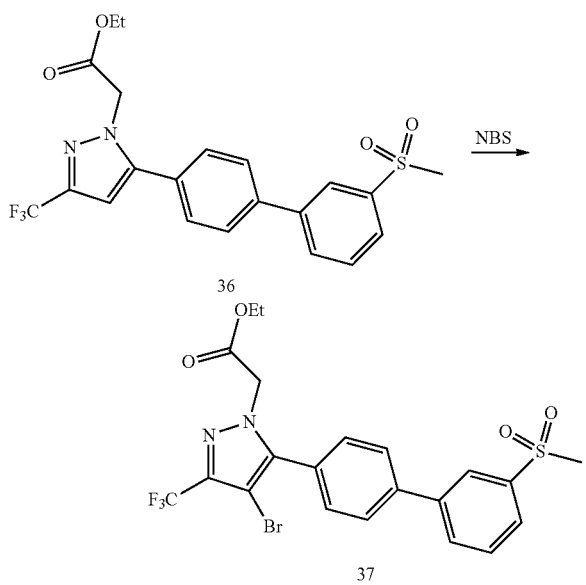

Following bromination with N-bromosuccinimide, the title compound 37 is prepared starting from ethyl 2-(5-(3'-(methylsulfonyl)biphenyl-4-yl)-3-(trifluoromethyl)-1H-pyrazol-1-yl)acetate 36.

Example 18

Synthesis of 2-(dimethylamino)ethyl 2-(5-(3'-(methylsulfonyl)biphenyl-4-yl)-3-(trifluoromethyl)-1H-pyrazol-1-yl)acetate (39)

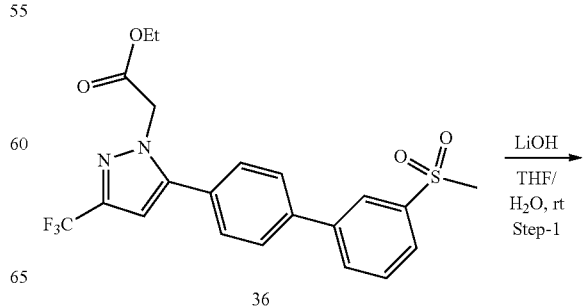

127

-continued

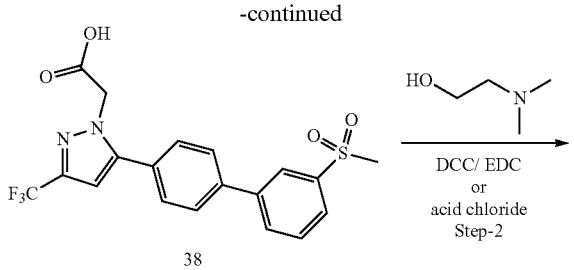

Step 1: Synthesis of 2-(5-(3'-(methylsulfonyl)-[1,1'-biphenyl]-4-yl)-3-(trifluoromethyl)-1H-pyrazol-1-yl)acetic acid) (38)

To a stirred solution of 36 (1.3 g, 2.0 mmol) in THF (10.0 mL) at room temperature, was added a solution of lithium hydroxide (103 mg, 4.0 mmol) in water (10.0 mL) and stirring continued for 2 h. On completion, the solvent was removed and the reaction mixture diluted with water (20 mL) and washed with ether (30 mL×3). The aqueous layer was acidified with 1N HCl and extracted with 10% methanol in dichloromethane (50 mL×3). Combined organic layer was washed brine, dried over sodium sulphate and concentrated. The crude product after ether and pentane washing afforded 38 (1 g, 83%). LCMS: 425.15 (M+1)$^+$; 1H NMR (DMSO-d$_6$, 400 MHz) δ 13.3 (s, 1H), 8.24 (s, 2H), 8.12 (d, 1H, J=8 Hz), 7.78 (t, 1H, J=8 Hz), 7.67 (d, 1H, J=8.4 Hz), 7.04 (s, 1H), 5.13 (s, 1H), 3.25 (s, 3H).

Step 2: Synthesis of 2-(dimethylamino)ethyl 2-(5-(3'-(methylsulfonyl)-[1,1'-biphenyl]-4-yl)-3-(trifluoromethyl)-1H-pyrazol-1-yl)acetate (39)

To a stirred solution of compound 38 (0.2 g, 0.471 mmol), 2-(dimethylamino)ethanol (0.14 mL, 1.41 mmol) and triethylamine (0.126 mL, 0.942 mmol) in DMSO (5 mL) at RT was added Pybop (0.360 g, 0.706 mmol) and the reaction mixture stirred overnight. The reaction was then diluted with water (30 mL) and extracted with ethyl acetate (50 mL×3). The combined organic layer was washed with saturated brine, dried over sodium sulphate and concentrated. The crude reaction mixture was purified by column chromatography using 3% methanol in dichloromethane to afford 39 (15 mg, 6%). LCMS: 496.25 (M+1)$^+$; $^1$H NMR (CD$_3$OD, 400 MHz) δ 8.23 (s, 1H), 8.05 (d, 1H, J=8 Hz), 8.01 (d, 1H, J=7.6 Hz), 7.88 (d, 1H, J=8.4 Hz), 7.78 (t, 3H, J=8 Hz), 7.64 (d, 2H, J=8 Hz), 6.84 (s, 1H), 5.2 (s, 2H), 4.5 (t, 2H, J=4.8 Hz), 3.49 (d, 2H, J=4.8 Hz), 3.20 (s, 3H), 2.9 (s, 6H).

128

Example 19

Synthesis of 2-(dimethylamino)ethyl 2-(4-bromo-5-(3'-(methylsulfonyl)biphenyl-4-yl)-3-(trifluoromethyl)-1H-pyrazol-1-yl)acetate (40)

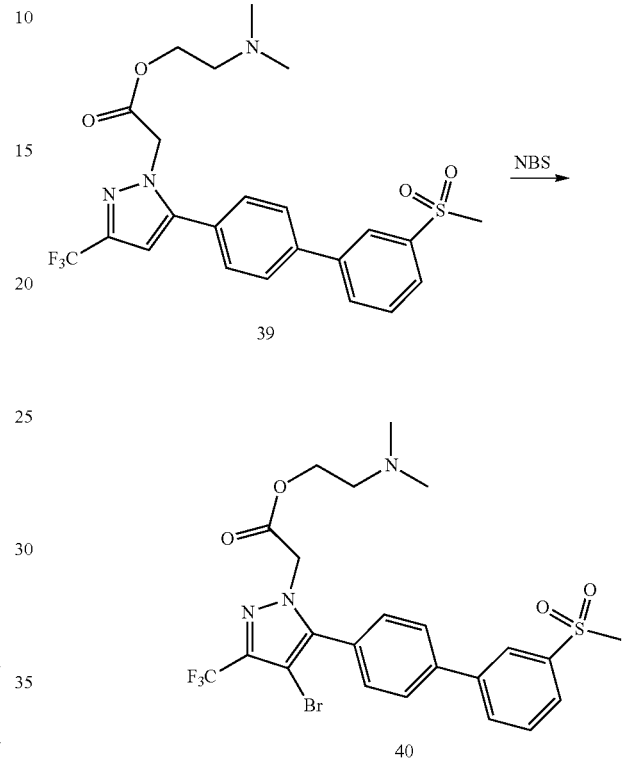

Following bromination with N-bromosuccinimide, the title compound 40 is prepared starting from 2-(dimethylamino)ethyl 2-(5-(3'-(methylsulfonyl)biphenyl-4-yl)-3-(trifluoromethyl)-1H-pyrazol-1-yl)acetate 39.

Example 20

Synthesis of methylthiomethyl 2-(5-(3'-(methylsulfonyl)biphenyl-4-yl)-3-(trifluoromethyl)-1H-pyrazol-1-yl)acetate (41)

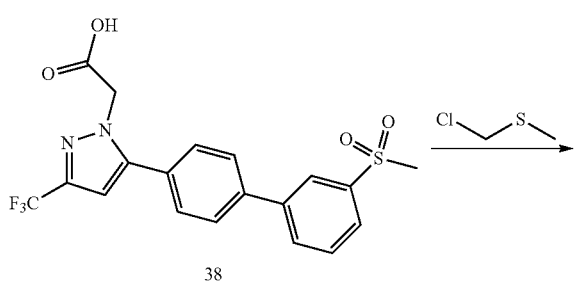

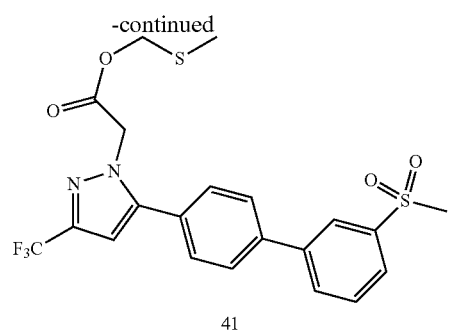

41

A mixture of compound 38 (0.2 g, 0.471 mmol), chloromethylmethylsulfane (0182 g, 1.89 mmol) and potassium carbonate (0.324 g, 2.36 mmol) in DMF (5 mL) was stirred at room temperature for 1 h, then heated to 100° C. for 10 h. On completion, the reaction mixture was diluted with water (30 mL) and extracted with ethyl acetate (50 mL×3). The combined organic layer was washed with saturated brine, dried over sodium sulphate and concentrated. The crude reaction mixture was purified by prep HPLC to afford 41 (15 mg, 7%). LCMS: 485.20 (M+1)$^+$; $^1$H NMR (DMSO-d$_6$, 400 MHz) δ 8.26 (s, 1H), 8.06 (d, 1H, J=7.2 Hz), 7.99 (d, 1H, J=8 Hz), 7.93 (d, 2H, J=8.4 Hz), 7.8-7.6 (m, 3H), 6.75 (s, 1H), 5.10-5.25 (m, 2H), 3.45-3.3 (m, 2H), 3.30 (s, 3H), 1.78 (s, 3H).

Example 21

Synthesis of methylthiomethyl 2-(4-bromo-5-(3'-(methylsulfonyl)biphenyl-4-yl)-3-(trifluoromethyl)-1H-pyrazol-1-yl)acetate (42)

Following bromination with N-bromosuccinimide, the title compound 42 is prepared starting from methylthiomethyl 2-(5-(3'-(methylsulfonyl)biphenyl-4-yl)-3-(trifluoromethyl)-1H-pyrazol-1-yl)acetate 41.

Example 22

Synthesis of 2-(5-(5-(3-(methylsulfonyl)phenyl)furan-2-yl)-3-(trifluoromethyl)-1H-pyrazol-1-yl)acetic acid (48)

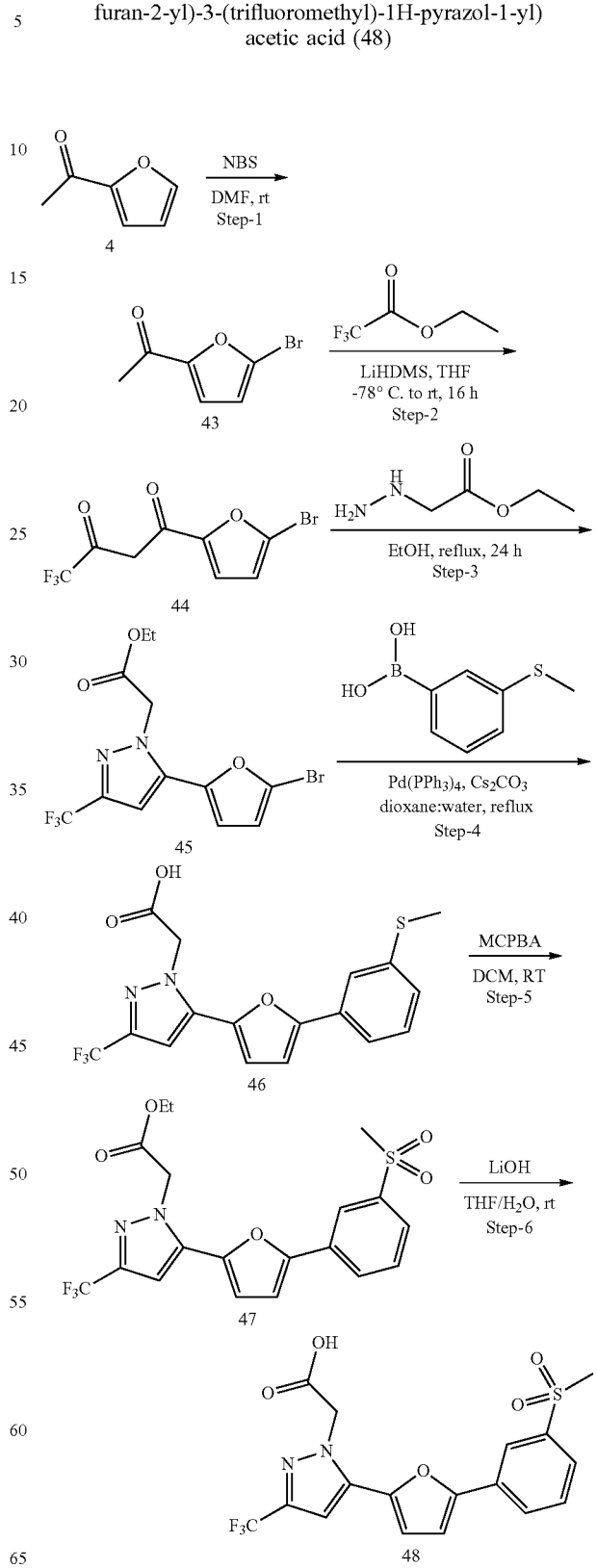

Step 1: Synthesis of 1-(5-bromofuran-2-yl)ethanone) (43)

To a stirred solution of compound 4 (5.0 g, 45.45 mmol) and DMF (50 mL), NBS (8.8 g, 50 mmol) was added portion-wise at room temperature under stirring. The reaction mixture was allowed to stir at room temperature overnight. 50% starting material remained by TLC and LCMS. Reaction mixture was poured into cold water and the compound was extracted with diethyl ether (150 mL×3). Combined organic layer was washed with brine, dried over sodium sulphate and concentrated under reduced pressure. Crude compound was purified by column chromatography using 5% ethyl acetate in n-hexane as an eluent to afford compound 43 (2.4 g, 28%) as a white solid.

Step 2: Synthesis of 1-(5-bromofuran-2-yl)-4,4,4-trifluorobutane-1,3-dione (44)

To a stirred solution of compound 43 (4.8 g, 25.4 mmol) in THF (60 mL) at −78° C., LiHMDS (38 mL, 38.1 mmol) was added dropwise and the reaction stirred −78° C. for 1 h. Ethyl 2,2,2-trifluoroacetate (4.5 g, 38.1 mmol) was then added dropwise. The reaction mixture was allowed to gradually warm to room temperature in cooling bath and stirred overnight. Solvent was removed, cold water (50 mL) was added, and the reaction mixture extracted with diethyl ether (100 mL×3). Combined organic layer was washed with brine, dried over sodium sulphate and concentrated under reduced pressure. Crude compound was washed with diethyl ether and hexane to afford compound 44 (5 g, 69%) as a white solid.

Step 3: Synthesis of ethyl 2-(5-(5-bromofuran-2-yl)-3-(trifluoromethyl)-1H-pyrazol-1-yl)acetate (45)

A mixture of compound 44 (4 g, 14.0 mmol), ethyl 2-hydrazinylacetate (2.37 g, 15.0 mmol) and methanol (60 mL) was heated for 1.5 h. The reaction mixture was cooled to 0° C. and solvent was removed under reduced pressure. Water (100 mL) was added and the reaction mixture extracted with ethyl acetate (50 mL×3). Combined organic layer was washed with brine, dried over sodium sulphate and concentrated under reduced pressure. The crude compound was purified by column chromatography using 10% ethyl acetate in n-hexane as an eluent to afford the separated isomer 45 (1.2 g, 24%).

Step 4: Synthesis of ethyl 2-(5-(5-(3-(methylthio)phenyl)furan-2-yl)-3-(trifluoromethyl)-1H-pyrazol-1-yl)acetate (46)

A mixture of compound 45 (1.25 g, 3.42 mmol) and (3-(methylthio)phenyl)boronic acid (1.15 g, 6.84 mmol) in DMF (50 mL) was degassed with argon for 30 min. To the mixture tetrakis(triphenylphosphine)palladium(0) (390 mg, 0.34 mmol) was added, degassed for 30 min followed by sodium carbonate (0.91 g, 8.56 mmol). The reaction was again degassed with argon for 30 min and heated to 90° C. for 3 h. After completion of reaction, solvent was removed under reduced pressure and the reaction mixture diluted with water (30 mL). The mixture was extracted with ethyl acetate (50 mL×3) and combined organic layer was washed with saturated brine (50 mL×2), dried over sodium sulphate and concentrated under reduced pressure. Crude compound was purified by column chromatography using 5% ethyl acetate in n-hexane as an eluent to afford compound 46 (1 g, 71%).

Step 5: Synthesis of ethyl 2-(5-(5-(3-(methylsulfonyl)phenyl)furan-2-yl)-3-(trifluoromethyl)-1H-pyrazol-1-yl)acetate (47)

To a solution of compound 46 (1 g, 2.44 mmol) in DCM (150 mL), was added mCPBA (1.26 g, 7.31 mmol) at room temperature. The reaction mixture was stirred at room temperature for 90 min. The reaction mixture was diluted with DCM (100 mL) and washed with water (50 mL×3). The combined organic layer was washed with saturated brine, dried over sodium sulphate and concentrated under reduced pressure. The crude reaction mixture was purified by column chromatography using 40% ethyl acetate and n-hexane as a eluent, to afford 47 (0.5 g, 46%). LCMS: 443.20 (M+1)$^+$; $^1$H NMR (CDCl$_3$, 400 MHz) δ 8.19 (s, 1H), 7.92-7.87 (m, 2H), 7.65-7.62 (t, J=7.8 Hz, 1H), 6.92-9.91 (d, J=3.2 Hz, 1H), 6.85 (s, 1H), 6.77-6.76 (d, J=3.6 Hz, 1H), 5.28 (s, 2H), 4.27-4.22 (q, J=7.06 Hz, 2H), 3.13 (s, 3H), 1.21-1.18 (t, J=7 Hz, 3H).

Step 6: Synthesis of 2-(5-(5-(3-(methylsulfonyl)phenyl)furan-2-yl)-3-(trifluoromethyl)-1H-pyrazol-1-yl)acetic acid (48)

To a stirred solution of compound 47 (0.5 g, 1.13 mmol) in THF (5.0 mL) was added lithium hydroxide (41 mg, 1.69 mmol) in water (5.0 mL) and the mixture was stirred at room temperature for 2 h. On completion, the solvent was removed under reduced pressure and the reaction mixture diluted with water (20 mL) and extracted with diethylether (30 mL×3). The aqueous layer was acidified with 1N HCl (pH=3) and extracted with 10% methanol in dichloromethane (50 mL×3). Combined organic layer was washed with brine, dried over sodium sulphate and concentrated under reduced pressure. The crude product after ether and pentane washing afforded 48 (0.4 g, 86%). LCMS: 415.10 (M+1)$^+$; $^1$H NMR (DMSO-d$_6$, 400 MHz) δ 13.50 (br, 1H), 8.28 (s, 1H), 8.13-8.11 (d, J=8 Hz, 1H), 7.89-7.87 (d, J=8 Hz, 1H), 7.76-7.72 (t, J=8 Hz, 1H), 7.41-7.40 (d, J=3.6 Hz, 1H), 7.34 (s, 1H), 7.19-7.18 (d, J=3.6 Hz, 1H), 5.43 (s, 2H), 3.30 (s, 3H).

Example 23

Synthesis of ethyl 2-(5-(5-(3-(methylsulfonyl)phenyl)thiophen-2-yl)-3-(trifluoromethyl)-1H-pyrazol-1-yl)acetate (49)

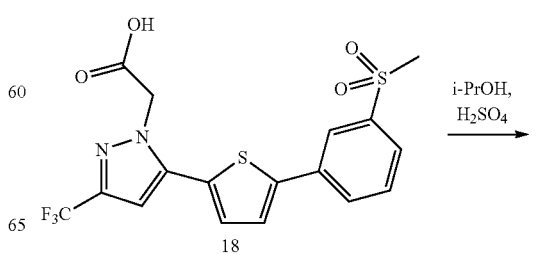

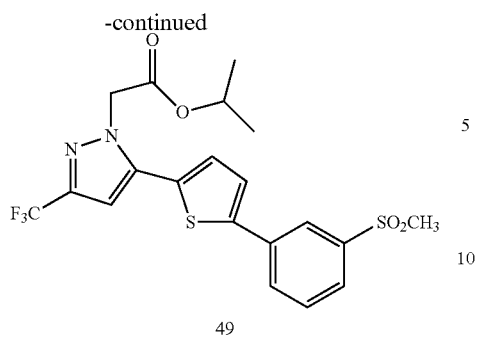

49

To a solution of 18 (1 eq) in i-PrOH (50 mL) was added 5 drops of conc. $H_2SO_4$ and the reaction heated to 90° C. for 16 h: Crude TLC and LCMS showed formation of desired ester purified by column chromatography to afford 100 mg of 49. LCMS: 473.6 (M+1)+.

Example 24

Synthesis of ethyl 2-(5-(5-(4-(hydroxymethyl)-3-(methylsulfonyl)phenyl)thiophen-2-yl)-3-(trifluoromethyl)-1H-pyrazol-1-yl)acetate (50)

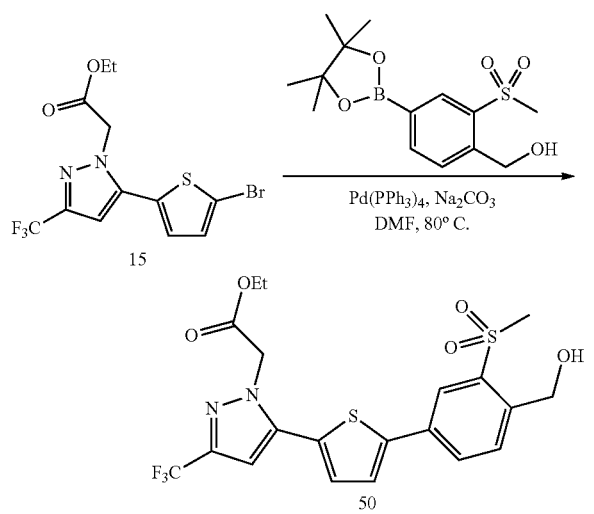

Suzuki coupling of 15 (300 mg) with 2 eq of the boronate, 0.1 eq tetrakis(triphenylphosphine)palladium(0), and 2.5 eq $Na_2CO_3$ in 20 mL DMF at 80° C. for 2 h afforded after column purification, 160 mg of compound 50. LCMS: 489.10 (M+1)+.

Example 25

Synthesis of ethyl 2-(5-(4'-(hydroxymethyl)-3'-(methylsulfonyl)biphenyl-4-yl)-3-(trifluoromethyl)-1H-pyrazol-1-yl)acetate (51)

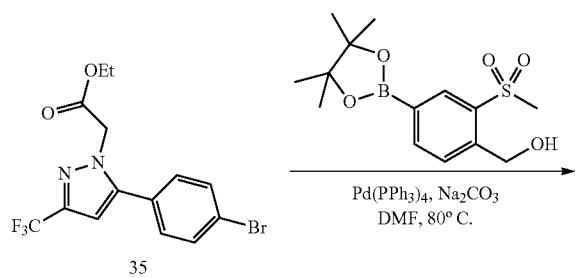

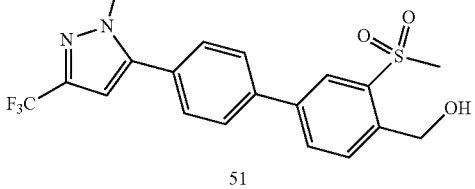

51

Suzuki coupling of 35 (300 mg) with 2 eq of the boronate, 0.1 eq tetrakis(triphenylphosphine)palladium(0), and 2.5 eq $Na_2CO_3$ in 20 mL DMF at 80° C. for 2 h afforded after column purification, 100 mg of compound 51. LCMS: 483.20 (M+1)+.

Example 26

Synthesis of chloromethyl 2-(5-(5-(3-(methylsulfonyl)phenyl)thiophen-2-yl)-3-(trifluoromethyl)-1H-pyrazol-1-yl)acetate (52)

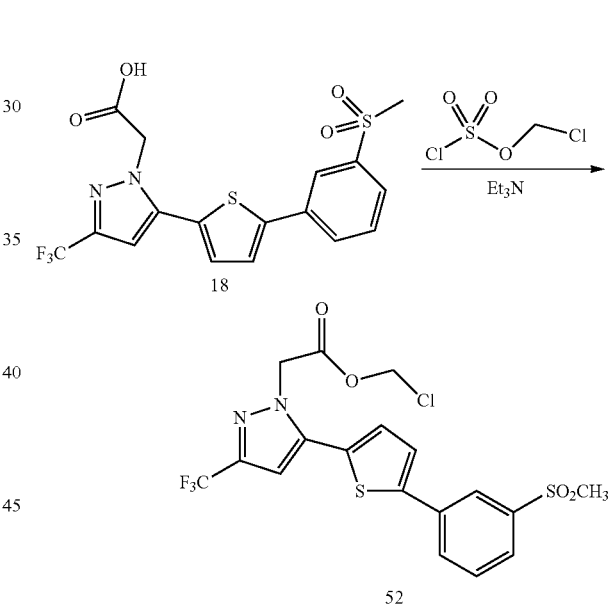

Esterification of the carboxylic acid 18 with chloromethylsulfuryl chloride as shown above afforded the chloromethyl ester 52. LCMS: 479.2 (M+1)+.

Example 27

RNA Extraction

Add QIAzol® Lysis Reagent (QIAGEN Cat Number 79306) to the cells. Scrape the cells and place into a Falcon Polypropylene tube. Let stand at room temperature for 5 minutes. Add 1 ml of cells to microfuge tubes. Add 200 µl of chloroform, vortex, let stand for 5 minutes. Centrifuge at 4° C. for 15 minutes at 14,000 RPM. Add an equal volume of 70% ETOH (diluted with DEPC water). Add 600 µl to the RNeasy@column from the RNeasy® Mini Kit (QIAGEN Cat. Number 74106) centrifuge at 14,000 RPM at room temperature for 1 minute, discard flow-through. Add remainder of sample to the column, centrifuge, discard flow-through. Add 350 µl of RW1 buffer from the RNeasy® Mini Kit to the column, centrifuge at room temperature for 1 minute, discard flow-through. DNase column with RNase-Free DNase Set (QIAGEN cat. Number 79254) by making DNase I stock solution, add 550 µl of water to the DNase, add 10 µl of DNase to 70 µl of BufferRDD for each sample, mix, add 80 µl to the column, let stand for 15 minutes. Add 350 µl of RW1 buffer to column, centrifuge for 1 minute, discard flow-through. Add 500 µl RPE buffer to column, centrifuge for 1 minute, discard flow-through. Add 500 µl RPE buffer to column, centrifuge for 1 minute, discard flow-through. Put column into a clean 2.0 ml microfuge tube, centrifuge for 2 minutes. Put column into a microfuge tube, add 50 µl of water, allow column to stand for 2 minutes, centrifuge for 1 minute.

Quantitative PCR

TaqMan technology is used for quantitative PCR for the evaluation of MMP, TNFα, TIMP, IL-8, ASAH1, SPTLC1, SMPD1, LASS2, TXNRD1, GPX3, GSR, CAT, ApoE, ABCA1, ABCA2, ABCA12, ABCA13, ABCG1, decorin, and LXRα/β gene expression in keratinocytes and fibroblasts.

Conditions for use of TaqMan Reverse Transcriptase Reagents (Applied Biosystems Cat. Number N808-0234): 10×RT buffer: 10 µl, MgCl$_2$ solution: 22 µl, DNTP mix: 20 µl, Random Hexamers: 5 µl, Multi Scribe RT: 2.5 µl, RNase Inhibitor: 2.5 µl, 2 µg RNA. Thermocycler: 25° C.—10 minutes, 48° C.—30 minutes, 95° C.—5 minutes.

Setup TaqMan with QuantiTect Multiplex PCR Kit (QIAGEN cat. Number 204543): 2× master mix: 25 µl; Single Tube Assay: 2.5 µl; Applied Biosystems Primers Probe set (part number 4308329)-18S forward primer: 0.25 µl, 18S reverse primer: 0.25 µl, 18S probe: 0.25 µl; water to 50 µl; 5 µl cDNA. Thermocycler: 50° C.—2 minutes, 95° C.—10 minutes, 95° C.—15 seconds, 60° C.—1 minute.

Example 28

Induction of Expression of LXR Receptors

Clonetics® Normal Human Epidermal Keratinocytes (NHEKs) are obtained from Cambrex Bio Science, Inc. The proliferating T-25 (C2503TA25) pooled, neonatal keratinocytes are expanded in Clonetics® KGM-2 serum-free medium (CC-3107) and subcultured as needed using the recommended Clonetics® ReagentPack™ (CC-5034). Due to a light-sensitive component in the medium, all manipulations are done in low light.

For experiments, 1.6 million NHEK cells are plated in growth medium on 100 mm dishes and allowed to grow to 75% confluence. On the day of treatment, the dishes are rinsed once with KGM-2 minus hydrocortisone; then, vehicle (0.1% DMSO) or 1 µM or an LXR agonist described herein, is added for 6 h in hydrocortisone-deficient KGM-2. After 6 h, the treatment medium is temporarily removed, the dishes washed with Dulbecco's Phosphate Buffered Saline, and then half of the treatments are exposed to 8 J/m$^2$ ultraviolet light using a Stratagene UV Stratalinker® 2400. Treatments are replaced and 18 h later the samples are harvested for RNA processing using TRIzol®D Reagent (Invitrogen).

RNA is extracted as described above. UV irradiation of NHEKs slightly reduced the expression of LXRα. Treatment of keratinocytes with the LXR modulator (1 µM) induces the expression of LXRα in both UV-unexposed and UV-exposed keratinocytes. UV treatment of NHEKs down-regulates LXRβ expression, and this UV-mediated inhibition of LXRβ expression is reversed by treatment with the LXR modulator. Therefore, induction of expression of both LXR receptors in UV-exposed keratinocytes by an LXR modulator indicates efficacy of the LXT modulator. Further, LXR modulators may help the UV-exposed keratinocytes/skin to be more responsive to its effects.

Gal4 LXRβ Cotransfection Assay

For transient transfection of HEK 293 cells, 6×10$^3$ cells were plated into 96-well dishes. Each well was transfected with 25 ng 5×UAS-luciferase reporter (pG5luc) and 25 ng of pM human LXRβ (AA 153-461) LBD plasmid using Fugene 6 reagent (Roche; Indianapolis, Ind.). The chimeric protein was assessed for the ability to transactivate a Gal4-responsive luciferase reporter plasmid in a concentration-responsive manner to compounds (0.01-10 µM). Luciferase activity at each dose concentration was measured in triplicate using standard substrate reagents (BD Biosciences; San Diego, Calif.). Data are expressed as relative light units and are shown below in Table 1.

TABLE 1

EC$_{50}$ values for LXR modulators in LXRβ Gal fusion assay.

| Compound | LXRβ Gal (EC$_{50}$) µM |
|---|---|
| 9 | B |
| 10 | C |
| 11 | A |
| 12 | C |
| 16 | A |
| 18 | C |
| 36 | A |
| 38 | C |
| 41 | B |
| 49 | A |
| 50 | A |
| 51 | A |
| 52 | A |

A, EC$_{50}$ <1 µM; B, EC$_{50}$ = 1-10 µM; C, EC$_{50}$ >10 µM

Example 29

ABCG1 Expression

NHEKs (Cambrex/Lanza, Walkersville, Md.) were cultured as per vendor's recommendations. In general, cells were trypsinized and seeded on day 0, and treated with Compounds (1 µM) on day 1. The cells were harvested on day 2 with lysis buffer (AppliedBiosystems/Ambion, Foster City, Calif.) directly added to the cultured cells after a PBS wash. NHEKs were either used for RNA purification using Qiagen RNeasy RNA purification column (Qiagen, Hilden, Germany) as pervendor's protocol or directly processed to cDNA using "Cell-to-cDNA" lysis buffer (Ambion, Foster City, Calif.). RNA was isolated and ABCG1 gene expression analyzed by real-time PCR is shown in FIG. 1 for three compounds of Formula I-VI:

Compound A, Compound B, and Compound C. As shown in FIG. 1, Compound A, Compound B, and Compound C induce ABCG1 in human keratinocytes.

Example 30

TNFalpha Expression

NHEKs are treated and RNA extracted as described in Example 27. UV exposure of keratinocytes causes induction of TNFα expression. A reduced expression of UV-induced TNFα expression in the presence of an LXR agonist described herein indicates less activation of dermal fibroblasts, and less production of metalloproteases that degrade the dermal matrix.

Example 31

MMP3 Expression

NHEKs are treated and RNA extracted as described in Example 27. UV exposure of keratinocytes causes induction of MMP3 expression. A reduced expression of UV-induced MMP-3 expression in the presence of an LXR agonist described herein indicates reduced degradation of the dermal matrix.

Example 32

TIMP1 Expression

NHEKs are treated and RNA extracted as described in Example 27. UV exposure of keratinocytes causes reduction of the basal level of expression of TIMP1 expression. A reduced expression of UV-induced TIMP1 expression in the presence of an LXR agonist described herein is expected to neutralize the metalloprotease activities, resulting in the protection of dermal matrix from the action of MMPs.

Example 33

IL-8 Expression

NHEKs are treated and RNA extracted as described in Example 27. UV exposure of keratinocytes causes induction of IL-8 expression. Because IL-8 is a chemotactic molecule, a reduced expression of UV-induced IL-8 expression in the presence an LXR agonist described herein is expected to result in less recruitment of activated neutrophils into the dermis. Active neutrophils are also a source of MMPs and elastase that degrade the dermal matrix in photo aging.

Example 34

Synthesis of Lipids

Photoaged or photodamaged skin shows defective epidermal barrier function. ABCA12 is a lipid transporter that is essential for the maintenance and development of the epidermal barrier function of the skin. Therefore, LXR ligands may induce the synthesis of lipids and their loading into epidermal lamellar bodies by inducing the expression of lipid binding proteins and ABC transporter family members required for cholesterol and lipid efflux These gene regulations also indicate that the LXR ligands may exhibit potent anti-xerosis therapeutic effect, thus alleviating one of the major symptoms of aged skin that leads to deterioration of epidermal barrier function and responsible for initiating other serious cutaneous conditions.

NHEK cells are treated and RNA extracted as described in Example 27. UV exposure of keratinocytes causes downregulation of ABCA12 expression in UV-exposed keratinocytes. A reversal of the expression of UV-induced ABCA12 expression by treatment an LXR agonist described herein is expected to result in normalization of epidermal barrier function in the photoaged skin. Improved epidermal barrier function is expected to reduce skin dryness, a hallmark of photodamaged/photoaged skin. Improved epidermal barrier function is expected to reduce skin dryness, a hallmark of photodamaged/photoaged skin.

Example 35

Collagen

Photoaged and chronologically aged skin shows decreased levels of collagen. Collagen is a component of the extracellular matrix that is required for imparting rigidity to cellular as well as dermal matrix structures. Collagen molecules are arranged in the form of collagen fibrils that is required for the normal architecture of the skin. This fibrillar architecture of the collagen is degraded in aged/wrinkled skin. Therefore, restoration of the collagen fibrillar structure is also expected to result in therapeutic improvement of the photodamaged/photoaged skin.

Decorin is an extracellular matrix component that associates with collagen I. Further, decorin-collagen interaction is required for collagen fibril formation. In other words, decorin is a critical regulator of collagen 1 fibrillar-genesis. Therefore, increased decorin expression in UV-exposed photodamaged skin is expected to induce the generation of collagen fibrils, a process that may improve skin laxity and wrinkles.

NHEK cells are treated and RNA extracted as described in Example 27. UV exposure of NHEKs causes inhibition of decorin expression. A reversal of the UVB-mediated inhibition of decorin expression by treatment with an LXR agonist described herein is expected to result in normalized decorin expression in UV-exposed keratinocytes. The induction of decorin expression is expected to result in increased extracellular matrix formation.

Example 36

MMP1 Expression

The BJ cell line (ATCC #CRL-2522) is obtained from ATCC. It is a normal human fibroblast cell line originally derived from foreskin, demonstrating extended lifespan in culture of 80-90 population doublings. The cells are maintained in Eagle's Minimal Essential medium with Earle's BSS (EMEM) supplemented with penicillin-streptomycin, 1.0 mM sodium pyruvate, 0.1 mM non-essential amino acids, 2 mM GlutaMAX-1™ and 10% HyClone fetal bovine serum (FBS). With the exception of serum, all reagents are obtained from Invitrogen. The cells are subcultured with 0.05% trypsin-EDTA twice a week and maintained in a humidified incubator at 37° C. and 5% $CO_2$.

For experiments, 5 million BJ cells are plated in 150 mm dishes in growth medium. The following day, the phenol red-containing growth medium is removed and plates are rinsed once with phenol red-free EMEM without serum. Experimental medium is phenol red-free EMEM supplemented as above with the addition of 5% Lipoprotein Deficient Serum (Sigma S-5394) instead of HyClone FBS. DMSO vehicle (0.1%) or 1 µM or an LXR agonist described herein is added to the dishes for 6 h; at which time 5 ng/ml rhTNFα (R&D 210-TA) is added to half of the treatments. Samples are harvested with TRIzol® 18 h later and processed.

RNA is extracted as described above. TNFα treatment of BJ human fibroblasts causes induction of MMP1 expression. Inhibition of TNFα-induced MMP1 expression upon treatment of human fibroblasts with an LXR agonist described herein is expected to result in reduced degradation of the dermal matrix because MMP1 is the major destroyer of the dermal matrix collagen.

Example 37

MMP3 Expression

BJ cells are treated and RNA extracted as described in Example 27. TNFα treatment of BJ human fibroblasts causes induction of MMP3 expression. Inhibition of TNFα-induced MMP-3 expression upon treatment of human fibroblasts with an LXR agonist described herein is expected to result in reduced degradation of the dermal matrix.

Example 38

TIMP1 Expression

BJ cells are treated and RNA extracted as described in Example 27. TNFα exposure of human BJ fibroblasts does not cause reduction of the basal level expression of TIMP1 expression. An LXR agonist described herein which induces TIMP1 expression in both TNFα-unexposed as well as TNFα-exposed fibroblasts is expected to neutralize the metalloprotease activities, resulting in the protection of dermal matrix from the action of MMPs.

Example 39

Ceramide and Lipid Second Messenger Sphingolipids Biosynthetic Pathway

NHEK cells are treated and RNA is extracted as described in Example 27. Ceramide is one of the major lipids in differentiated keratinocytes and it plays a pivotal role in skin barrier function. A comparison of chronologically aged and young skin revealed a decrease in ceramide content with age. The decline in ceramide content may result from reduced keratinocyte differentiation as well as because of reduced ceramide synthase and sphingomyelin (SM) phosphodiesterase activities in chronological aging. Serine palmitoyltransferase (SPTLC1) catalyzes the formation of sphinganine from serine and palmitoyl-CoA. Ceramide synthase (LASS2) converts sphinganine into ceramide. SM phosphodiesterase (SMPD) also produces ceramide from SM, and acid ceramidase (ASAH1) produces lipid second messenger sphingosine from ceramide.

An induction of the expression of enzymes involved in ceramide and lipid second messenger sphingolipids biosynthetic pathway by an LXR agonist described herein is indicative of therapeutic efficacy. Since ceramides and other sphingolipids are involved in keratinocyte proliferation, differentiation and desquamation, an increase in the expression of enzymes involved in the synthesis of sphingolipids may help in these processes and alleviate the epidermal problems (dry skin, decreased keratinocyte proliferation and differentiation, fine scales) that stem from decreased sphingolipid production.

Example 40

Antioxidant Activities in Keratinocytes

NHEK cells are treated and RNA extracted as described in Example 27. UV-mediated cumulative oxidative damage in both epidermis and dermis due to accumulation of free radicals throughout life in all likelihood also promotes cellular aging. Free radicals or reactive oxygen species cause damage to lipids, protein and DNA, and cause cells to enter a senescent-like stage. There are many reports describing the reduction of antioxidant enzymes in skin with age, including superoxide dismutase, catalase and glutathione peroxidase.

An induction of the expression of enzymes involved in the expression of enzymes involved in antioxidant activities in keratinocytes, e.g., expression of anti-oxidant enzymes, glutathione peroxidase (GPX3), thioredoxin reductase, glutathione reductase and catalase, by an LXR agonist described herein is indicative of therapeutic efficacy. LXR modulators increase the free-radical fighting defense system of the body, which may reduce the insult of hydrogen peroxide and free-radicals on skin cell proteins, lipids and DNA.

Example 41

Allergic Contact Dermatitis of the Mouse Ear

Figure 2:
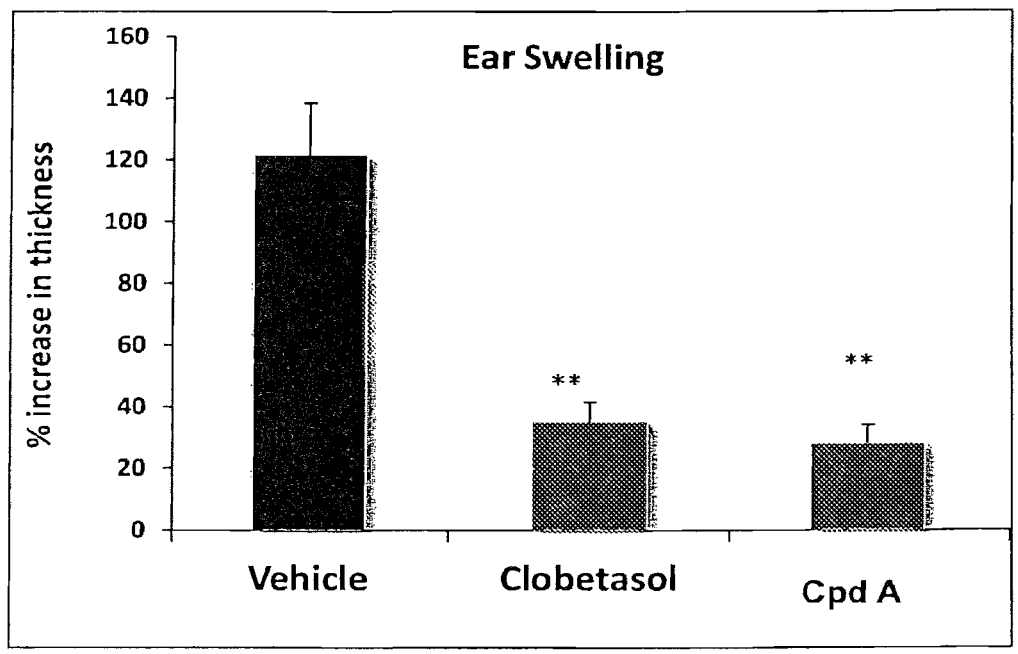
FIG. 2 shows ear swelling and ear weight for Compound A compared to Clobetasol (corticosteroid used to treat various skin disorders) as outlined in Example 41.
Figure 2:
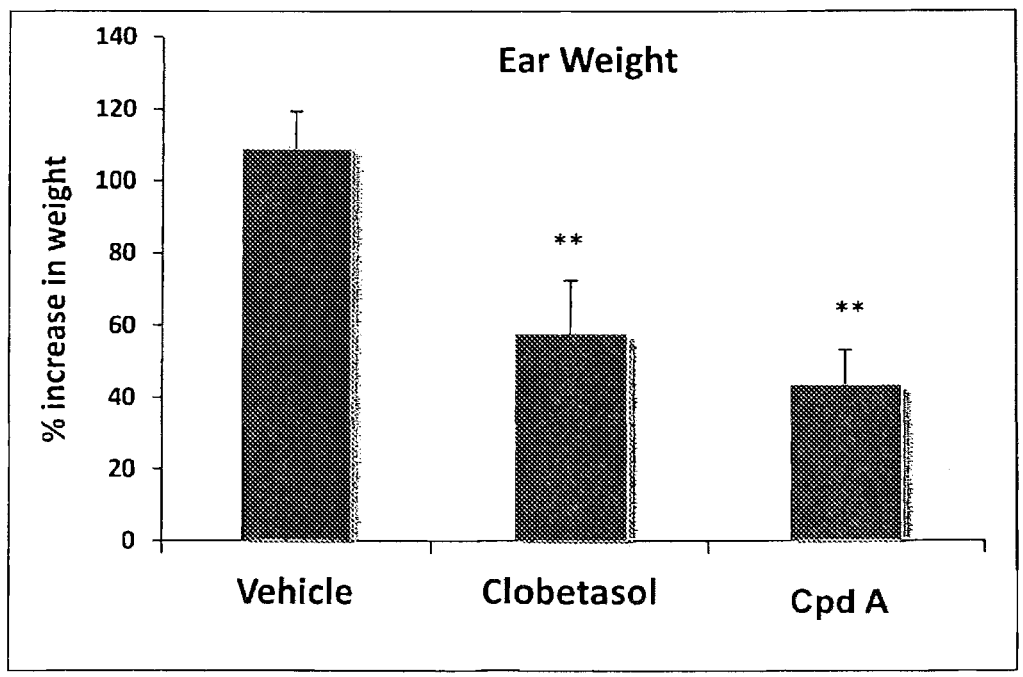

The mouse contact dermatitis model (ear edema model) has been previously used for the characterization of topical application of LXR activators for their effect on skin inflammation (Fowler et al. J Invest Dermatol 120:246 (2003)). Phorbol 12-myristate-13-acetate (PMA) was applied topically to both the inner and outer surface (10 µL each surface, 20 µL total) of the left ears to induce irritant contact dermatitis. Acetone alone (vehicle) was applied to the right ears. 30 min prior and 15 min after PMA application, 20 µL of test compounds, was applied to both surfaces of left ear (40 µL total). Identical treatments were performed with 20 µL of the positive control, 0.05% clobetasol, while the vehicle group received acetone application alone. After 6 h, blood samples (approximately 60 µL) were collected from retro-orbital plexus of 5 mice (from each group) at 6 h time point, into labeled micro-tubes, containing $K_2EDTA$ solution as an anticoagulant. Plasma was immediately harvested by centrifugation at 4000 rpm for 10 min at 4±2° C. and stored below −70° C. until bioanalysis. The inflammatory insult induced by PMA was assessed as the percentage increase in ear thickness and/or ear weight in the treated left ear versus the vehicle-treated right ear. Ear thickness was measured with a digital caliper followed by whole ear weight to ascertain changes in ear weights. The extent of inflammation was quantitated according to the following equation: ear swelling (%)=100×(a−b)/b, where a is the thickness/weight of the left (treated) ear and b is the thickness/weight of the right (untreated control) ear. After obtaining the samples for assessment of ear thickness/weight, biopsies were obtained from adjacent sites for routine histopathology fixation in 4% freshly prepared paraformaldehyde in phosphate-buffered saline. Ear swelling and ear weight for Compound A compared to Clobetasol (corticosteroid used to treat various skin disorders) is shown in FIG. 2. Compound A reduces ear swelling and weight in the mouse contact dermatitis model.

Example 42

Phase II Clinical Trial of the Safety and Efficacy of Compounds of Formula (I), (II), (III), (IV), (V), or (VI) in Patients with Mild to Moderate Chronic Plaque Psoriasis The purpose of this phase II trial is to investigate the safety and efficacy of a topical administration of a compound of Formula (I), (II), (III), (IV), (V), or (VI) in patients with mild to moderate chronic plaque psoriasis.

Patients:

Eligible subjects will be men and women 18 years of age and older.

Criteria:

Inclusion Criteria:

Mild to moderate chronic plaque psoriasis (psoriasis vulgaris), with the duration of at least 6 months;

A target plaque of at least 9 sq. cm.

Exclusion Criteria:

Demonstrates "rebound" or "flare" of chronic plaque psoriasis;

Non plaque form of psoriasis;

Currently have or history of psoriatic arthritis;

Current drug induced psoriasis;

Currently on systemic therapy or was on systemic therapy for psoriasis within the previous 6 months;

Currently on phototherapy for psoriasis or was on phototherapy within the previous 3 months.

Study Design:

Allocation: Randomized

Endpoint Classification: Safety/Efficacy Study

Intervention Model: Parallel Assignment

Masking: Double Blind (Subject, Investigator)

Primary Purpose: Treatment

Primary Outcome Measures:

Percent change from baseline at Week 4 in Target Plaque Severity Score (TPSS)

Secondary Outcome Measures:

Proportion of subjects with Treatment Area Overall Severity of Psoriasis response of "clear" (0) or "almost clear" (1) at Weeks 1, 2, 3 and 4;

Proportion of subjects with a difference from baseline of >=2 steps in Treatment Area Overall Severity of Psoriasis score at Weeks 1, 2, 3 and 4

Percent change from baseline at Weeks 1, 2, 3 and 4 in Target Plaque Area

Change from baseline at Weeks 1, 2, 3 and 4 in TPSS subscores for Erythema, Induration and Scaling Percent change from Baseline in TPSS at Weeks 1, 2 and 3

Actual and change from baseline on the treatment area Itch Severity Item (ISI) at Weeks 1, 2, 3 and 4

Proportion of subjects in each Patient Satisfaction with Study Medication (PSSM) response category at Week 4

Incidence, nature and severity of observed and reported administration site adverse events over 4 weeks of treatment Incidence and severity of burning/stinging of psoriatic or perilesional skin in the treatment area over 4 weeks of treatment Incidence and severity of reactions of perilesional skin in the treatment area as measured by Draize scoring over 4 weeks of treatment Incidence and severity of adverse events over 4 weeks of treatment Incidence of clinical laboratory abnormalities and change from baseline in clinical laboratory values over 4 weeks of treatment Incidence of clinically significant changes in physical examination from baseline over 4 weeks of treatment Incidence of vital sign (blood pressure and heart rate) abnormalities and change from baseline in vital sign measures over 4 weeks of treatment Incidence of electrocardiogram (ECG) abnormalities and change from baseline in ECG measures over 4 weeks of treatment Plasma CP-690,550 concentrations, from blood sampling at Week 4 (Day 29)

| Arms | Assigned Interventions |
|---|---|
| Treatment Group A: Experimental Intervention: Drug: Compound of Formula I, II, III, IV, V, or VI Ointment 1 | Drug: Compound of Formula I, II, III, IV, V, or VI Ointment 1 Ointment 1 twice daily for 4 weeks |
| Treatment Group B: Placebo Comparator Intervention: Drug: Vehicle 1 | Drug: Vehicle 1 Vehicle 1 twice daily for 4 weeks |
| Treatment Group C: Experimental Intervention: Drug: Compound of Formula I, II, III, IV, V, or VI Ointment 2 | Drug: Compound of Formula I, II, III, IV, V, or VI Ointment 2 2% CP-690, 550 Ointment 2 twice daily for 4 weeks |
| Treatment Group D: Placebo Comparator Intervention: Drug: Vehicle 2 | Drug: Vehicle 2 Vehicle 2 twice daily for 4 weeks |

The examples and embodiments described herein are for illustrative purposes only and in some embodiments, various modifications or changes are to be included within the purview of disclosure and scope of the appended claims.

What is claimed is:

1. A compound of Formula (D):

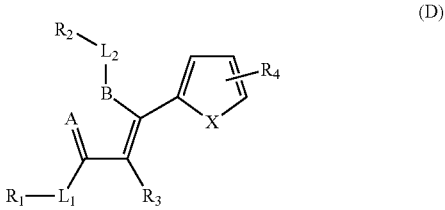

wherein:

X is —N($R_{12}$)— or —O—;

A and B are each nitrogen, wherein A and B are bonded together to form a five-membered heteroaryl ring;

$L_1$ is a bond, $C_1$-$C_6$alkyl, or $C_1$-$C_6$heteroalkyl;

$L_2$ is $C_1$-$C_6$alkyl or $C_1$-$C_6$heteroalkyl;

$R_1$ is hydrogen, halogen, —$CF_3$, —$OR_8$, —$N(R_8)_2$, —C(=O)$R_8$, —C(=O)O$R_8$, —C(=O)N($R_8)_2$, —C(=N—OH)$R_8$, —C(=S)N($R_8)_2$, —C(=$CH_2$)$CH_3$, or —C(=O)O$CH_2SCH_3$;

$R_2$ is —C(=O)O$R_9$, —C(=O)N($R_9)_2$, —$NR_{10}$C(=O)$R_9$, —C(=N—OH)$R_9$, —C(=S)N($R_9)_2$, or —C(=O)O$CH_2SCH_3$;

$R_3$ is hydrogen, halogen, $C_1$-$C_6$alkyl, or $C_1$-$C_6$haloalkyl;

$R_4$ is aryl or heteroaryl; wherein aryl or heteroaryl is substituted with at least one $R_{11}$;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

$R_{11}$ is independently halogen, nitro, —$OR_{10}$, —N($R_{10})_2$, —CN, —C(=O)$R_{10}$, —C(=O)O$R_{10}$, —C(=O)N($R_{10})_2$, —$NR_{10}$C(=O)$R_{10}$, $NR_{10}SO_2R_{10}$, —SO$R_{10}$, —$SO_2R_{10}$, —$SO_2N(R_{10})_2$, —C(=O)O$CH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

R$_{12}$ is hydrogen or C$_1$-C$_6$alkyl;

or a pharmaceutically acceptable salt or a pharmaceutically acceptable solvate thereof.

2. The compound of claim 1, or a pharmaceutically acceptable or a pharmaceutically acceptable solvate thereof, wherein X is —N(R$_{12}$)—.

3. The compound of claim 1, or a pharmaceutically acceptable or a pharmaceutically acceptable solvate thereof, wherein R$_1$ is —CF$_3$.

4. The compound of claim 1, or a pharmaceutically acceptable or a pharmaceutically acceptable solvate thereof, wherein R$_2$ is —C(═O)OR$_9$.

5. The compound of claim 1, or a pharmaceutically acceptable or a pharmaceutically acceptable solvate thereof, wherein L$_1$ is a bond and L$_2$ is C$_1$-C$_6$alkyl.

6. The compound of claim 1, or a pharmaceutically acceptable or a pharmaceutically acceptable solvate thereof, wherein R$_4$ is phenyl substituted with one R$_{11}$.

7. The compound of claim 1, or a pharmaceutically acceptable or a pharmaceutically acceptable solvate thereof, wherein R$_4$ is phenyl substituted with two R$_{11}$.

8. The compound of claim 1, or a pharmaceutically acceptable or a pharmaceutically acceptable solvate thereof, wherein R$_{11}$ is —SO$_2$R$_{10}$.

9. The compound of claim 1, or a pharmaceutically acceptable or a pharmaceutically acceptable solvate thereof, wherein R$_{11}$ is —SO$_2$N(R$_{10}$)$_2$.

10. The compound of claim 1, or a pharmaceutically acceptable or a pharmaceutically acceptable solvate thereof, wherein X is —N(R$_{12}$)—, L$_1$ is a bond, R$_1$ is —CF$_3$, L$_2$ is C$_1$-C$_6$alkyl, R$_2$ is C(═O)OR$_9$, R$_9$ is C$_1$-C$_6$alkyl, R$_4$ is phenyl substituted with one R$_{11}$, R$_{11}$ is —SO$_2$R$_{10}$, and R$_{10}$ is C$_1$-C$_6$alkyl.

11. The compound of claim 1, or a pharmaceutically acceptable or a pharmaceutically acceptable solvate thereof, wherein X is —N(R$_{12}$)—, L$_1$ is a bond, R$_1$ is —CF$_3$, L$_2$ is C$_1$-C$_6$alkyl, R$_2$ is C(═O)OR$_9$, R$_9$ is C$_1$-C$_6$heteroalkyl, R$_4$ is phenyl substituted with one R$_{11}$, R$_{11}$ is —SO$_2$R$_{10}$, and R$_{10}$ is C$_1$-C$_6$alkyl.

12. The compound of claim 1, or a pharmaceutically acceptable or a pharmaceutically acceptable solvate thereof, wherein R$_3$ is hydrogen or halogen.

13. The compound of claim 1, or a pharmaceutically acceptable or a pharmaceutically acceptable solvate thereof, wherein X is —O—.

14. The compound of claim 1, or a pharmaceutically acceptable or a pharmaceutically acceptable solvate thereof, wherein R$_1$ is —CF$_3$.

15. The compound of claim 1, or a pharmaceutically acceptable or a pharmaceutically acceptable solvate thereof, wherein R$_2$ is —C(═O)OR$_9$.

16. The compound of claim 1, or a pharmaceutically acceptable or a pharmaceutically acceptable solvate thereof, wherein L$_1$ is a bond and L$_2$ is C$_1$-C$_6$alkyl.

17. The compound of claim 1, or a pharmaceutically acceptable or a pharmaceutically acceptable solvate thereof, wherein R$_4$ is phenyl substituted with one R$_{11}$.

18. The compound of claim 1, or a pharmaceutically acceptable or a pharmaceutically acceptable solvate thereof, wherein R$_4$ is phenyl substituted with two R$_{11}$.

19. The compound of claim 1, or a pharmaceutically acceptable or a pharmaceutically acceptable solvate thereof, wherein R$_{11}$ is —SO$_2$R$_{10}$.

20. The compound of claim 1, or a pharmaceutically acceptable or a pharmaceutically acceptable solvate thereof, wherein R$_{11}$ is C$_1$-C$_6$heteroalkyl.

21. The compound of claim 1, or a pharmaceutically acceptable or a pharmaceutically acceptable solvate thereof, wherein X is —O—, L$_1$ is a bond, R$_1$ is —CF$_3$, L$_2$ is C$_1$-C$_6$alkyl, R$_2$ is C(═O)OR$_9$, R$_9$ is C$_1$-C$_6$alkyl, R$_4$ is phenyl substituted with one R$_{11}$, R$_{11}$ is —SO$_2$R$_{10}$, and R$_{10}$ is C$_1$-C$_6$alkyl.

22. The compound of claim 1, or a pharmaceutically acceptable or a pharmaceutically acceptable solvate thereof, wherein R$_3$ is hydrogen or halogen.

23. The compound of claim 1, or a pharmaceutically acceptable or a pharmaceutically acceptable solvate thereof, selected from:

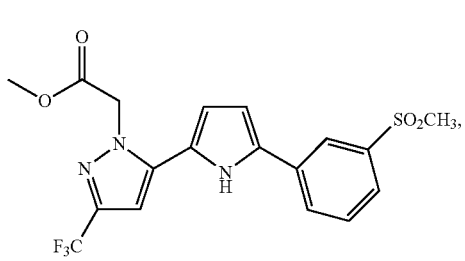

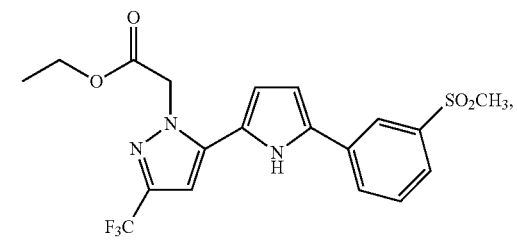

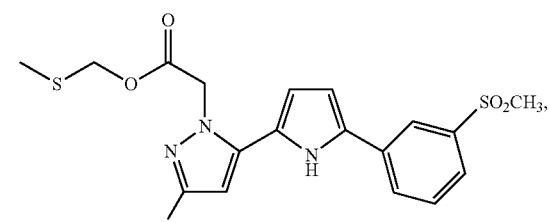

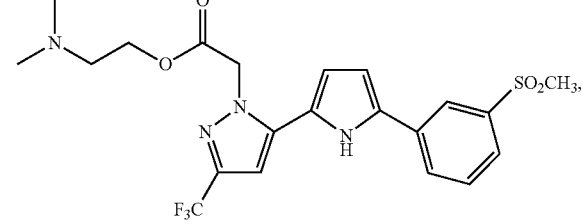

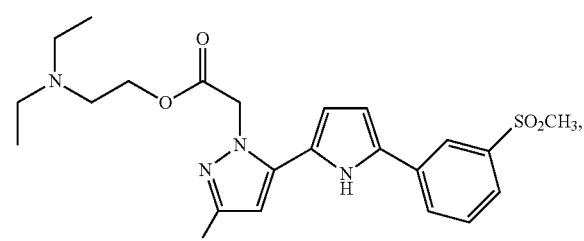

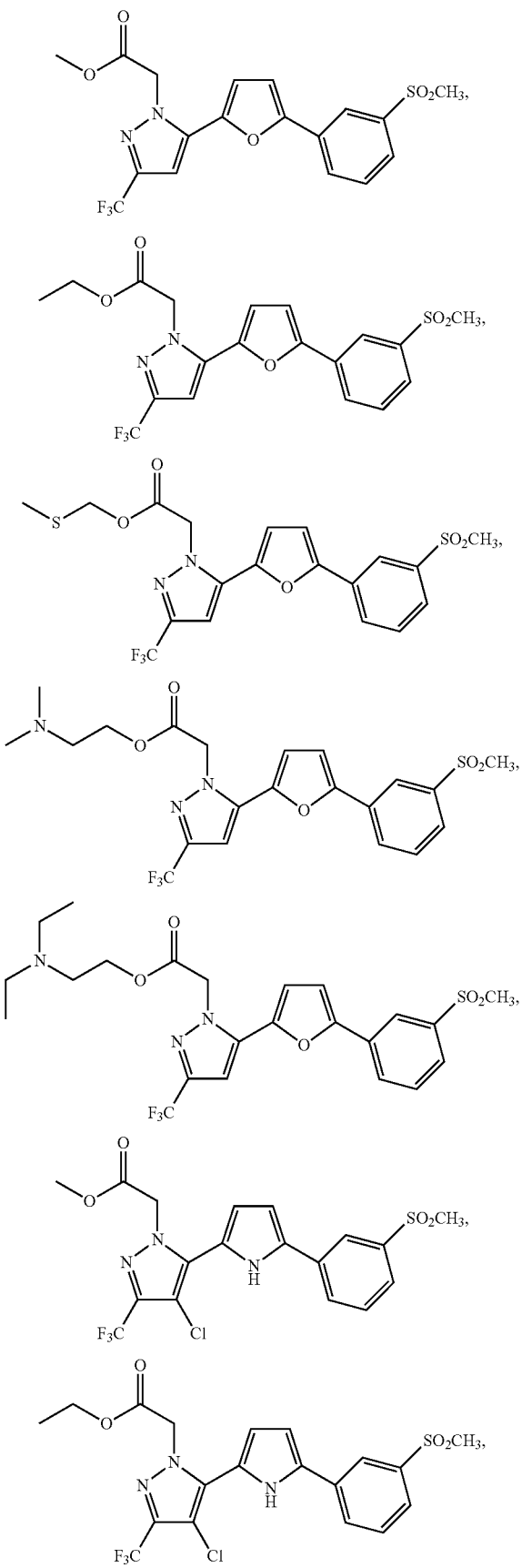
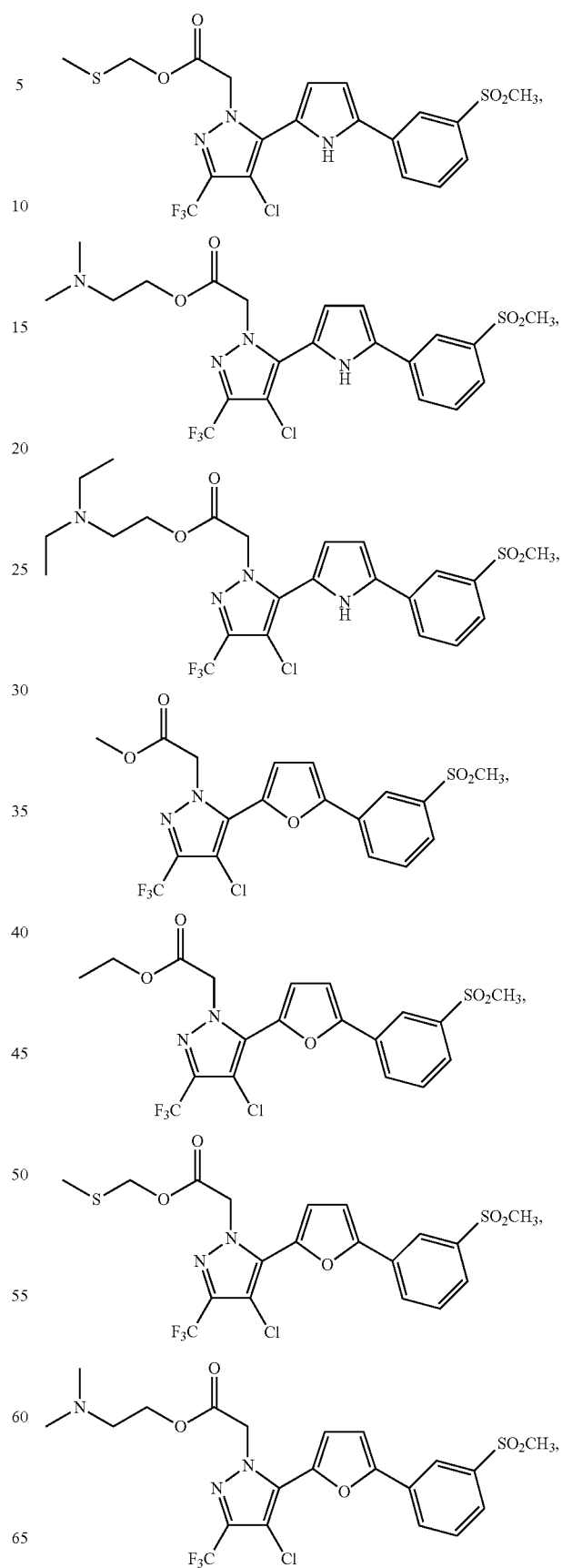

147
-continued
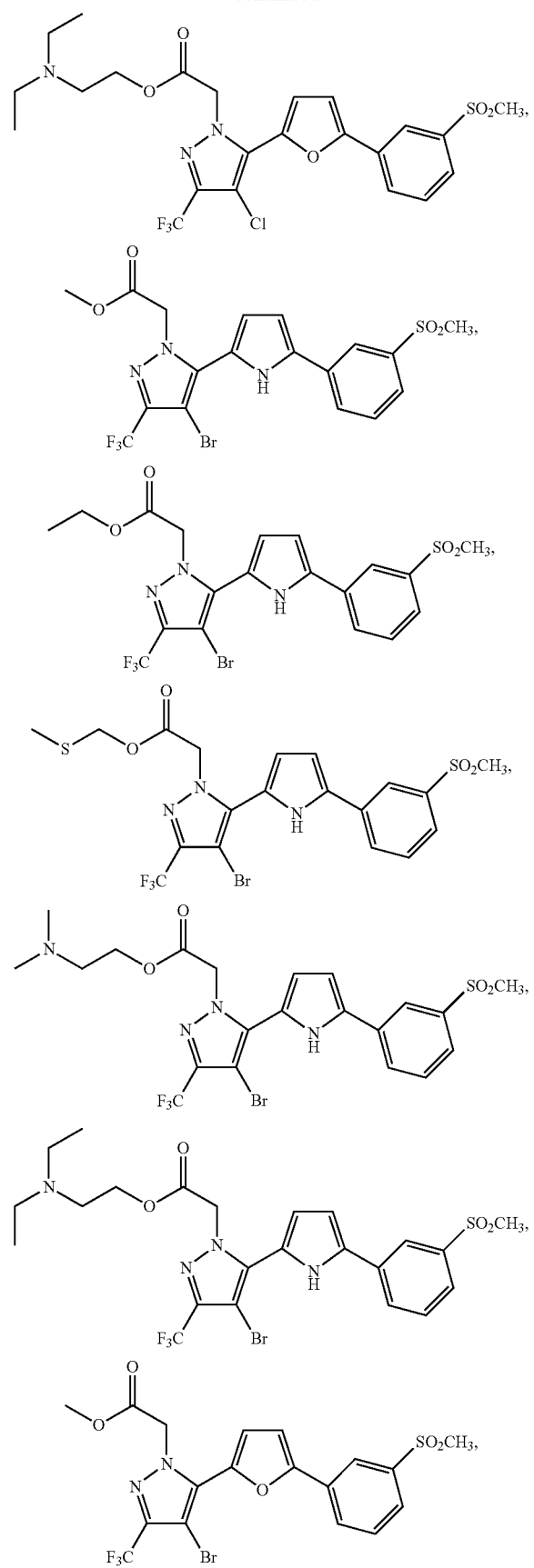
148
-continued
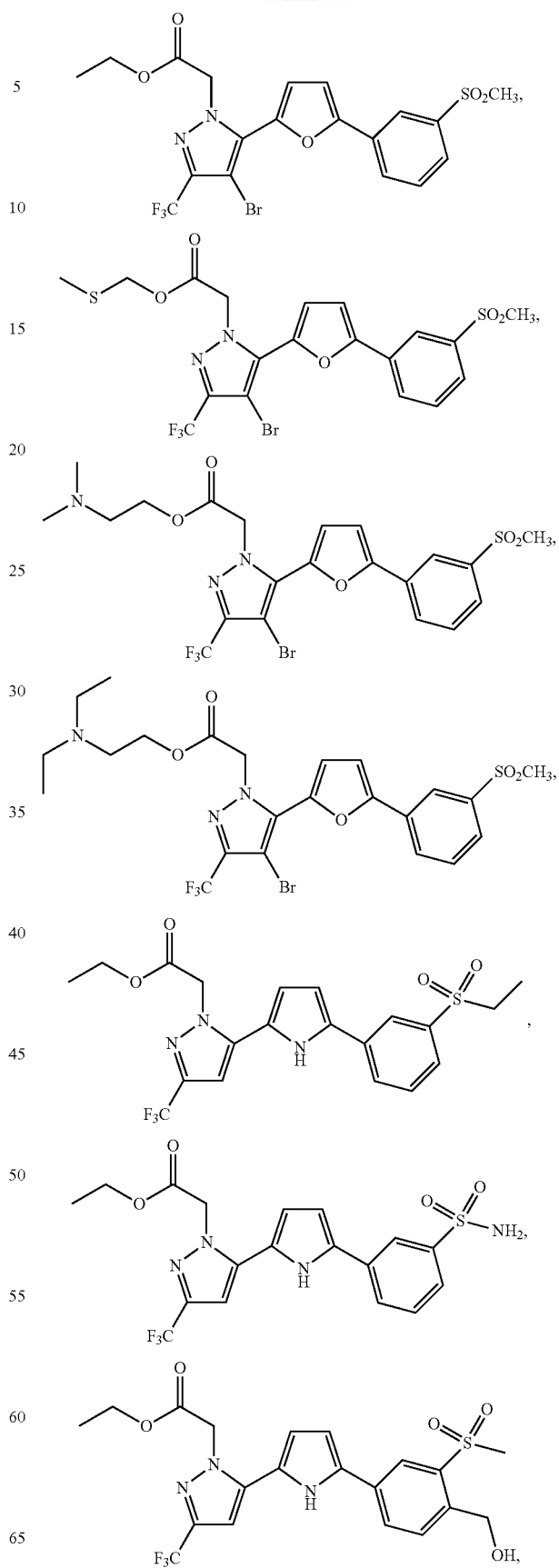

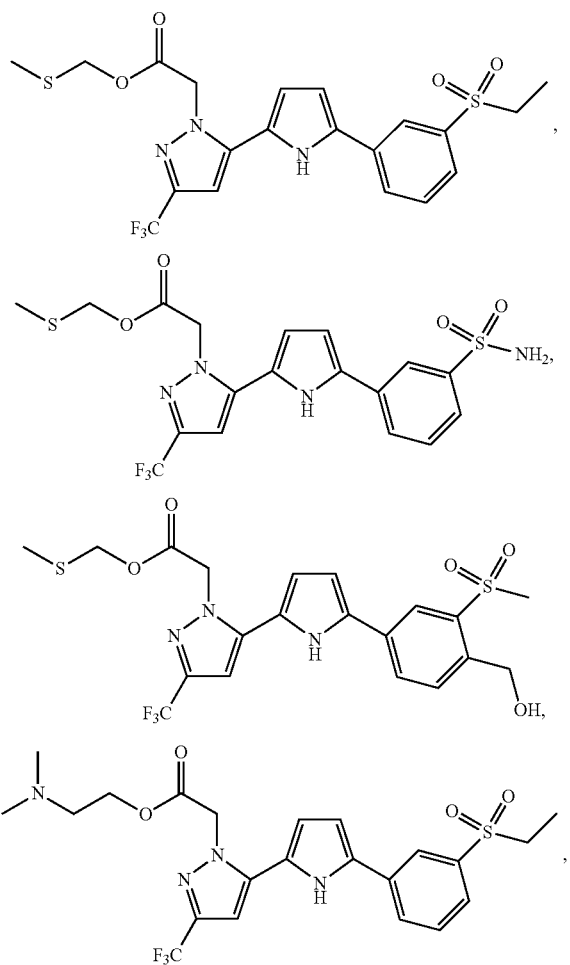

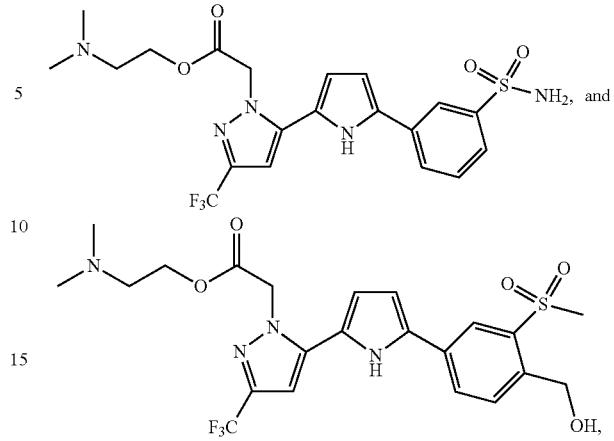

or a pharmaceutically acceptable salt or a pharmaceutically acceptable solvate thereof.

24. A pharmaceutical composition comprising a pharmaceutically acceptable diluent, excipient or binder, and a compound of claim 1, or a pharmaceutically acceptable salt or a pharmaceutically acceptable solvate thereof.

25. A method of treating a disease, disorder or condition selected from selected from skin aging, scarring, psoriasis, dermatitis, eczema, urticaria, rosacea, burns, acne, ichthyoses, vitiligo, metastatic melanoma, and xerosis in a mammal, comprising administering to the mammal a compound of claim 1, or a pharmaceutically acceptable salt or a pharmaceutically acceptable solvate thereof.

26. The method of claim 25, wherein the disease is dermatitis.

27. The method of claim 26, wherein the dermatitis is atopic dermatitis.

28. The method of claim 26, wherein the dermatitis is dermatitis resulting from allergic and irritant contact.

* * * * *